(12) United States Patent
Sanchez et al.

(10) Patent No.: US 11,172,826 B2
(45) Date of Patent: Nov. 16, 2021

(54) NON-INVASIVE DETECTION OF SKIN DISEASE

(71) Applicant: Enspectra Health, Inc., Mountain View, CA (US)

(72) Inventors: Gabriel Sanchez, Menlo Park, CA (US); Fred Landavazo, IV, East Palo Alto, CA (US); Scott Delp, Stanford, CA (US); Kathryn Montgomery, Mountain View, CA (US)

(73) Assignee: ENSPECTRA HEALTH, INC., Mountain View, CA (US)

( * ) Notice: Subject to any disclaimer, the term of this patent is extended or adjusted under 35 U.S.C. 154(b) by 367 days.

(21) Appl. No.: 16/123,447

(22) Filed: Sep. 6, 2018

(65) Prior Publication Data

US 2019/0133452 A1    May 9, 2019

Related U.S. Application Data

(63) Continuation of application No. PCT/US2017/021439, filed on Mar. 8, 2017.

(60) Provisional application No. 62/305,207, filed on Mar. 8, 2016, provisional application No. 62/437,507, filed on Dec. 21, 2016.

(51) Int. Cl.
*A61B 5/00* (2006.01)
*A61B 5/107* (2006.01)

(52) U.S. Cl.
CPC .......... *A61B 5/0077* (2013.01); *A61B 5/0071* (2013.01); *A61B 5/0075* (2013.01); *A61B 5/0079* (2013.01); *A61B 5/1072* (2013.01); *A61B 5/1079* (2013.01); *A61B 5/442* (2013.01); *A61B 5/444* (2013.01)

(58) Field of Classification Search
CPC combination set(s) only.
See application file for complete search history.

(56) References Cited

U.S. PATENT DOCUMENTS 3,655,259 A   4/1972   Miyauchi et al.
4,270,843 A   6/1981   Goto
(Continued)

FOREIGN PATENT DOCUMENTS

AT   257294 T   1/2004
AU   4145801 A  8/2001
(Continued)

OTHER PUBLICATIONS

Anderson, et al., Contributions of muscle forces and tow-off kinematics to peak knee flexion during the swing phase of normal gait: an induced position analysis, Journal of Biomechanics, 37:731-737 (2004).
(Continued)

*Primary Examiner* — Joel F Brutus
(74) *Attorney, Agent, or Firm* — Wilson Sonsini Goodrich & Rosati

(57) ABSTRACT

In some aspects, the present disclosure provides methods for identifying a disease in an epithelial tissue of a subject. Methods for identifying a disease in an epithelial tissue comprise the generation of a depth profile of the epithelial tissue using signals generated from the tissue by pulses of light directed towards a surface of the epithelial tissue. In some aspects, the present disclosure provides apparatuses consistent with the methods herein.

22 Claims, 29 Drawing Sheets

Optical System Modules

(56) References Cited

U.S. PATENT DOCUMENTS

| | | | |
|---|---|---|---|
| 4,416,519 A | 11/1983 | Kobayashi | |
| 4,515,444 A | 5/1985 | Prescott et al. | |
| 4,570,641 A | 2/1986 | Lieber et al. | |
| 4,598,715 A | 7/1986 | Machler et al. | |
| 4,693,606 A | 9/1987 | Podolsky et al. | |
| 5,056,530 A | 10/1991 | Butler et al. | |
| 5,093,719 A | 3/1992 | Prescott | |
| 5,159,402 A | 10/1992 | Ortiz, Jr. | |
| 5,161,063 A | 11/1992 | Krill et al. | |
| 5,181,511 A | 1/1993 | Nickolls et al. | |
| 5,361,166 A | 11/1994 | Atkinson et al. | |
| 5,457,576 A | 10/1995 | Atkinson et al. | |
| 5,880,465 A * | 3/1999 | Boettner | G02B 21/0028 250/201.3 |
| 5,929,985 A | 7/1999 | Sandison et al. | |
| 5,991,090 A | 11/1999 | Strahle | |
| 6,032,071 A | 2/2000 | Binder | |
| 6,198,834 B1 | 3/2001 | Belk et al. | |
| 6,208,886 B1 | 3/2001 | Alfano et al. | |
| 6,405,070 B1 | 6/2002 | Banerjee | |
| 6,485,413 B1 | 11/2002 | Boppart et al. | |
| 6,542,665 B2 | 4/2003 | Reed et al. | |
| 6,546,278 B2 | 4/2003 | Walsh | |
| 6,571,118 B1 | 5/2003 | Utzinger et al. | |
| 6,580,941 B2 | 6/2003 | Webb | |
| 6,639,674 B2 | 10/2003 | Sokolov et al. | |
| 6,643,071 B2 | 11/2003 | Schnitzer | |
| 6,697,652 B2 | 2/2004 | Georgakoudi et al. | |
| 6,760,112 B2 | 7/2004 | Reed et al. | |
| 6,766,184 B2 | 7/2004 | Utzinger et al. | |
| 6,785,471 B2 | 8/2004 | Lee et al. | |
| 6,795,199 B2 | 9/2004 | Suhami | |
| 6,839,483 B2 | 1/2005 | Reed et al. | |
| 6,839,586 B2 | 1/2005 | Webb | |
| 6,839,596 B2 | 1/2005 | Nelson et al. | |
| 6,889,075 B2 | 5/2005 | Marchitto et al. | |
| 6,912,412 B2 | 6/2005 | Georgakoudi et al. | |
| 6,967,725 B2 | 11/2005 | Denk et al. | |
| 7,091,500 B2 | 8/2006 | Schnitzer | |
| 7,307,774 B1 | 12/2007 | Schnitzer et al. | |
| 7,336,988 B2 | 2/2008 | Schnitzer | |
| 7,336,990 B2 | 2/2008 | Genet et al. | |
| 7,414,729 B2 | 8/2008 | Xie et al. | |
| 7,485,100 B2 | 2/2009 | Garcia-Webb et al. | |
| 7,702,381 B2 | 4/2010 | Gaeta et al. | |
| 8,068,899 B2 | 11/2011 | Llewellyn et al. | |
| 8,259,167 B2 | 9/2012 | Ishiwata et al. | |
| 8,380,268 B2 | 2/2013 | Georgakoudi et al. | |
| 8,496,579 B2 | 7/2013 | Koenig et al. | |
| 8,788,021 B1 | 7/2014 | Flusberg et al. | |
| 8,807,801 B2 | 8/2014 | Oldham et al. | |
| 8,897,858 B2 | 11/2014 | Sanchez et al. | |
| 8,912,511 B2 | 12/2014 | Schoenborn et al. | |
| 8,941,087 B2 | 1/2015 | Sun et al. | |
| 9,055,866 B2 | 6/2015 | Narita et al. | |
| 9,411,149 B2 | 8/2016 | Flusberg et al. | |
| 9,433,350 B2 | 9/2016 | Schönborn et al. | |
| 9,433,351 B2 | 9/2016 | Yu et al. | |
| 9,636,020 B2 | 5/2017 | Flusberg et al. | |
| 9,763,577 B2 | 9/2017 | Lee et al. | |
| 9,846,121 B2 | 12/2017 | Schönborn et al. | |
| 9,851,303 B2 | 12/2017 | Huber et al. | |
| 9,983,127 B2 | 5/2018 | Liu et al. | |
| 10,445,879 B1 | 10/2019 | Fuchs et al. | |
| 10,460,150 B2 | 10/2019 | Jackson et al. | |
| 10,499,797 B2 | 12/2019 | Sanchez et al. | |
| 2002/0139920 A1 | 10/2002 | Seibel et al. | |
| 2002/0140942 A1 | 10/2002 | Fee et al. | |
| 2002/0141714 A1 | 10/2002 | Reed et al. | |
| 2002/0146202 A1 | 10/2002 | Reed et al. | |
| 2003/0031410 A1 | 2/2003 | Schnitzer | |
| 2003/0103262 A1 | 6/2003 | Descour et al. | |
| 2003/0117715 A1 | 6/2003 | Schnitzer | |
| 2003/0118305 A1 | 6/2003 | Reed et al. | |
| 2003/0220549 A1 * | 11/2003 | Liu | A61B 5/0059 600/317 |
| 2003/0236458 A1 | 12/2003 | Hochman | |
| 2004/0051957 A1 | 3/2004 | Liang | |
| 2004/0143190 A1 | 7/2004 | Schnitzer | |
| 2004/0249305 A1 | 12/2004 | Reeves et al. | |
| 2004/0254457 A1 | 12/2004 | Van | |
| 2004/0254474 A1 | 12/2004 | Seibel et al. | |
| 2004/0260148 A1 | 12/2004 | Schnitzer | |
| 2005/0038486 A1 | 2/2005 | Mulholland | |
| 2005/0157981 A1 | 7/2005 | Berier et al. | |
| 2005/0207668 A1 | 9/2005 | Perchant et al. | |
| 2005/0242298 A1 | 11/2005 | Genet et al. | |
| 2007/0057211 A1 | 3/2007 | Bahlman et al. | |
| 2007/0159673 A1 * | 7/2007 | Freeman | G02B 27/145 359/19 |
| 2007/0167835 A1 | 7/2007 | Yu et al. | |
| 2007/0263226 A1 * | 11/2007 | Kurtz | G01N 21/6458 356/492 |
| 2007/0283953 A1 * | 12/2007 | Angelini | G04G 21/02 128/201.27 |
| 2008/0297922 A1 | 12/2008 | Lule | |
| 2009/0012406 A1 | 1/2009 | Llewellyn et al. | |
| 2009/0323059 A1 | 12/2009 | Sun et al. | |
| 2010/0177389 A1 | 7/2010 | Rouyer et al. | |
| 2011/0117025 A1 * | 5/2011 | Dacosta | G01N 21/6456 424/9.6 |
| 2011/0125029 A1 | 5/2011 | Wang et al. | |
| 2011/0128373 A1 | 6/2011 | Goldberg | |
| 2011/0152744 A1 | 6/2011 | Choi et al. | |
| 2011/0229640 A1 | 9/2011 | Lee et al. | |
| 2011/0229840 A1 | 9/2011 | Liang et al. | |
| 2012/0080616 A1 | 4/2012 | Schoenborn | |
| 2012/0143065 A1 | 6/2012 | Sanchez et al. | |
| 2012/0184827 A1 | 7/2012 | Shwartz et al. | |
| 2012/0261551 A1 * | 10/2012 | Rogers | G02B 27/28 250/208.1 |
| 2013/0063727 A1 * | 3/2013 | Xu | G01B 11/14 356/479 |
| 2014/0023993 A1 | 1/2014 | Zeng et al. | |
| 2014/0104619 A1 | 4/2014 | Nebosis | |
| 2014/0187879 A1 | 7/2014 | Wood et al. | |
| 2014/0187931 A1 | 7/2014 | Wood et al. | |
| 2014/0187967 A1 | 7/2014 | Wood et al. | |
| 2014/0213897 A1 | 7/2014 | Iftimia et al. | |
| 2014/0276102 A1 | 9/2014 | Lee et al. | |
| 2014/0276103 A1 | 9/2014 | Lee et al. | |
| 2015/0141846 A1 | 5/2015 | Sanchez et al. | |
| 2015/0157254 A1 * | 6/2015 | Sun | A61B 5/0064 600/476 |
| 2015/0164327 A1 | 6/2015 | Yaroslavsky et al. | |
| 2015/0238089 A1 | 8/2015 | Fujinuma et al. | |
| 2015/0265155 A1 | 9/2015 | Zalev et al. | |
| 2016/0022178 A1 | 1/2016 | Wang et al. | |
| 2016/0139388 A1 | 5/2016 | Asundi et al. | |
| 2016/0253466 A1 | 9/2016 | Agaian et al. | |
| 2016/0274346 A1 | 9/2016 | Chiang et al. | |
| 2016/0317037 A1 | 11/2016 | Lee et al. | |
| 2016/0320299 A1 | 11/2016 | Huang et al. | |
| 2016/0377546 A1 | 12/2016 | Ragan et al. | |
| 2017/0010456 A1 | 1/2017 | Gopinath et al. | |
| 2017/0049381 A1 | 2/2017 | Lieber et al. | |
| 2017/0143196 A1 | 5/2017 | Liang et al. | |
| 2017/0209049 A1 | 7/2017 | Wang et al. | |
| 2017/0234675 A1 | 8/2017 | Iddan et al. | |
| 2017/0281077 A1 | 10/2017 | Pyun et al. | |
| 2017/0284940 A1 | 10/2017 | Butte et al. | |
| 2018/0028079 A1 | 2/2018 | Gurevich et al. | |

FOREIGN PATENT DOCUMENTS

| | | |
|---|---|---|
| AU | 2002364332 A1 | 7/2003 |
| AU | 2004297876 A1 | 6/2005 |
| AU | 2007219364 A1 | 4/2008 |
| AU | 2010261751 B2 | 5/2015 |
| AU | 2014236561 B2 | 8/2018 |
| BR | 9911603 A | 2/2001 |
| CA | 2398029 A1 | 8/2001 |

(56) References Cited

FOREIGN PATENT DOCUMENTS

| | | |
|---|---|---|
| CA | 2535843 A1 | 6/2005 |
| CA | 2906056 A1 | 9/2014 |
| CA | 2765620 C | 1/2018 |
| CN | 1303539 A | 7/2001 |
| CN | 105473051 A | 4/2016 |
| DE | 19823955 A1 | 12/1999 |
| DE | 102006046925 A1 | 4/2008 |
| DE | 102009024943 A1 | 12/2010 |
| DE | 102009029831 A1 | 1/2011 |
| EP | 0594388 A1 | 4/1994 |
| EP | 1259163 A2 | 11/2002 |
| EP | 1082816 B1 | 1/2004 |
| EP | 1994874 A1 | 11/2008 |
| EP | 1929939 B1 | 12/2014 |
| EP | 2440119 B1 | 5/2015 |
| EP | 1664854 B1 | 7/2015 |
| EP | 2932892 A1 | 10/2015 |
| EP | 2443503 B1 | 12/2015 |
| EP | 2953215 A1 | 12/2015 |
| EP | 2967280 A2 | 1/2016 |
| EP | 3087423 A1 | 11/2016 |
| EP | 3095001 A2 | 11/2016 |
| EP | 3097443 A1 | 11/2016 |
| EP | 3171766 A1 | 5/2017 |
| EP | 1461601 B1 | 8/2017 |
| EP | 3273285 A1 | 1/2018 |
| ES | 2214875 T3 | 9/2004 |
| ES | 2544804 T3 | 9/2015 |
| ES | 2564529 T3 | 3/2016 |
| ES | 2647468 T3 | 12/2017 |
| FR | 2834340 B1 | 7/2004 |
| JP | 2002517117 A | 6/2002 |
| JP | 2003052642 A | 2/2003 |
| JP | 2004500197 A | 1/2004 |
| JP | 2005515434 A | 5/2005 |
| JP | 2006079000 A | 3/2006 |
| JP | 2007503851 A | 3/2007 |
| JP | 2007532982 A | 11/2007 |
| JP | 2008100057 A | 5/2008 |
| JP | 2008539436 A | 11/2008 |
| JP | 2011257215 A | 12/2011 |
| JP | 2016520339 A | 7/2016 |
| JP | 2017502300 A | 1/2017 |
| JP | 2017504836 A | 2/2017 |
| JP | 2017525435 A | 9/2017 |
| KR | 20160037834 A | 4/2016 |
| KR | 20170038024 A | 4/2017 |
| NZ | 520257 A | 10/2005 |
| RU | 2235420 C2 | 8/2004 |
| TW | 201634901 A | 10/2016 |
| TW | 201740101 A | 11/2017 |
| UA | 44939 C2 | 3/2002 |
| WO | WO-9962176 A1 | 12/1999 |
| WO | WO-0159423 A2 | 8/2001 |
| WO | WO-03060493 A1 | 7/2003 |
| WO | WO-2005057244 A2 | 6/2005 |
| WO | WO-2007000165 A1 | 1/2007 |
| WO | WO-2007014213 A2 | 2/2007 |
| WO | WO-2007105495 A1 | 9/2007 |
| WO | WO-2009157229 A1 | 12/2009 |
| WO | WO-2010142672 A1 | 12/2010 |
| WO | WO-2010146134 A2 | 12/2010 |
| WO | WO-2013082156 A1 | 6/2013 |
| WO | WO-2014012110 A2 | 1/2014 |
| WO | WO-2014137357 A1 | 9/2014 |
| WO | WO-2014152389 A1 | 9/2014 |
| WO | WO-2014152797 A2 | 9/2014 |
| WO | WO-2015002614 A1 | 1/2015 |
| WO | WO-2015054666 A1 | 4/2015 |
| WO | WO-2015100421 A1 | 7/2015 |
| WO | WO-2015109323 A2 | 7/2015 |
| WO | WO-2015112770 A1 | 7/2015 |
| WO | WO-2015168594 A1 | 11/2015 |
| WO | WO-2015185620 A1 | 12/2015 |
| WO | WO-2016015052 A1 | 1/2016 |
| WO | WO-2016145633 A1 | 9/2016 |
| WO | WO-2017139716 A1 | 8/2017 |
| WO | WO-2017156182 A1 | 9/2017 |
| WO | WO-2017173315 A1 | 10/2017 |
| WO | WO-2018018160 A1 | 2/2018 |
| WO | WO-2018201082 A1 | 11/2018 |
| WO | WO-2020102442 A1 | 5/2020 |

OTHER PUBLICATIONS

Armstrong, et al., In vivo size and shape measurement of the human upper airway using endoscopic longrange optical coherence tomography, Opt. Express, 11:1817-26 (2003).

Boulesteix, et al., Second-harmonic Microscopy of Unstained Living Cardiac Myocytes: Measurements of sarcomere length with 20-nm accuracy, Optics Letters, Sep. 1, 2004, 29(17):2031-33.

Brown, et al., Dynamic imaging of collagen and its modulation in tumors in vivo using second-harmonic generation, Nature Medicine, 9:796-800 (2003).

Campagnola, et al., Nonlinear Optical Spectroscopy, Optics & Photonics News, Jun. 2003, pp. 40-45.

Campagnola, et al. Three-dimensional high-resolution second-harmonic generation imaging of endogenous structural proteins in biological tissues. Biophysical Journal. 2002; 81:493-508.

Chu, et al., Studies of X(2)/X(3) Tensors in Submicron-Scaled Bio-Tissues by Polarization Harmonics Opticain Microscopy, Biophysical Journal, 86: 3914-22 (Jun. 2004).

Delp, et al., An Interactive Graphics-based Model of the Lower Extremity to Study Orthopedic Surgical Procedures, IEEE Trans Biomed Eng., 37: 757-767. (1990).

Delp, et al., Open Sim: Open-Source Software to create and analyze dynamic simulations of movement, Biomedical Engineering IEEE, 54: 1940-50 (Nov. 2007) Abstract Only.

Dutton, H. Understanding Optical Communications, IBM, International Technical Support Organization Sep. 1998. Available at http://www.redbooks.ibm.com.

Edman, et al., Depression of tetanic force induced by loaded shortening of frog muscle fibres, J Physiol., 466: 535-552 (1993).

EPO. European Patent Application No. 12853081, Supplementary European Search Report. (dated Jun. 22, 2015).

EPO. European Patent Application No. 12853081.3, Examination Report, 6 pgs. (dated Nov. 24, 2016).

Flusberg, et al., In Vivo Brain Imaging Using a Portable 3.9 Gram Two-photon Fluorescence Microendoscope, Optics Letters 30(17):2272-74 (Sep. 2005).

Freund, et al., Connective Tissue Polarity: Optical Second-harmonic Microscopy, Crossed-beam Summation, and Small-angle Scattering in Rat-tail Tendon, Biophysical Journal, 50: 693-712 (Oct. 1986).

Friden, et al., Physiologic consequences of surgical lengthening of extensor carpi radialis brevis muscle-tendon junction for tennis elbow, J Hand Surg., 19: 269-274 (1994). Abstract Only.

Fu, et al., Integration of a Double-clad Photonic Crystal Fiber, a GRIN lens and a MEMS mirror for nonlinear optical endoscopy, BIO Meeting, Fort Lauderdale (Mar. 19, 2006).

Fu, et al., Nonlinear optical endoscopy based on a double clad photonic crystal fiber and a MEMS mirror, Optics Express, 14(3):1027-32 (Feb. 2006).

Gollapudi, et al., Experimental determination of sarcomere force-length relationship in type-1 human skeletal muscle fibers, J Biomech 42, pp. 2011-2016 (2009) Abstract Only.

Gordon, et al., The variation in isometric tension with sarcomere length in vertebrate muscle fibers, J Physiol, 184: 170-92. (1966).

Guo, et al., Second-harmonic Tomography of Tissues, Optics Letters, Sep. 1, 1997, 22(17):1323-25.

Guo, et al., Subsurface tumor progression investigated by noninvasive optical second harmonic tomography, Proc. Nat'l. Academy of Science, Sep. 1999, 96: 10854-856.

Helmchen, et al., Deep Tissue two-photon microscopy, Nature Methods, 2(12):932-940 (Dec. 2005).

Imaging and Optical technology at Aberdeen, Optics and Laser Technology 25(6), pp. 399-405 (1993).

(56) References Cited

OTHER PUBLICATIONS

Infantolino, et al., Individual sarcomere lengths in whole muscle fibers and optimal fiber length computation, Analrec (Hoboken) 293, pp. 1913-1919 (2010).
International search report and written opinion dated Jul. 26, 2017 for PCT Application No. PCT/US2017/21439.
Julian, et al., Intersarcomere dynamics during fixed-end tetanic contractions of frog muscle fibres, J Physiol., 293: 365-78 (1979).
Julian, et al., Sarcomere length-tension relations of frog skinned muscle fibres at lengths above the optimum, J Physiol., 304: 529-39 (1980).
Jung, et al., In vivo mammalian brain imaging using one- and two-photon fluorescence microendoscopy, J. Neurophysiol, 92:3121-33 (May 2004).
Jung, et al., Multiphoton endoscopy, Optics Letters, 28(11):902-904 (Jun. 2003).
Koch, G. MEMS-based scanning device facilitates microendoscopy. Optics Letters, Jul. 1, 2006. pp. 1-3, Online: http://www.photonics.com/Article.aspx?AID=43392, Accessed Feb. 20, 2016.
Konig, et al., High-resolution multiphoton tomography of human skin with subcellular spatial resolution and picosecond lime resolution, Society of Photo-OpticalInstrum Engineers. (2003) Abstract Only.
Lee, et al., Integrated semiconductor optical sensor for chronic, minimally-invasive imaging of brain functions, Proceedings of the 28th IEEE, pp. 1025-1028 (Aug.-Sep. 2006).
Levene, et al., In vivo multiphoton microscopy of deep brain tissue, J. Neurophysiol, 91: 1908-12 (Dec. 2003).
Lieber, et al., Biomechanical properties of the brachioradialis muscle: Implications for surgical tendon transfer, The Journal of Hand Surgery, 30A(2):273-282 (Mar. 2005).
Lieber, et al., In Vivo Measurement of Human Wrist Extensor Muscle Sarcomere Length Changes, Journal of Neurophysiology, 71(3): 874-881 (Mar. 1994).
Lieber, et al., Sarcomere length in wrist extensor muscles, Changes may provide insights into the etiology of chronic lateral epicondylitis, Acta Orthop Scand, 68:249-254 (1997).
Ljung, et al., Sarcomere length varies with wrist ulnar deviation but not forearm pronation in the extensor carpi radialis brevis muscle, J Biomech., 32:199-202 (1999).
Llewellyn, et al., Minimally invasive high-speed imaging of sarcomere contractile dynamics in mice and humans, Nature 454, 784-788 (2008).
Manal, et al. A real-time EMG-driven virtual arm, Comput. Bioi. Med., 32(1):25-26 (Jan. 2002) Abstract Only.
Mertz, et al., Second-harmonic generation by focused excitation of inhomogeneously distributed scatterers, Optics Communications 196: 325-330 (2001).
Mertz, Nonlinear microscopy: New techniques and applications, Current Opinion in Neurobiology, 14:610-616 (2004).
Messerschmidt, et al., Novel concept of GRIN optical systems for high resolution microendoscopy. Part 1: Physical aspects, Proc. of SPIE 6432, p. 643202-1-643202-9 (2007).
Mohler, et al., Second-harmonic generation imaging of endogenous structural proteins, Methods, 29:97-109 (2003).
Monfared, et al., In Vivo Imaging of Mammalian Cochlear Blood Flow Using Fluorescence Microendoscope, Otology and Neurotology, 27:144-152 (2006).
Moreaux, et al., Coherent Scattering in Multi-Harmonic Light Microscopy, Biophysical Journal, 80: 1568-74 (Mar. 2001).
Murray, et al., Variability in surgical technique for brachioradialis tendon transfer, Evidence and implications, J Bone Joint Surg. Am., 88: 2009-16 (2006).
Niell, et al., Live Optical Imaging of Nervous System Development, Annu. Rev. Physiol., 66:771-798 and C1-C5 (2004).
Nucciotti, et al., Functional imaging of muscle cells by Second Harmonic Generation, Proc. of SPIE, 6089: 608911-1-608911-8 (2006).
Office Action dated Nov. 3, 2017 for U.S. Appl. No. 14/546,085.
Office action dated Jan. 27, 2017 for U.S. Appl. No. 14/546,085.
Panchangam, et al., A novel optical imaging system for investigating sarcomere dynamics in single skeletal muscle fibers, Proc. of SPIE, 6088: 608808-1-608808-11 (2006).
PCT/US12/66860 International Search Report and Written Opinion dated Apr. 17, 2013.
Plotnikov, et al., Characterization of the Myosin-based source for Second-Harmonic Generation from muscle sarcomeres, Biophysical Journal, 90:693-703 (Jan. 2006).
Plotnikov, et al., Measurement of muscle disease by quantitative second-harmonic generation imaging, J. Biomed. Opt. 13 (Aug. 2008) Abstract Only.
Plotnikov, et al., Optical Clearing for Improved Contrast in Second Harmonic Generation Imaging of Skeletal Muscle, Biophysical Journal, 90:328-339 (Jan. 2006).
Ponten, et al., Intraoperative muscle measurements reveal a relationship between contracture formation and muscle remodeling, Muscle & Nerve 36, pp. 47-54 (Jul. 2007).
Rothstein, et al., Multi-photon excitation microscopy in intact animals, Journal of Microscopy, 22:58-64 (2006).
Rothstein, et al., Skeletal Muscle NAD(P)H Two-photon fluorescence microscopy in vivo: Topology and Optical inner filters, Biophysical Journal, 88: 2165-76 (Mar. 2005).
Schenkl, et al., Applications of rigid and flexible GRIN-endoscopes, Proc. of SPIE 6433, pp. 64330N-1-64330N-7 (2007).
Shaw, et al., Infrared spectroscopy of dystrophic mdx mouse muscle tissue distinguishes among treatment groups, J. Applied Physiol. 81: 2328-2335 (1996).
Smith, et al., Hamstring contractures in children with spastic cerebral palsy result from a stiffer extracellular matrix and increased in vivo sarcomere length, J Physiol., 589: 2625-2639. (2011).
Jung, et al. Miniaturized probe using 2 axis MEMS scanner for endoscopic multiphoton excitation microscopy. Proceedings of SPIE— The International Society for Optical Engineering, vol. 6851, Mar. 2008, pp. 1-7.
U.S. Appl. No. 14/546,085 Office Action dated Jun. 8, 2016.
U.S. Appl. No. 14/546,085 Office Action dated Feb. 26, 2016.
U.S. Appl. No. 14/546,085 Office Action dated Oct. 10, 2018.
Williams, et al., Interpreting Second-Harmonic Generation Images of Collagen I Fibrils, Biophysical Journal, 88:1377-86 (Feb. 2005).
Zipfel, et al., Live tissue intrinsic emission microscopy using multiphoton-exciled native fluorescence and second harmonic generation, PNAS 100(12):7075-80 (Jun. 2003).
Zoumi, et al., Imaging cells and Extracellular Matrix in vivo by using Second-harmonic Generation and two-photon excited fluorescence, PNAS, Aug. 20, 2002, 99(17):11014-19.
EP12853081.3 Examination Report dated Mar. 27, 2020.
EP12853081.3 Examination Report dated Nov. 9, 2017.
PCT/US2019/061306 International Search Report dated Mar. 9, 2020.
Co-pending U.S. Appl. No. 16/585,789, filed Sep. 27, 2019.
Co-pending U.S. Appl. No. 16/662,830, filed Oct. 24, 2019.
EP17764041.4 The Extended European Search Report dated Sep. 25, 2019.
Botcherby, et al. Fast measurement of sarcomere length and cell orientation in Langendorff-perfused hearts using remote focusing microscopy. Circ Res. Sep. 13, 2013;113(7):863-70. doi: 10.1161/CIRCRESAHA.113.301704. Epub Jul. 30, 2013.
Gobel, et al. New angles on neuronal dendrites in vivo. J Neurophysiol. Dec. 2007;98(6):3770-9. Epub Sep. 26, 2007.
Olivier, et al. Cell lineage reconstruction of early zebrafish embryos using label-free nonlinear microscopy. Science. Aug. 20, 2010;329(5994):967-71. doi: 10.1126/science.1189428.
PCT/US2018/030011 International Search Report and Written Opinion dated Aug. 14, 2018.
U.S. Appl. No. 14/546,085 Notice of Allowance dated Jul. 22, 2019.
Co-pending U.S. Appl. No. 17/096,602, inventors Sanchez; Gabriel et al., filed on Nov. 12, 2020.
EP18791038.5 The Extended European Search Report dated Dec. 22, 2020.

\* cited by examiner

Identify tumor edges for rapid tumor removal

401 Healthy     402 Cancerous

Classical Pathology

Invasive, 45 minute delay, poor dye contrast

Polychromatic

601
602

Non-invasive, instantaneous, customizable contrast

Classical Pathology

Invasive, 45 minute delay, poor dye contrast

Monochromatic

603
604

Non-invasive, instantaneous, customizable contrast

Optical System Modules

NON-INVASIVE DETECTION OF SKIN DISEASE

CROSS-REFERENCE

This application is a continuation of Patent Cooperation Treaty Application No. PCT/US2017/021439, filed on Mar. 8, 2017, which claims priority to U.S. Provisional Patent Application Ser. No. 62/305,207, filed Mar. 8, 2016, and U.S. Provisional Patent Application Ser. No. 62/437,507, filed Dec. 21, 2016, each of which is entirely incorporated herein by reference.

BACKGROUND

Skin cancer, a type of epithelial cancer, is one of the most common cancers. Skin cancer can occur on various parts of the body, including the face in areas such as the cheeks and near the eyes, nose, and mouth. Skin cancer can be surgically removed to prevent spreading. A goal of surgeries may be to remove all of the cancer without removing too much healthy skin from the face. To do this, a surgeon may draw a boundary around the visible skin cancer lesion, or the area of the skin where the cancer is present, and then cut along this boundary to remove the cancer. In some cases, some amount of healthy tissue may also be removed to ensure that most, if not all, of the cancer is removed. This type of surgery can be referred to as a Mohs surgery, named after the surgeon who invented the procedure in the 1930s. Mohs surgery is largely unchanged since its introduction, and over 2.5 million surgeries are performed in the United States each year.

Mohs surgery can be performed without knowledge of the boundaries of the cancer, and in some cases, the amount of tissue to remove may not be determined with certainty. As a result, healthy skin may be removed. In approximately half of the surgeries, cancer may remain. During this procedure, a patient may wait while a surgeon analyzes the removed tissue. The analysis, in some cases, may involve histological preparations of the tissue for microscopic analysis, a process that can take approximately one hour. The surgeon, or in some cases a pathologist, may then examine the tissue to determine if the boundary of the tissue that was removed contains cancer or is free from cancer. If some cancer remains, such as may be the case for approximately half of these surgeries, a second surgical procedure can be performed to remove more tissue. This tissue may then be prepared for microscopic analysis while the patient waits again for the results. In approximately 20 percent of these cases, some cancer may still be present, and a third surgery may be required. Up to eight surgeries may be required to remove all of the cancer. This process can be painful for the patient, costly for insurance companies, and inefficient for the surgeon.

SUMMARY

Provided herein are methods and apparatuses that may be useful for non-invasive detection of skin disease.

In an aspect, a method for identifying a disease in an epithelial tissue of a subject comprises (a) using an optical probe to transmit pulses of a single beam of light from a light source towards a surface of the epithelial tissue, which pulses of the single beam of light, upon contacting the epithelial tissue, generate signals that relate to an intrinsic property of the epithelial tissue; (b) collecting at least a subset of the signals at a plurality of different focal planes of the pulses of the single beam of light; and (c) using a programmed computer processor to process the subset of the signals to generate a depth profile of the epithelial tissue, which depth profile is usable to identify the disease in the epithelial tissue of the subject. In some embodiments, (a)-(c) are performed in an absence of removing the epithelial tissue from the subject. In some embodiments, (a)-(c) are performed in an absence of administering a contrast enhancing agent to the subject.

In some embodiments, the pulses of the single beam of light comprise unpolarized light. In some embodiments, the pulses of the single beam of light comprise polarized light. In some embodiments, the polarized light is rotated. In some embodiments, a wavelength of the pulses of the single beam of light is longer than 400 nm.

In some embodiments, the disease is epithelial cancer. In some embodiments, the epithelial cancer is skin cancer. In some embodiments, the depth profile extends at least below a basal layer of the epithelial tissue. In some embodiments, the method further comprises changing a relative position of a mobile lens with respect to the epithelial tissue, which mobile lens is in optical communication with the optical probe, to yield the plurality of different focal planes. In some embodiments, changing the relative position of the mobile lens with respect to the epithelial tissue comprises translating the mobile lens. In some embodiments, the mobile lens is translated at a cyclic rate of at least 0.5 Hz.

In some embodiments, the method further comprises modulating a curvature of an electrically or electro-mechanically tunable lens, which electrically or electro-mechanically tunable lens is in electrical or electro-mechanical communication with the optical probe, to yield the plurality of different focal planes.

In some embodiments, the subset of the signals includes at least one of second harmonic generation (SHG) signals, third harmonic generation (THG) signals, and autofluorescence signals. In some embodiments, the collecting is performed in a presence of ambient light. In some embodiments, the depth profile comprises a monochromatic image. In some embodiments, the depth profile comprises a polychromatic image. In some embodiments, the method further comprises outlining a boundary that is indicative of a location of the disease in the epithelial tissue of the subject. In some embodiments, (a) is performed without penetrating the epithelial tissue of the subject.

In some embodiments, the signals that relate to an intrinsic property of the epithelial tissue are detected by a photomultiplier tube (PMT) sensor. In some embodiments a power and gain of the PMT sensor are modulated to enhance image quality. In some embodiments, the signals that relate to an intrinsic property of the epithelial tissue are detected by a hybrid PMT/avalanche photo diode sensor. In some embodiments, the pulses of a single beam of light are synchronized with sensing by the PMT sensor.

In some embodiments, a maximum resolution depth of the depth profile is increased by inserting a hollow light pipe needle into the epithelial tissue. In some embodiments, the hollow light pipe needle is a single needle. In some embodiments, the hollow light pipe needle is a ring of hollow light pipe needles.

In another aspect, a method for identifying a disease in an epithelial tissue of a subject comprises (a) without penetrating the epithelial tissue of the subject, using an optical probe to transmit pulses of light from a light source towards a surface of the epithelial tissue, wherein the pulses of light, upon contacting the epithelial tissue, generate signals that relate to an intrinsic property of the epithelial tissue, and wherein the pulses of light are directed to the epithelial tissue using a mobile lens at a plurality of different relative positions with respect to the epithelial tissue; (b) collecting at least a subset of the signals generated from the pulses of light; and (c) using a programmed computer processor to process the subset of the signals to generate a profile of the epithelial tissue, which profile is usable to identify the disease in the epithelial tissue of the subject. In some embodiments, the pulses of light are pulses of a single beam of light. In some embodiments, the profile is a depth profile. In some embodiments, the optical probe can make a contact with the surface of the epithelial tissue. In some embodiments, the contact is monitored. In some embodiments, the optical probe is translatable across the surface of the epithelial tissue.

In some embodiments, the collecting is performed in a presence of ambient light. In some embodiments, the optical probe comprises a light shield that reduces the amount of ambient light detected. In some embodiments, the light shield comprises a plurality of layers of opaque bristles. In some embodiments, the light shield is retractable. In some embodiments, the optical probe comprises an additional sensor that detects the amount of ambient light present during collection of the signals generated from the pulses of light and the programmed computer processor is programmed to remove the amount of ambient light from the signals generated from the pulses of light.

In some embodiments, the profile is presented on a customizable display. In some embodiments, the customizable display is attached to the optical probe. In some embodiments, the customizable display is detachable from the optical probe. In some embodiments, the customizable display is a display of a cellular phone attached to the optical probe. In some embodiments, the customizable display has a zoom function. In some embodiments, the customizable display toggles between a wide screen and a high resolution view.

In another aspect, an apparatus for identifying a disease in an epithelial tissue of a subject comprises an optical probe that transmits pulses of a single beam of light from a light source towards a surface of the epithelial tissue, which pulses of the single beam of light, upon contacting the epithelial tissue, generate signals that relate to an intrinsic property of the epithelial tissue; a mobile lens that is in optical communication with the optical probe, wherein during use, the mobile lens yields a plurality of different focal planes with respect to the epithelial tissue; and a programmed computer processor that is programmed to process the signals to generate a depth profile of the epithelial tissue, which depth profile is usable to identify the disease in the epithelial tissue of the subject.

In another aspect, an apparatus for identifying a disease in an epithelial tissue of a subject comprises an optical probe that transmits pulses of a single beam of light from a light source towards a surface of the epithelial tissue, which pulses of the single beam of light, upon contacting the epithelial tissue, generate signals that relate to an intrinsic property of the epithelial tissue; an electrically or electro-mechanically tunable lens that is in electrical or electro-mechanical communication with the optical probe, wherein modulating a curvature of the electrically or electro-mechanically tunable lens yields a plurality of different focal planes with respect to the epithelial tissue; and a programmed computer processor that is programmed to process the signals to generate a depth profile of the epithelial tissue, which depth profile is usable to identify the disease in the epithelial tissue of the subject.

In some embodiments, the optical probe further comprises optical filters, which optical filters collect a subset of the signals. In some embodiments, the optical probe further comprises optical filters, which optical filters collect a subset of the signals, wherein the subset of the signals includes at least one of second harmonic generation (SHG) signals, third harmonic generation (THG) signals, and autofluorescence signals. In some embodiments, the light source comprises an ultra-fast pulse laser with pulse durations less than about 200 femtoseconds. In some embodiments, the optical probe is not a confocal microscope. In some embodiments, the mobile lens is translated to yield the plurality of different focal planes. In some embodiments, the mobile lens is coupled to an actuator that translates the mobile lens. In some embodiments, the optical probe makes a contact with the surface of the epithelial tissue. In some embodiments, the apparatus further comprises a sensor that detects a displacement between the optical probe and the surface of the epithelial tissue. In some embodiments, the optical probe comprises a photomultiplier tube (PMT) that collects the signals. In some embodiments, the optical probe comprises a photomultiplier tube (PMT) that collects the signals, wherein the photomultiplier tube (PMT) further comprises a shutter that is activatable. In some embodiments, the depth profile comprises a monochromatic image on a display. In some embodiments, the depth profile comprises a polychromatic image on a display. In some embodiments, the apparatus further comprises a marking tool for outlining a boundary that is indicative of a location of the disease in the epithelial tissue of the subject. In some embodiments, the optical probe comprises a handheld housing. In some embodiments, the optical probe comprises a hybrid photomultiplier tube (PMT)/avalanche photo diode that collects the signals.

In some embodiments, the apparatus is a portable apparatus. In some embodiments, the portable apparatus is powered by a battery. In some embodiments, the portable apparatus comprises wheels. In some embodiments, the portable apparatus is contained within a housing. In some embodiments, the portable apparatus comprises a filtered light source that emits light within a range of wavelengths not detectable by the optical probe.

In some embodiments, the handheld housing further comprises a display screen. In some embodiments, the display screen is a detachable display screen. In some embodiments, the display screen has a zoom function. In some embodiments, the display screen toggles between a wide screen and a high resolution view. In some embodiments, the display screen comprises and editable feature that allows for marking of the epithelial features on the display screen.

In some embodiments, the handheld housing further comprises at least one camera. In some embodiments, the at least one camera creates a macroscopic image. In some embodiments, the display screen is split and comprises the macroscopic image and the polychromatic image of the depth profile. In some embodiments, the optical probe further comprises a disposable probe tip.

In another aspect, a portable apparatus for identifying a disease in an epithelial tissue of a subject comprises (i) an optical probe that transmits pulses of a single beam of light towards a surface of said epithelial tissue, which pulses of the single beam of light, upon contacting the epithelial tissue, generate signals indicative of an intrinsic property of said epithelial tissue, and (ii) one or more computer processors that are individually or collectively programmed to process said signals to generate a depth profile of said epithelial tissue, which depth profile is usable to identify said disease in said epithelial tissue of the subject, wherein said optical probe has a weight that is less than or equal to about 1 pound and a footprint that is less than or equal to about 1 ft².

In some embodiments, the optical probe is configured to transmit the pulses of the single beam of light towards the surface of the epithelial tissue without penetrating the surface of the epithelial tissue. In some embodiments the optical probe further comprises optical filters, which optical filters collect a subset of the signals, wherein the subset of the signals includes at least one of second harmonic generation (SHG) signals, third harmonic generation (THG) signals, and autofluorescence signals. In some embodiments, the weight is less than or equal to about 0.5 pounds. In some embodiments, the footprint is less than or equal to about 0.5 ft².

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
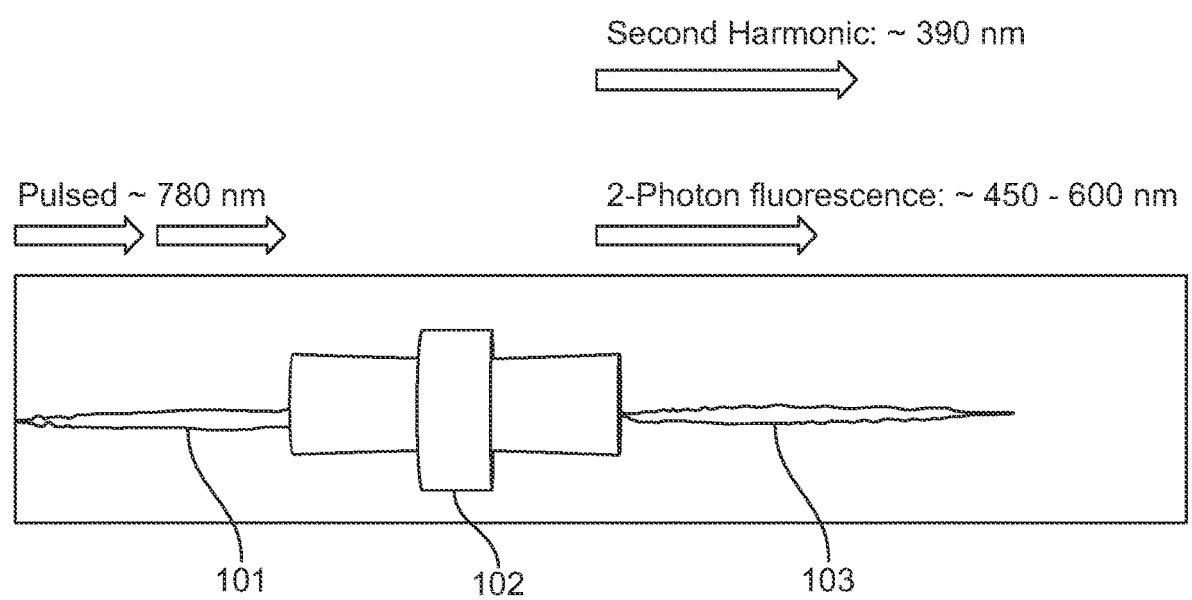
FIG. 1 provides an illustration of the generation of second harmonic and 2-photon fluorescence signals from pulses of about 780 nm light.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein, generally refers to an animal, such as a mammal. A subject may be a human or non-human mammal. A subject may be afflicted with a disease or suspected of being afflicted with a disease. In some cases, the subject is desired to be treated to alleviate the symptoms of the disease or cure the subject of the disease. A subject may be a patient undergoing treatment by a healthcare provider, such as a doctor.

The term "disease," as used herein, generally refers to an abnormal condition, or a disorder of a biological function or a biological structure such as an organ, that affects part or all of a subject. A disease may be caused by factors originally from an external source, such as infectious disease, or it may be caused by internal dysfunctions, such as autoimmune diseases. A disease can refer to any condition that causes pain, dysfunction, distress, social problems, and/or death to the subject afflicted. A disease may be an acute condition or a chronic condition. A disease may refer to an infectious disease, which may result from the presence of pathogenic microbial agents, including viruses, bacteria, fungi, protozoa, multicellular organisms, and aberrant proteins known as prions. A disease may refer to a non-infectious disease, including but not limited to cancer and genetic diseases. In some cases, a disease can be cured. In some cases, a disease cannot be cured.

The terms "epithelial tissue" and "epithelium," as used herein, generally refer to the tissues that line the cavities and surface of blood vessels and organs throughout the body. Epithelial tissue comprises epithelial cells of which there are generally three shapes: squamous, columnar, and cuboidal. Epithelial cells can be arranged in a single layer of cells as simple epithelium comprising either squamous, columnar or cuboidal cells, or in layers of two or more cells deep as stratified (layered), comprising either squamous, columnar and/or cuboidal.

The term "basal layer," as used herein, generally refers to one of the layers of a stratified epithelium. A basal layer may be in contact with a basement membrane, which can refer to a layer of extracellular matrix secreted by epithelial cells, on which the epithelium sits.

The term "cancer," as used herein, generally refers to a proliferative disorder caused or characterized by a proliferation of cells which have lost susceptibility to normal growth control. Cancers of the same tissue type usually originate in the same tissue, and may be divided into different subtypes based on their biological characteristics. Non-limiting examples of categories of cancer are carcinoma (epithelial cell derived), sarcoma (connective tissue or mesodermal derived), leukemia (blood-forming tissue derived) and lymphoma (lymph tissue derived). Cancer may involve every organ and tissue of the body. Specific examples of cancers that do not limit the definition of cancer may include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. In some cases, a cancer can be multicentric. In some cases, a cancer can be a cancer of unknown primary (CUP).

The term "lesion," as used herein, generally refers to areas of disease and/or suspected disease, wounds, incisions, and/or surgical margins. Wounds may include, but are not limited to, scrapes, abrasions, cuts, tears, breaks, punctures, gashes, slices, and/or any injury resulting in bleeding and/or skin trauma sufficient for foreign organisms to penetrate. Incisions may include those made by a medical professional, such as but not limited to, physicians, nurses, mid-wives, and/or nurse practitioners, and dental professionals during treatment such as a surgical procedure.

The term "histopathology," as used herein, generally refers to the microscopic examination of tissue in order to study the manifestations of disease. A tissue can be removed from a subject and then prepared for microscopic examination. A sample can be chemically fixed or processed in frozen sections and then stained, such as with one or more dyes, pigments, and/or antibodies. Staining may be used facilitate examination of the tissue, for example by revealing cellular components and tissue structural components and/or enhancing contrast.

The term "light," as used herein, generally refers to electromagnetic radiation in a range of wavelengths from infrared (e.g. about 700 nm to about 1 mm) through the ultraviolet (e.g. about 10 nm to about 380 nm).

The term "ambient light," as used herein, generally refers to the light surrounding an environment or subject, such as the light in a medical examination or operating room.

The term "focal plane," as used herein, generally refers a plane that is perpendicular to the axis of a lens or mirror and passes through the focal point of the lens or mirror. A focal point generally refers to a point on the axis of a lens or mirror to which parallel rays of light can converge to form an image of a sample.

The term "fluorescence," as used herein, generally refers to radiation that can be emitted as the result of the absorption of incident electromagnetic radiation of one or more different wavelengths. In some cases, fluorescence may result from emissions from exogenously provided tags and/or markers. In some cases, fluorescence may result as an inherent response of one or more endogenous molecules to excitation with electromagnetic radiation.

The term "autofluorescence," as used herein, generally refers to fluorescence from one or more endogenous molecules to excitation with electromagnetic radiation.

The term "multi-photon excitation," as used herein, generally refers to excitation of a fluorophore by more than one photon, resulting in the emission of a fluorescence photon. In some cases, the emitted photon is at a higher energy than the excitatory photons.

The terms "second harmonic generation" and "SHG," as used herein, generally refer to a nonlinear optical process in which photons interacting with a nonlinear material are effectively "combined" to form new photons with about twice the energy, and therefore about twice the frequency and about half ($\frac{1}{2}$) the wavelength of the initial photons.

The terms "third harmonic generation" and "THG," as used herein, generally refer to a nonlinear optical process in which photons interacting with a nonlinear material are effectively "combined" to form new photons with about three times the energy, and therefore about three times the frequency and about a third ($\frac{1}{3}$) the wavelength of the initial photons.

The term "polarized light," as used herein, generally refers to light with waves oscillating in one plane. Unpolarized light can generally refer to light with waves oscillating in more than one plane.

The term "contrast enhancing agent," as used herein, generally refers to any agent such as but not limited to fluorophores, metal nanoparticles, nanoshell composites and semiconductor nanocrystals that can be applied to a sample to enhance the contrast of images of the sample obtained using optical imaging techniques. Fluorophores can be antibody targeted fluorophores, peptide targeted fluorophores, and fluorescent probes of metabolic activity. Metallic nanoparticles can comprise metals such as gold and silver that can scatter light. Nanoshell composites can include nanoparticles comprising a dielectric core and metallic shell. Semiconductor nanocrystals can include quantum dots, for example quantum dots containing cadmium selenide or cadmium sulfide.

The term "depth profile," as used herein, generally refers to a vertical cross-section or approximately vertical cross-section of a sample, such as a tissue sample. For example, a depth profile of a tissue sample, such as a skin tissue, generally refers to a cross-section that extends in a perpendicular direction relative to the surface of the skin tissue. A depth profile can provide information at various depths of the sample, for example at various depths of a skin tissue. A depth profile can be provided in real-time.

The term "monochromatic," as used herein, generally refers to colors of a single hue.

The term "polychromatic," as used herein, generally refers to two or more colors.

The term "in real-time" and "real-time," as used herein, generally refers to immediate, rapid, not requiring operator intervention, automatic, and/or programmed. Real-time may include, but is not limited to, measurements in femtoseconds, picoseconds, nanoseconds, milliseconds, seconds, as well as longer, and optionally shorter, time intervals.

Optical Techniques for Detecting Epithelial Cancers

The present disclosure provides optical techniques that may be used for diagnosing epithelial diseases and skin pathologies. Optical imaging techniques can display nuclear and cellular morphology and may offer the capability of real-time detection of tumors in large areas of freshly excised or biopsied tissue without the need for sample processing, such as that of histology. Optical imaging methods can also facilitate non-invasive, real-time visualization of suspicious tissue without excising, sectioning, and/or staining the tissue sample. Optical imaging may improve the yield of diagnosable tissue (e.g., by avoiding areas with fibrosis or necrosis), minimize unnecessary biopsies or endoscopic resections (e.g., by distinguishing neoplastic from inflammatory lesions), and assess surgical margins in real-time to confirm negative margins (e.g., for performing limited resections). The ability to assess a tissue sample in real-time, without needing to wait for tissue processing, sectioning, and staining, may improve diagnostic turnaround time, especially in time-sensitive contexts, such as during Mohs surgery. Non-limiting examples of optical imaging techniques for diagnosing epithelial diseases and cancers include multiphoton microscopy, autofluorescence microscopy, polarized light microscopy, confocal microscopy, Raman spectroscopy, optical coherence tomography, and ultrasonography.

Multiphoton microscopy (MPM) can be used to image intrinsic molecular signals in living specimens, such as the skin tissue of a patient. In MPM, a sample is illuminated with light at wavelengths longer than the normal excitation wavelength, for example twice as long or three times as long. MPM can include second harmonic generation microscopy (SHG) and third harmonic generation microscopy (THG). Third harmonic generation may be used to image nerve tissue.

Autofluorescence microscopy can be used to image biological molecules (e.g. fluorophores) that are inherently fluorescent. Non-limiting examples of endogenous biological molecules that are autofluorescent include nicotinamide adenine dinucleotide (NADH), NAD(P)H, flavin adenine dinucleotide (FAD), collagen, retinol, and tryptophan and the indoleamine derivatives of tryptophan. Changes in the fluorescence level of these fluorophores, such as with tumor progression, can be detected optically. Changes may be associated with altered cellular metabolic pathways (NADH, FAD) or altered structural tissue matrix (collagen).

Polarized light can be used to evaluate biological structures and examine parameters such as cell size and refractive index. Refractive index can provide information regarding the composition and organizational structure of cells, for example cells in a tissue sample. Cancer can significantly alter tissue organization, and these changes may be detected optically with polarized light.

Confocal microscopy may also be used to examine epithelial tissue. Exogenous contrast agents may be administered for enhanced visibility. Confocal microscopy can provide non-invasive images of nuclear and cellular morphology in about 2-5 micrometer (μm) thin sections in living human skin with lateral resolution of about 0.5-1.0 μm. Confocal microscopy can be used to visualize in vivo micro-anatomic structures, such as the epidermis, and individual cells, including melanocytes.

Raman spectroscopy may also be used to examine epithelial tissue. Raman spectroscopy relies on the inelastic scattering (so-called "Raman" scattering) phenomena to detect spectral signatures of disease progression biomarkers such as lipids, proteins, and amino acids.

Optical coherence tomography may also be used to examine epithelial tissue. Optical coherence tomography is based on interferometry in which a laser light beam is split with a beam splitter, sending some of the light to the sample and some of the light to a reference. The combination of reflected light from the sample and the reference can result in an interference pattern which can be used to determine a reflectivity profile providing information about the spatial dimensions and location of structures within the sample. Current, commercial optical coherence tomography systems have lateral resolutions of about 10 to 15 μm, with depth of imaging of about 1 mm or more. Although this technique can rapidly generate 3-dimensional (3D) image volumes that reflect different layers of tissue components (e.g., cells, connective tissue, etc), the image resolution (e.g., similar to the ×4 objective of a histology microscope) may not be sufficient for routine histopathologic diagnoses.

Ultrasound may also be used to examine epithelial tissue. Ultrasound can be used to assess relevant characteristics of epithelial cancer such as depth and vascularity. While ultrasonography may be limited in detecting pigments such as melanin, it can supplement histological analysis and provide additional detail to assist with treatment decisions. It may be used for noninvasive assessment of characteristics, such as thickness and blood flow, of the primary tumor and may contribute to the modification of critical management decisions.

Methods for diagnosing epithelial diseases and skin pathologies disclosed herein may comprise one or more of multiphoton microscopy, autofluorescence microscopy, polarized light microscopy, confocal microscopy, Raman spectroscopy, optical coherence tomography, and ultrasonography. In some cases, a method for diagnosing an epithelial disease and/or skin pathology comprises autofluorescence microscopy and multiphoton microscopy. As an alternative, a method for diagnosing an epithelial disease and/or skin pathology comprises autofluorescence microscopy, multiphoton microscopy, and polarized light microscopy. Both second harmonic generation microscopy and third harmonic generation microscopy can be used. In some cases, one of second harmonic generation microscopy and third harmonic generation microscopy is used.

Methods for Identifying a Disease in an Epithelial Tissue

Disclosed herein are methods for identifying a disease in an epithelial tissue of a subject. In an aspect, a method for identifying a disease in an epithelial tissue of a subject may comprise using an optical probe to transmit pulses of a single beam of light from a light source towards a surface of the epithelial tissue. The pulses of the single beam of light, upon contacting the epithelial tissue, may generate signals that relate to an intrinsic property of the epithelial tissue. For example, as shown in FIG. 1, pulses of light 101 having a wavelength centered at about 780 nm, upon contacting an element 102, may generate signals 103 that relate to an intrinsic property of the element 102, such as second harmonic signals and 2-photon fluorescence signals. Next, at least a subset of the signals may be collected at a plurality of different focal planes of the pulses of the single beam of light. The subset of the signals may then be processed, for example with the aid of a programmed computer processor, to generate a depth profile of the epithelial tissue. The depth profile may be usable to identify the disease in the epithelial tissue of the subject.

The depth profile can be generated in real-time. For example, the depth profile is generated while the optical probe transmits pulses of a single beam of light from the light source towards the surface of the epithelial tissue. The depth profile may be generated at a frame rate of at least 1 frames per second (FPS), 2 FPS, 3 FPS, 4 FPS, 5 FPS, 10 FPS, or greater. Frame rate generally refers to the rate at which an imaging device displays consecutive images called frames. An image frame of the depth profile can provide a cross-sectional image of the epithelial tissue. The image frame may be a quadrilateral with any suitable dimensions. An image frame may be rectangular, in some cases with equal sides (e.g., square), for example depicting a 200 μm by 200 μm cross-section of the epithelial tissue. The image frame may depict a cross-section of the epithelial tissue having dimensions of about 50 μm by 50 μm, 100 μm by 100 μm, 150 μm by 150 μm, 200 μm by 200 μm, 250 μm by 250 μm, 300 μm by 300 μm, or greater. In some cases, the image frame may not have equal sides.

The disease identified may be epithelial cancer. An epithelial cancer is a skin cancer including, but not limited to, non-melanoma skin cancers, such as basal cell carcinoma (BCC) and squamous cell carcinoma (SCC), and melanoma skin cancers.

Methods disclosed herein for identifying a disease in an epithelial tissue of a subject can be used during and/or for the treatment of the disease, for example during Mohs surgery to treat skin cancer. In some cases, identifying a disease, for example a skin cancer, in an epithelial tissue of a subject can be performed in the absence of removing the epithelial tissue from the subject. This may advantageously prevent pain and discomfort to the subject, and can expedite detection and/or identification of the disease. The location of the disease may be detected in a non-invasive manner, which can enable a user such as a healthcare professional (e.g., surgeon, physician, nurse or other practitioner) to determine the location and/or boundary of the diseased area prior to surgery. Identifying a disease in an epithelial tissue of a subject, in some cases, can be performed without penetrating the epithelial tissue of the subject, for example by a needle.

Figure 2:
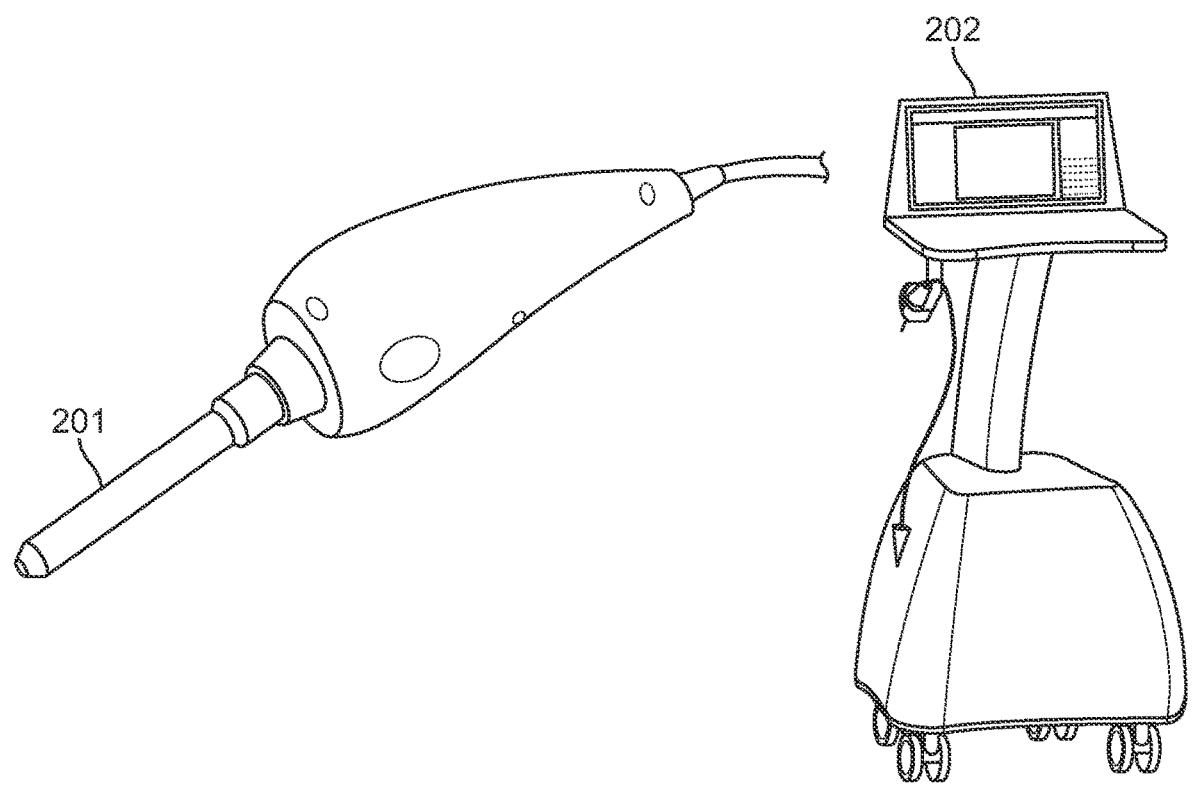
FIG. 2 provides an illustration of an apparatus that may be used to generate a depth profile of a tissue for identifying a disease.
Figure 3A:
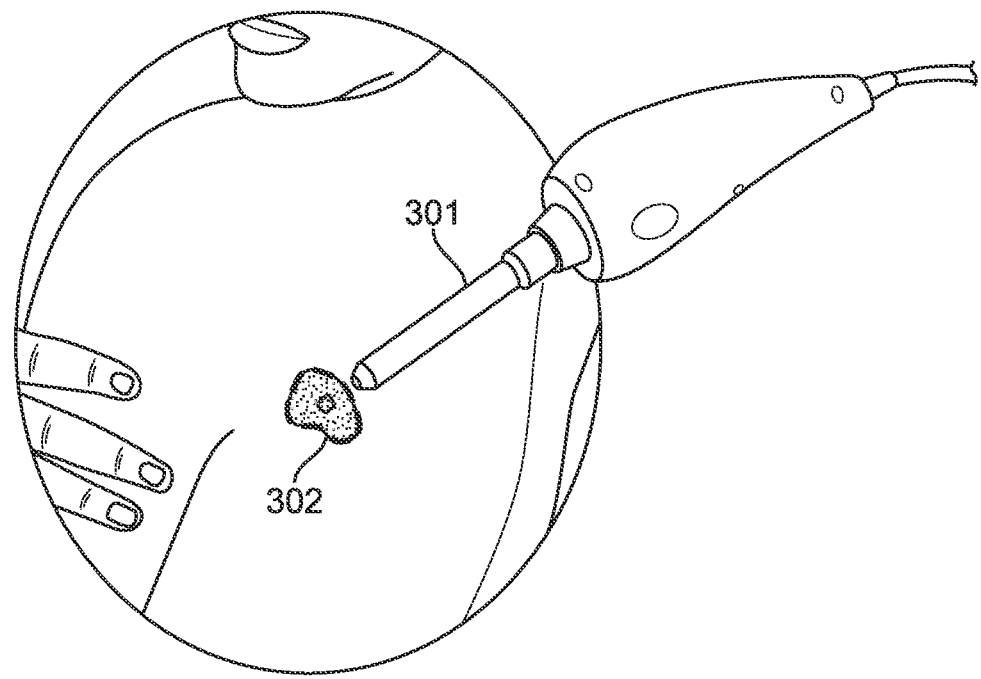
FIGS. 3A and 3B show a method for identifying a disease in an epithelial tissue.
Figure 3B:
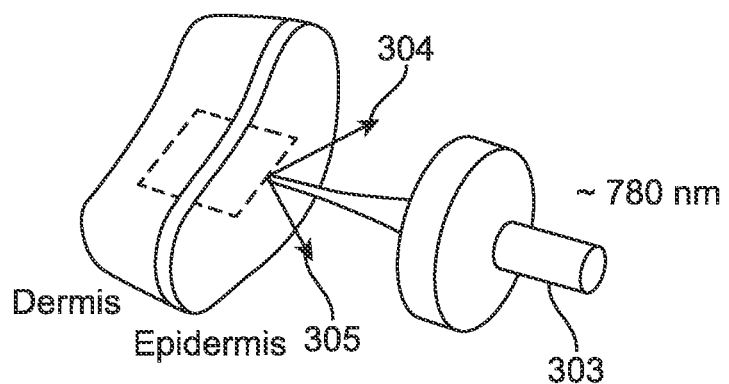
Figure 4:
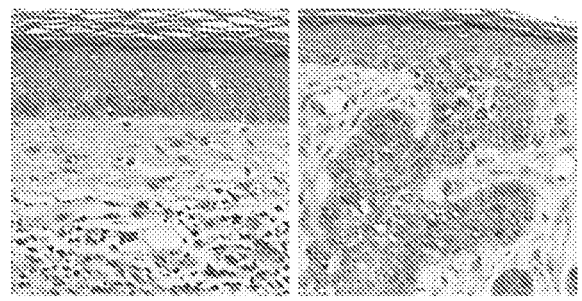
FIG. 4 shows two possible histological results in peripheral margin assessment (e.g., healthy and cancerous)

FIG. 2 provides an illustration of an apparatus that may be used to generate a depth profile for identifying a disease in an epithelial tissue. An apparatus that may be used for generating a depth profile may comprise an optical probe 201 and a portable cart with an ultrafast pulse laser 202. In an exemplary method as shown in FIGS. 3A and 3B, an optical probe 301 transmits pulses of a single beam of light from a light source, such as an ultrafast pulse laser on a portable cart, towards a surface of an epithelial tissue 302, such as a region suspected of having a disease. Pulses of a single beam of light 303, for example pulses of light having a wavelength centered at about 780 nm as shown in FIG. 3B, upon contacting the epithelial tissue 302, may generate signals such as autofluorescence signals 304 and second harmonic generation signals 305 that relate to an intrinsic property of the epithelial tissue. FIG. 4 shows exemplary depth profiles, healthy 401 and cancerous 402, that may be generated from signals relating to an intrinsic property of the skin tissue. These depth profiles may be used to identify tumor edges and facilitate rapid tumor removal. The depth profile can be provided on a display, such as the display of a mobile computing device, for example a phone or tablet, and evaluated by a surgeon to determine the location of the disease.

Figure 5:
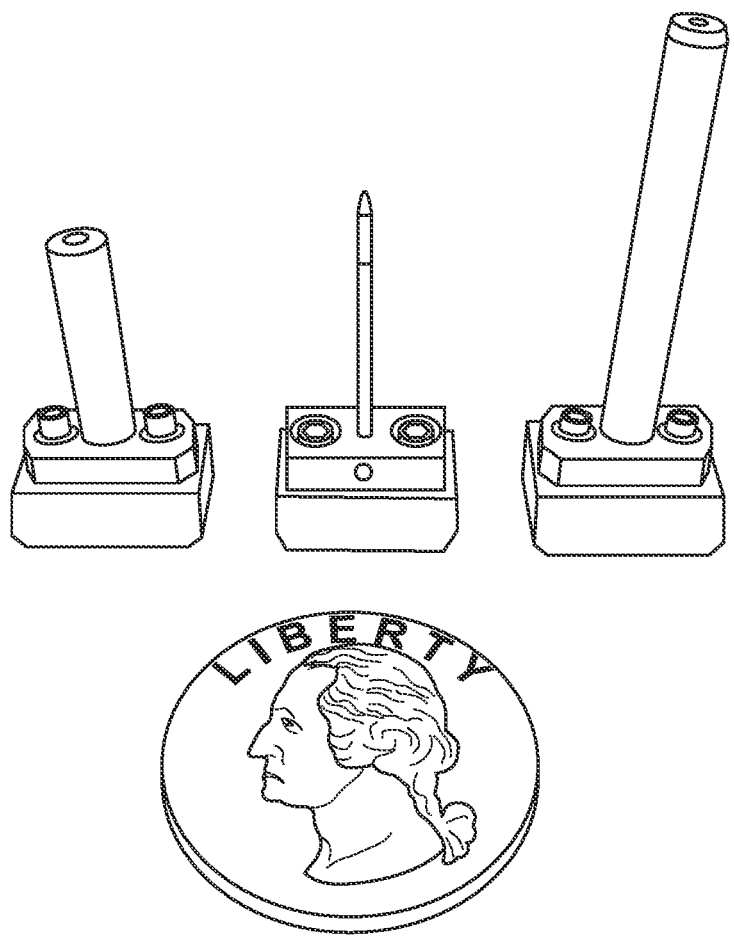
FIG. 5 shows several optical probes.

An optical probe may comprise optical elements that make direct contact with the tissue to image cellular structures. Multiple refractive lenses, such as relay lenses, collimating lenses, and field lenses, may be used to focus the ultrafast pulses of light from a light source to a small spot within the epithelial tissue. The small spot of focused light can, upon contacting the epithelial tissue, generate endogenous tissue signals, such as second harmonic generation, 2-photon autofluorescence, third harmonic generation, coherent anti-stokes Raman spectroscopy, or other nonlinear multiphoton generated signals. The probe may also transfer the scanning pattern generated by optical elements such as mirrors and translating lenses to a movement of the focal spot within the tissue to scan the focus through the structures and generate a point by point image of the tissue. The probe may comprise multiple lenses to minimize aberrations, optimize the linear mapping of the focal scanning, and maximize resolution and field of view. FIG. 5 shows several optical probes compatible with the methods described herein. An optical probe may be connected with other modules or subgroups (e.g., a scanning module and one or more collection modules) to form a handheld and portable imaging device, enabling a healthcare professional (e.g., surgeon, physician, nurse, or other practitioner) to identify the disease at the bedside of a subject.

The pulses of the single beam of light may be ultrashort pulses of light. Ultrashort pulses of light can be emitted from an ultrashort pulse laser (herein also referred to as an "ultrafast pulse laser"). Ultrashort pulses of light can have high peak intensities leading to nonlinear interactions in various materials. Ultrashort pulses of light generally refer to light having a full width of half maximum (FWHM) on the order of femtoseconds or picoseconds. In some examples, an ultrashort pulse of light has a FWHM of at least about 1 femtosecond, 10 femtoseconds, 100 femtoseconds, 1 picosecond, 100 picoseconds, or 1,000 picoseconds. Ultrashort pulses of light can be characterized by several parameters including pulse duration, pulse repetition rate, and average power. Pulse duration generally refers to the FWHM of the optical power versus time. Pulse repetition rate generally refers to the frequency of the pulses or the number of pulses per second. Non-limiting examples of ultrashort pulse laser technologies include Ti:Sapphire lasers, mode-locked diode-pumped lasers, mode-locked fiber lasers, and mode-locked dye lasers. A Ti:Sapphire laser is a tunable laser using a crystal of sapphire ($Al_2O_3$) that is doped with titanium ions as a lasing medium (e.g., the active laser medium which is the source of optical gain within a laser). Lasers, for example diode-pumped laser, fiber lasers, and dye lasers, can be mode-locked by active mode locking or passive mode locking, to obtain ultrashort pulses. A diode-pumped laser is a solid-state laser in which the gain medium comprises a laser crystal or bulk piece of glass (e.g., ytterbium crystal, ytterbium glass, and chromium-doped laser crystals). Although the pulse durations may not be as short as those possible with Ti:Sapphire lasers, diode-pumped ultrafast lasers can cover wide parameter regions in terms of pulse duration, pulse repetition rate, and average power. Fiber lasers based on glass fibers doped with rare-earth elements such as erbium, ytterbium, neodymium, dysprosium, praseodymium, thulium, or combinations thereof can also be used. In some cases, a dye laser comprising an organic dye, such as rhodamine, fluorescein, coumarin, stilbene, umbelliferone, tetracene, malachite green, or others, as the lasing medium, in some cases as a liquid solution, can be used.

The light source providing ultrashort pulses of light can be a wavelength-tunable, ultrashort-pulsed Ti:Sapphire laser. A Ti:Sapphire laser can be a mode-locked oscillator, a chirped-pulse amplifier, or a tunable continuous wave laser. A mode-locked oscillator can generate ultrashort pulses with a duration between about a few picoseconds and about 10 femtoseconds, and in cases about 5 femtoseconds. The pulse repetition frequency can be about 70 to 90 megahertz (MHz). The term 'chirped-pulse' generally refers to a special construction that can prevent the pulse from damaging the components in the laser. In a 'chirped-pulse' laser, the pulse can be stretched in time so that the energy is not all located at the same point in time and space, preventing damage to the optics in the amplifier. The pulse can then be optically amplified and recompressed in time to form a short, localized pulse. These devices can generate ultrashort, ultra-high-intensity pulses with a duration of about 20 femtoseconds to about 100 femtoseconds.

Ultrashort pulses of light can be produced by gain switching. In gain switching, the laser gain medium is pumped with, e.g., another laser. Gain switching can be applied to various types of lasers including gas lasers (e.g. transversely excited atmospheric (TEA) carbon dioxide lasers).

Adjusting the pulse repetition rate can, in some cases, be more easily accomplished with gain-switched lasers than mode-locked lasers, as gain-switching can be controlled with an electronic driver without changing the laser resonator setup. In some cases, a pulsed laser can be used for optically pumping a gain-switched laser. For example, nitrogen ultraviolet lasers or excimer lasers can be used for pulsed pumping of dye lasers. In some cases, Q-switching can be used to produce ultrafast pulses of light.

An ultra-fast pulse laser may produce pulses of light with pulse durations less than 500 femtoseconds, 450 femtoseconds, 400 femtoseconds, 350 femtoseconds, 300 femtoseconds, 250 femtoseconds, 200 femtoseconds, 150 femtoseconds, 100 femtoseconds, or shorter. In some cases, the pulse duration is about 150 femtoseconds. The pulse repetition frequency of an ultra-fast pulse laser can be at least 10 MHz, 20 MHz, 30 MHz, 40 MHz, 50 MHz, 60 MHz, 70 MHz, 80 MHz, 90 MHz, 100 MHz, or greater. In some cases, the pulse repetition frequency is about 80 MHz Tissue and cellular structures in epithelial tissue can interact with the pulses of the single beam of light in a wavelength dependent manner and generate signals that relate to intrinsic properties of the epithelial tissue. The signals generated can be used to evaluate the cancerous state of the tissue, such as skin tissue. The subset of the signals generated and collected can include at least one of second harmonic generation (SHG) signals, third harmonic generation (THG) signals, polarized light signals, and autofluorescence signals. Higher harmonic generation microscopy (HHGM) (e.g., second harmonic generation and third harmonic generation), based on nonlinear multiphoton excitation, can be used to examine cellular structures in live and fixed tissues. SHG generally refers to a nonlinear optical process in which photons with about the same frequency interact with a nonlinear material and effectively "combine" to generate new photons with about twice the energy, and therefore about twice the frequency and about half ($½$) the wavelength of the initial photons. Similarly, THG generally refers to a nonlinear optical process in which photons with about the same frequency interact with a nonlinear material and effectively "combine" to generate new photons with about three times the energy, and therefore about three times the frequency and about one-third ($⅓$) the wavelength of the initial photons. Second and third harmonic generation (SHG, THG) of ordered endogenous molecules, such as but not limited to collagen, microtubules, and muscle myosin, can be obtained without the use of exogenous labels and provide detailed, real-time optical reconstruction of molecules including fibrillar collagen, myosin, microtubules as well as other cellular information such as membrane potential and cell depolarization. The ordering and organization of proteins and molecules in a tissue, for example collagen type I and II, myosin, and microtubules, can generate, upon interacting with light, signals that can be used to evaluate the cancerous state of a tissue. SHG signals can be used to detect changes such as changes in collagen fibril/fiber structure that may occur in diseases including cancer, fibrosis, and connective tissue disorders. Various biological structures can produce SHG signals. In some cases, the labeling of molecules with exogenous probes and contrast enhancing agents, which can alter the way a biological system functions, may not be necessary. In some cases, methods herein for identifying a disease in an epithelial tissue of a subject are performed in the absence of administering a contrast enhancing agent to the subject.

Another type of signal that can be generated and collected for use in determining a disease in an epithelial tissue is autofluorescence. Autofluorescence generally refers to light that is naturally emitted by certain biological molecules, such as proteins, small molecules and/or biological structures. Epithelial tissue and cells can comprise various autofluorescent proteins and compounds. Well-defined wavelengths can be absorbed by chromophores, such as endogenous molecules, proteins, water, and adipose that are naturally present in cells and tissue. Non-limiting examples of autofluorescent fluorophores that can be found in tissues include polypeptides and proteins comprising aromatic amino acids such as tryptophan, tyrosine, and phenylalanine which can emit in the UV range and vitamin derivatives which can emit at wavelengths in a range of about 400 nm to 650 nm, including retinol, riboflavin, the nicotinamide ring of NAD(P)H derived from niacin, and the pyridolamine crosslinks found in elastin and some collagens, which are based on pyridoxine (vitamin B6).

In some cases, an optical probe can be used to transmit pulses of polarized light towards a surface of epithelial tissue. Polarized light can be used to generate contrast in biological specimens from birefringent molecules such as cellulose and starch. Polarized light can be used to examine parameters such as cell size and refractive index. Refractive index can provide information, such as information regarding the composition of cells and organizational structure of cells, for example cells in a tissue sample.

Cancer may significantly alter tissue organization. Certain parameters, such as cell size and refractive index, can be used to detect and diagnose precancerous changes in epithelial tissue. In some cases, the pulses of the single beam of light comprise polarized light. The plane of polarization can be rotated to produce polarized light with varying planes of polarization. The plane of polarization can be rotated by at least about 10°, 20°, 30°, 40°, or 45°. Rotation of polarized light can be used to highlight various structures in the epithelial tissue. As an alternative, the pulses of the single beam of light comprise unpolarized light.

A wavelength of the pulses of the single beam of light can be at least about 400 nanometers (nm), 450 nm, 500 nm, 550 nm, 600 nm, 650 nm, 700 nm, 750 nm, 800 nm, 850 nm, 900 nm, 950 nm or longer. In some cases, the wavelength of the pulses of light is between about 700 nm and 900 nm, between about 725 nm and 875 nm, between about 750 nm and 850 nm, or between about 775 nm and 825 nm. Multiple wavelengths may also be used. When multiple wavelengths of light are used, the wavelengths can be centered at about 400 nm, 450 nm, 500 nm, 550 nm, 600 nm, 650 nm, 700 nm, 750 nm, 800 nm, 850 nm, 900 nm, 950 nm or longer with a bandwidth of at least about 10 nm, 20 nm, 30 nm, 40 nm, 50 nm, 75 nm, 100 nm, 125 nm, 150 nm, 175 nm, 200 nm, 225 nm, 250 nm, 275 nm, 300 nm or longer. For example, the wavelengths can be centered at about 780 nm with a bandwidth of about 50 nm (e.g. about ((780−(50/2))=755 nm) to about ((780+(50/2))=805 nm)).

The subset of signals generated as a result of the pulses of light can be collected by a photodetector, such as a photomultiplier tube (PMT), photodiode, charge-coupled device (CCD), charge-injection device (CID), and complementary-metal-oxide-semiconductor detector (CMOS). Optical filters can be used to collect the subset of signals, for example light corresponding to autofluorescence signals, second harmonic generation signals, and third harmonic generation signals. Optical filters can selectively transmit light of different wavelengths and may comprise a pane glass or plastic device in the optical path. Optical filters may be bandpass filters, which reflect light that falls out of the bandpass range. Bandpass filters can reflect at least about 10%, 20%, 30%, 40%, 50%, 60%, 70%, 80%, 90% or more of light that falls outside of the bandpass range. In some cases, optical filters can be used to collect the subset of signals, such as second harmonic generation signals, third harmonic generation signals, signals from polarized light, and autofluorescence signals.

In some cases, these signals may be collected in the presence of ambient light. Ambient light can refer to normal room lighting, such as provided by various types of electric lighting sources including incandescent light bulbs or lamps, halogen lamps, gas-discharge lamps, fluorescent lamps, light-emitting diode (LED) lamps, and carbon arc lamps, in a medical examination room or an operating area where a surgical procedure is performed.

The collected signals can be processed by a programmed computer processor to generate a depth profile. The signals can be transmitted wirelessly to a programmed computer processor. As an alternative, the signals may be transmitted through a wired connection to a programmed computer processor. The signals or a subset of the signals relating to an intrinsic property of the epithelial tissue can be used to generate a depth profile with the aid of a programmed computer processor. The collected signals and/or generated depth profile can be stored electronically. In some cases, the signals and/or depth profile are stored until deleted by a user, such as a surgeon, physician, nurse or other healthcare practitioner. When used for diagnosis and/or treatment, the depth profile may be provided to a user in real-time. A depth profile provided in real-time can be used as a pre-surgical image to identify the boundary of a disease, for example skin cancer. The depth profile can provide a visualization of the various layers of epithelial tissue, such as skin tissue, including the epidermis, the dermis, and/or the hypodermis. The depth profile can extend at least below the stratum corneum, the stratum lucidum, the stratum granulosum, the stratum spinosum or the squamous cell layer, and/or the basal cell layer. In some cases, the depth profile extends at least 250 μm, 300 μm, 350 μm, 400 μm, 450 μm, 500 μm, 550 μm, 600 μm, 650 μm, 700 μm, 750 μm, or farther below the surface of the epithelial tissue. In some cases, the depth profile extends between about 100 μm and 1 mm, between about 200 μm and 900 μm, between about 300 μm and 800 μm, between about 400 μm and 700 μm, or between about 500 μm and 600 μm below the surface of the epithelial tissue.

Figure 6A:
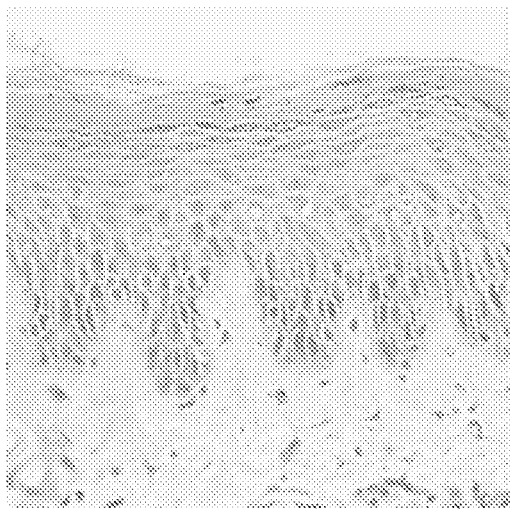
FIG. 6A shows a sample from classical pathology analysis and a real-time, polychromatic depth profile.
Figure 6A:
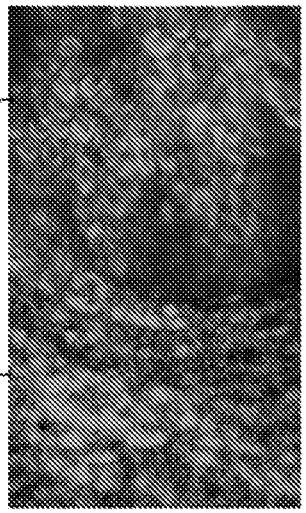
Figure 6B:
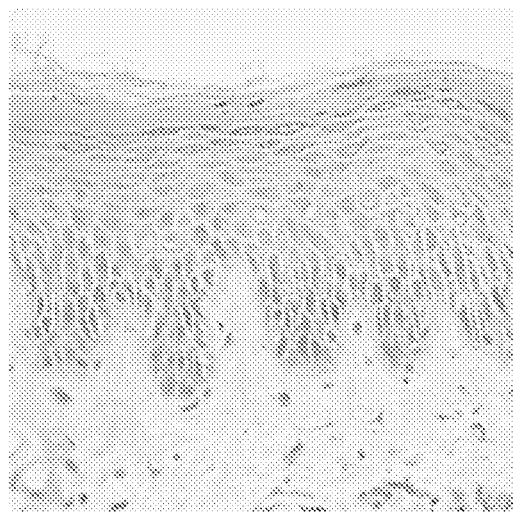
FIG. 6B shows a sample from classical pathology analysis and a real-time, monochromatic depth profile.
Figure 6B:

The depth profile can comprise a monochromatic image displaying colors derived from a single base hue. As an alternative, the depth profile can comprise a polychromatic image displaying more than one color. In a polychromatic image, multiple colors can be used to highlight different elements of a cell, such as a cell nucleus and cytoplasm. The contrast can be adjusted in real-time to provide and/or enhance structure specific contrast. The contrast can be adjusted by a user (e.g. surgeon, physician, nurse or other healthcare practitioner) or a programmed computer processor may automatically optimize the contrast in real-time. In a polychromatic image, each color may be used to represent a specific subset of the signals collected, such as second harmonic generation signals, third harmonic generation signals, signals resulting from polarized light, and autofluorescence signals. The colors of a polychromatic depth profile can be customized to reflect the image patterns a surgeon and/or pathologist may typically see when using standard histopathology. A pathologist may more easily interpret the results of a depth profile when the depth profile is displayed similar to how a traditional histological sample, for example a sample stained with hematoxylin and eosin, may be seen. FIGS. 6A and 6B show samples from classical pathology analysis and real-time depth profiles provided as a polychromatic image (FIG. 6A) and a monochromatic image (FIG. 6B). The polychromatic image of FIG. 6A depicts a first subset of signals 601 in red and a second subset of signals 602 in green. The monochromatic image of FIG. 6B depicts a first subset of signals 603 in dark purple and a second subset of signals 604 in light purple.

To generate a depth profile, signals from a plurality of focal planes can be collected. The plurality of different focal planes can be obtained by changing a relative position of a mobile lens with respect to the epithelial tissue. The mobile lens may be in optical communication with the optical probe. Changing the relative position of the mobile lens may comprise translating the mobile lens. The mobile lens can be translated at a cyclic rate to produce a frame rate of at least 1 frames per second (FPS), 2 FPS, 3 FPS, 4 FPS, 5 FPS, 10 FPS, or greater. The cyclic rate can be at least 0.5 Hz, 1 Hz, 2 Hz, 3 Hz, 4 Hz, 5 Hz or greater. As an alternative or in conjunction with a mobile lens, the plurality of different focal planes can be obtained by modulating a curvature of an electrically or electro-mechanically tunable lens that is in electrical or electro-mechanical communication with the optical probe. Tunable lenses can refer to optical elements whose optical characteristics, such as focal length and/or location of the optical axis, can be adjusted during use, for example by electronic control. Electrically-tunable lenses may contain a thin layer of a suitable electro-optical material (e.g., a material whose local effective index of refraction, or refractive index, changes as a function of the voltage applied across the material). An electrode or array of electrodes can be used to apply desired voltages to locally adjust the refractive index to the desired value. The electro-optical material may comprise liquid crystals. Voltage can be applied to modulate the axis of birefringence and the effective refractive index of an electro-optical material comprising liquid crystals. In some cases, polymer gels can be used. A tunable lens may comprise an electrode array that defines a grid of pixels in the liquid crystal, similar to pixel grids used in liquid-crystal displays. The refractive indices of the individual pixels may be electrically controlled to give a desired phase modulation profile, phase modulation profile referring to the distribution of the local phase shifts that are applied to light passing through the layer as the result of the locally-variable effective refractive index over the area of the electro-optical layer of the tunable lens.

The optical probe transmitting the pulses of light may be translated across the surface of the epithelial tissue so that a user can examine the entire region having the disease or suspected of having the disease. This may allow the user to assess the boundary and location of the disease. In some cases, a boundary that is indicative of the location of the disease, for example a skin cancer such as non-melanoma skin cancer, in the epithelial tissue of the subject can be outlined. The optical probe can comprise a marking tool, such as a marking tool comprising ink, to outline the boundary of the disease area. The marking tool can be a pen or other writing instrument comprising skin marking ink that is FDA approved, such as Genetian Violet Ink; prep resistant ink that can be used with aggressive skin prep such as for example CHG/isopropyl alcohol treatment; waterproof permanent ink; or ink that is easily removable such as with an alcohol. A pen can have a fine tip, an ultra-fine tip, or a broad tip. The marking tool can be a sterile pen. As an alternative, the marking tool may be a non-sterile pen.

Use of a depth profile generated by the methods disclosed herein can allow a user to distinguish healthy tissue from cancerous tissue and map out the boundary of the disease, e.g., cancer prior to surgery. The depth profile may be provided on a display in proximity to the surgeon and/or patient such that the user can evaluate in real-time the disease in the epithelial tissue and determine the location and/or boundary of the disease. A display can be a screen associated with any computing device, such as a computer, television, or a mobile computing device such as a phone or tablet. Methods herein for detecting a disease in an epithelial tissue of a subject may enable treatment of skin cancer with one surgery. By identifying the cancer and its location in the epithelial tissue, the cancer may be removed with loss of a minimal amount of healthy tissue.

In an aspect, a method for identifying a disease in an epithelial tissue of a subject may comprise using an optical probe to transmit pulses of light from a light source towards a surface of the epithelial tissue without penetrating the epithelial tissue of the subject. The pulses of light, upon contacting the epithelial tissue, may generate signals that relate to an intrinsic property of the epithelial tissue. The pulses of light can be directed to the epithelial tissue using a mobile lens at a plurality of different relative positions with respect to the epithelial tissue. Next, at least a subset of the signals generated from the pulses of light may be collected. The subset of the signals can be processed, for example with the aid of a programmed computer processor, to generate a profile of the epithelial tissue. The depth profile may be usable to identify the disease in the epithelial tissue of the subject. In some cases, the profile is a depth profile. The profile can be presented on a customizable display such that the information is provided in a manner that is familiar to the user.

The pulses of light can be pulses of a single beam of light. The pulses of a single beam of light can be ultrashort pulses of light as in other aspects described herein. The ultrashort pulses of light can come from a light source such as an ultrashort pulse laser or a gain switched laser. A photodetector may be used to collect the signals generated as a result of the pulses of light. The photodetector may be a PMT that is sensitive to the intensity of the signals collected. In some cases, the signals can exceed the detection capacity of the photodetector. The detection capacity of some photodetectors may be exceeded by ambient light. Signals that exceed the detection capacity of the photodetector can damage the photodetector. To prevent damage to the photodetector from ambient light, the optical probe in which a photodetector may be positioned can make a contact with the surface of the epithelial tissue so that a minimal amount of ambient light reaches the photodetector. The contact may be monitored such that when contact between the surface of the epithelial tissue and the optical probe is disrupted, a shutter positioned in front of the detector (e.g., relative to the path of light) can be activated and block incoming light. In some cases, the PMT comprises electrical interlocks and/or shutters. The electrical interlocks and/or shutters can protect the PMT when the photomultiplier compartment is exposed to ambient light by activating when contact between the surface of the epithelial tissue and the optical prove has been disrupted. By using activatable interlocks and/or shutters, signals can be collected in the presence of ambient light, thereby allowing a user to generate one or more real-time, pre-surgical depth profiles at the bedside of the patient.

In some cases, the optical probe is translatable across the surface of the epithelial tissue. The probe can be freely moved and operated on the surface of the skin tissue. Translating the optical probe across the surface of the epithelial tissue can allow a wide region of the epithelial tissue to be examined in real-time. An optical probe that can be translated may comprise a handheld and portable housing. This can allow a surgeon to examine in real-time the location of the disease, for example a cancer in skin tissue, at the bedside of a patient. The housing can have a footprint of at least about 0.1 $ft^2$, 0.2 $ft^2$, 0.3 $ft^2$, 0.4 $ft^2$, 0.5 $ft^2$, or 1 $ft^2$. As an alternative, the housing can have a footprint that is less than or equal to about 1 $ft^2$, 0.5 $ft^2$, 0.4 $ft^2$, 0.3 $ft^2$, 0.2 $ft^2$, or 0.1 $ft^2$. In an aspect, apparatuses for identifying a disease in an epithelial tissue of a subject consistent with the methods herein are provided. Apparatuses consistent with the methods herein may comprise any element of the subject methods including, but not limited to, an optical probe; one or more light sources such as an ultrashort pulse laser; one or more mobile or tunable lenses; one or more optical filters; one or more photodetectors; one or more computer processors; one or more marking tools; and combinations thereof.

An apparatus for identifying a disease in an epithelial tissue of a subject may comprise an optical probe. The optical probe may transmit pulses of a single beam of light from a light source towards a surface of the epithelial tissue. The pulses of a single beam of light, upon contacting the epithelial tissue, can then generate signals that relate to an intrinsic property of the epithelial tissue. The light source may comprise an ultra-fast pulse laser, such as a Ti:Sapphire laser. The ultra-fast pulse laser may generate pulse durations less than 500 femtoseconds, 400 femtoseconds, 300 femtoseconds, 200 femtoseconds, 100 femtoseconds, or less. The pulse repetition frequency of the ultrashort light pulses can be at least 10 MHz, 20 MHz, 30 MHz, 40 MHz, 50 MHz, 60 MHz, 70 MHz, 80 MHz, 90 MHz, 100 MHz, or greater.

The apparatus may comprise a mobile lens in optical communication with the optical probe. During use, the mobile lens may yield a plurality of different focal planes with respect to the epithelial tissue.

The mobile lens of an apparatus can be translated to yield the plurality of different focal planes. The mobile lens may be coupled to an actuator that translates the lens. The actuator may be controlled by a programmed computer processor. The actuator can be a linear actuator, such as a mechanical actuator, a hydraulic actuator, a pneumatic actuator, a piezoelectric actuator, an electro-mechanical actuator, a linear motor, or combinations thereof. Mechanical actuators can operate by converting rotary motion into linear motion, for example by a screw mechanism, a wheel and axle mechanism, and a cam mechanism. A hydraulic actuator can involve a hollow cylinder comprising a piston and an incompressible liquid. A pneumatic actuator may be similar to a hydraulic actuator but involves a compressed gas instead of a liquid. A piezoelectric actuator can comprise a material which can expand under the application of voltage. As a result, piezoelectric actuators can achieve extremely fine positioning resolution, but may also have a very short range of motion. In some cases, piezoelectric materials can exhibit hysteresis which may make it difficult to control their expansion in a repeatable manner. Electro-mechanical actuators are similar to mechanical actuators except that the control knob or handle is replaced with an electric motor.

In some cases, an electrically or electro-mechanically tunable lens that is in electrical or electro-mechanical communication with the optical probe may be used to yield the plurality of different focal planes. Modulating a curvature of the electrically or electro-mechanically tunable lens can yield a plurality of different focal planes with respect to the epithelial tissue. The curvature of the tunable lens may be modulated by applying current. The apparatus may also comprise a programmed computer processor to control the application of current.

An apparatus for identifying a disease in an epithelial tissue may comprise optical filters. Optical filters, as described elsewhere herein, can be used to collect one or more specific subsets of signals that relate to one or more intrinsic properties of the epithelial tissue. These optical filters can be coated glass or plastic elements which can selectively transmit certain wavelengths of light, such as autofluorescent wavelengths, and/or light with other specific attributes, such as polarized light. The optical filters can collect at least one of second harmonic generation (SHG) signals, third harmonic generation (THG) signals, polarized light signals, and autofluorescence signals.

A programmed computer processor, in addition to controlling the translation of a mobile lens or modulating the curvature of a tunable lens, can process signals to generate a depth profile. The depth profile can be used as a pre-surgical image to identify the boundary of a cancer in an epithelial tissue, such as non-melanoma skin cancer. The depth profile can be displayed on a screen. The screen can be any suitable screen associated with a computing device, such as a computer, television, or mobile device such as a phone or tablet. The depth profile may comprise a monochromatic image on a display or a polychromatic image on a display. A polychromatic image can highlight different structures in different colors, providing structure specific contrast, as described for various other aspects disclosed herein.

In some cases, the optical probe comprises a handheld housing, allowing a user to generate a depth profile at, for example, the bedside of a patient. The apparatus can further comprise a marking tool, such as a pen, so that a user can mark and indicate a boundary or a location of the disease in the epithelial tissue of the subject as he/she is evaluating the depth profile generated in real-time.

The apparatus may further comprise a sensor that detects a displacement between the optical probe and the surface of the epithelial tissue. This sensor can protect the photodetector, for example a PMT, from ambient light by activating a PMT shutter to prevent ambient light from reaching the PMT and damaging the PMT, if the ambient light exceeds the detection capacity of the PMT.

In some cases, the optical probe is not a confocal microscope.

Epithelial Cancer

Carcinoma generally refers to a type of cancer that develops from epithelial cells. A carcinoma can originate from a tissue that lines the inner or outer surfaces of the body, and generally arises from cells originating in the endodermal or ectodermal germ layer during embryogenesis. Carcinomas can be classified into groups based on histopathology. Non-limiting examples of these groups include adenocarcinoma, squamous cell carcinoma (SCC), adenosquamous carcinoma, anaplastic carcinoma, large cell carcinoma, and small cell carcinoma.

Carcinomas can be found in various regions of the body. Non-limiting examples of epithelial cancers include epithelial cancer of the ovary, colon, rectum, breast, prostate, pancreas, oral cavity, esophagus, lung, bladder, liver, uterus, skin, and brain. Carcinomas found in the oral cavities can comprise squamous-cell carcinoma. Breast cancers can comprise ductal carcinoma. Prostate cancer can comprise adenocarcinoma. Colon and rectum cancers can comprise adenocarcinoma and/or squamous cell carcinoma. Pancreatic cancer can comprise adenocarcinoma. Carcinomas can be named for their putative cell of origin (e.g. hepatocellular carcinoma and renal cell carcinoma). Carcinomas can also include rare subtypes of anaplastic, undifferentiated carcinoma such as spindle cell carcinoma, giant cell carcinoma, and sarcomatoid carcinoma.

Carcinomas can be staged, a process generally referring to combined physical and clinical examination, pathological review of cells and tissues, surgical techniques, laboratory tests, and imaging studies performed in a logical fashion to obtain information about the size of the abnormal growth or lesion and the extent of its invasion and metastasis. Carcinoma stage can be linked to the prognosis of the condition. Carcinomas are usually staged with Roman numerals (e.g. I, II, III, and IV). In some types of carcinomas, Stage 0 has been used to describe carcinoma in situ—that is, carcinomas that have not yet spread from the site of origin. Stage I and Stage II can be used to describe tumors that are small and/or have spread to local structures. Stage III can be used to describe tumors that have spread to regional lymph nodes, tissues, and/or organ structures. Stage IV can be used to describe tumors that may have already metastasized through the blood to distant sites, tissues, and/or organs. In more recent staging systems, sub-stages (a, b, c) may be used to better define groups of patients with similar prognosis or treatment options. The criteria for staging can differ based upon the organ system in which the tumor arises. For example, colon and bladder cancer staging system can rely on depth of invasion, while staging of breast carcinoma may depend more on the size of the tumor. In renal carcinoma, staging can be based on both the size of the tumor and the depth of the tumor invasion into the renal sinus. Stating carcinoma of the lung can be more complicated, taking into account a number of size and anatomic variables.

Grading of carcinomas generally refers to the use of criteria to quantify, either partially or completely, the degree of cellular and tissue maturity seen in the transformed cells relative to the appearance of the normal parent epithelial tissue from which the carcinoma derives. Grading of carcinoma can often be performed with a sample comprising suspected tumor tissue. A pathologist can examine the tissue sample using techniques including but not limited to staining, immunohistochemistry, and flow cytometry. Carcinomas can typically be classified as one of four grades. Grade 1 generally refers to a state in which the transformed cells closely resemble the normal parent epithelial tissue from which the carcinoma derives. Grade 2 generally refers to a state in which the transformed cells bear considerable resemblance to the normal parent epithelial tissue from which the carcinoma derives. Grade 3 generally refers to a state in which the transformed cells bear little resemblance to the normal parent epithelial tissue from which the carcinoma derives. Grade 4 generally refers to a state in which the transformed cells bear no significant resemblance to the normal parent epithelial tissue from which the carcinoma derives.

Carcinomas can be definitively diagnosed by examining tissue samples obtained using techniques including but not limited to biopsy, including needle aspiration, fine needle aspiration, core needle biopsy, vacuum assisted biopsy, large core biopsy, incisional biopsy, excisional biopsy, punch biopsy, shave biopsy, or skin biopsy. The tissue samples can be prepared for histopathologic or cytolopathologic analysis and examined, for example with a microscope, to identify molecular, cellular, and/or tissue architectural characteristics of the epithelial cells in the tissue sample. Histopathologic analysis can comprise the use of stains and dyes to examine the cellular organization and arrangement of structural features in the tissue sample. Non-limiting examples of stains for histopathologic analysis include hematoxylin and eosin (H&E), safranin, Oil Red O, Congo red, Fast green FCF, and silver salts. Histopathologic samples can also be examined by radioactive techniques. In radioactive techniques, radio-labeled substances in a tissue sample can be detected by X-ray. Histopathologic examination may also comprise immunohistochemistry, a process in which antibodies, including but not limited to unlabeled antibodies and labeled antibodies, can be used to detect specific proteins, carbohydrates, and lipids. The location of the specific proteins, carbohydrates, and lipids can be determined by this process. In cases where the stain is a fluorescent molecule, the technique may be referred to as immunofluorescence. Gene profiling of a tissue sample may also be used in diagnosing cancer as an alternative or in addition to histopathologic examination. Although there may be statistical correlation between carcinoma grade and tumor prognosis for some tumor types, the strength of this association can be highly variable.

The selection of treatment options can depend on the stage, grade, and location of the carcinoma. Non-limiting examples of treatment options include surgical excision or resection of the tumor, Mohs surgery or Mohs micrograph surgery, radiotherapy, chemotherapy, curettage and electrodessication, photodynamic therapy, and laser treatment. Treatment can comprise excision, wherein the tumor is surgically removed, and in some cases, some skin around the tumor that appears tumor free is also removed. Mohs surgery is a specialized surgery that can be used to remove some skin cancers. In Mohs surgery, a surgeon can cut out the tumor plus a very small amount skin surrounding the tumor that appears normal. While the patient waits, the surgeon can use a microscope to examine the tissue that was removed, specifically looking for the presence of cancer. If necessary, the surgeon can continue to remove a small amount of tissue and examine it under the microscope. This may continue until the surgeon no longer detects cancer when examining the tissue under a microscope. Treatment can comprise radiotherapy, a treatment which involves the use of high-energy radiation to kill cancer cells. Another form of treatment can comprise chemotherapy, which involves the administration of chemotherapeutics. Chemotherapeutics can be administered systemically or locally. Non-limiting methods of systemic administration include enteral administration such as via pill, tablet, capsule, and drop and parenteral administration such as via intravenous injection and intra-arterial injection. Non-limiting methods of local administration include topical administration such as via a chemotherapeutic cream and local injection. Treatment may comprise curettage and electrodessication. First, a curette is used to remove tissue by scraping or scooping, and electricity is applied to destroy any remaining cancer cells. In some cases, treatment can comprise photodynamic therapy (PDT), a treatment which involves the use of light to remove some early skin cancers.

Skin Cancer

Skin cancer may be considered a common form of cancer, globally accounting for at least 40% of cases. Skin cancer can occur from abnormal growth of skin cells and may be classified as non-melanoma and melanoma. Non-melanoma skin cancer can be more common than melanoma skin cancer. Non-limiting examples of non-melanoma cancers include basal cell carcinoma (BCC), squamous cell carcinoma (SCC), angiosarcoma, cutaneous B-cell lymphoma, cutaneous T-cell lymphoma, dermatofibrosarcoma protuberans, Merkel cell carcinoma, and sebaceous gland carcinoma. Of non-melanoma skin cancers, about 80% may be basal-cell cancers and 20% may be squamous-cell cancers. BCC can be present on sun-exposed areas of the skin, such as the face, but may be easily treated with surgery or radiation. Melanoma, sometimes referred to as malignant melanoma, is a type of cancer that can develop from melanocytes which are pigment-containing cells. Melanoma can be more aggressive than BCC and SCC.

Treatment of cancer, for example skin cancer, can depend on the type of cancer, location of the cancer, and age of the patient. Prognosis can be affected by clinical and histological factors and by the anatomic location of the cancer. Non-melanoma skin cancer can usually be cured and treatment can generally comprise surgical removal but may also include radiation therapy, the application of topical medications such as fluorouracil, and combinations thereof. Melanoma treatment can comprise surgery, chemotherapy, radiation therapy, targeted therapy, and combinations thereof.

The removal of epithelial cancers in high-risk anatomical sites, for example in areas near the eyes, nose, and mouth, can involve precise microsurgical excision guided by histologic examination of each excision during surgery. Minimum damage to the surrounding normal tissue may be desired.

Mohs Micrographic Surgery (Mohs Surgery)

Treatment of epithelial cancer, such as skin cancer, may comprise Mohs micrographic surgery (herein also referred to as "Mohs surgery"). Mohs surgery can comprise the surgical removal of tissue and subsequent histopathological examination of the excised tissue. Histopathological examination can be performed on fresh tissue samples or fixed tissue samples to detect the presence of cancer in the tissue that was surgically removed or excised. Mohs surgery can allow surgeons to verify that all cancer cells have been removed at the time of surgery. This can increase the chance of removing all cancerous tissue and may reduce the need for additional treatments and/or additional surgery.

Figure 7A:
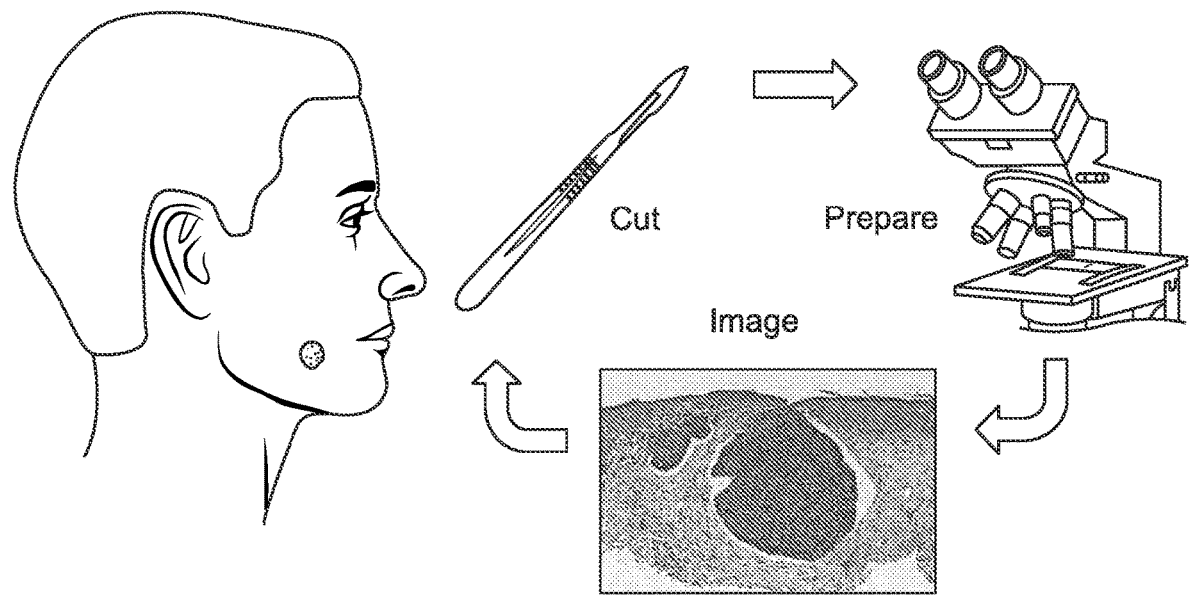
FIG. 7A shows an illustrative example of a Mohs micrographic surgery.

FIG. 7A shows an illustrative example of a Mohs surgery. After a putative tumor margin is identified, for example through visual examination, palpation, and gentle curettage by a surgeon or physician, a fresh tissue sample for histopathological examination is obtained, for example by an incision made with a scalpel in the area surrounding the putative tumor margin. At the time of incision, score marks can be placed in both the specimen and the surgical site for tissue orientation. The distance between the clinical border of the cancer and the incision can be variable, depending on the type of malignancy, size of the malignancy, and how well the malignancy is demarcated. In some cases, the surgical site can be anesthetized with a local anesthetic.

The tissue specimen can then be prepared for histopathological analysis. The specimen can be divided into smaller pieces based on the score marks and marked with ink to preserve tissue orientation. In some cases, a map correlating the surgical defect to the marked specimens can be generated. The tissue specimen can then be processed to produce thin frozen sections, for example via cryosectioning, of the entire peripheral margin of the specimen. The sections can be of variable thickness. The sections may be between 4 um and 8 um thick. The sections can be stained, for example with stains such as H&E and toluidine blue and/or immunohistochemical stains such as cytokeratin stains AE1/AE3, Per-EP4, MNF 116, CD34, low molecular-weight cytokeratin, and cytokeratin 7, and Mart-1. The tissue sections can then be examined for the presence of cancerous cells. If residual tumor is identified on the slides, the location can be marked on the map correlating the surgical defect to the marked specimen. This map can then be used to identify the corresponding region of the tumor involvement in the surgical site. This area can be subsequently removed for further tissue processing and examination, repeating the tissue preparation and staining process previously described. This process can be repeated until the peripheral and deep margins are histologically free of tumor cells.

To obtain fixed tissue samples for histological examination, a fixative, such as a mixture comprising zinc chloride, can be applied to the skin for a variable length of time, ranging from about 6 to 24 hours depending on the depth of tissue desired to be sampled. After fixation, samples can be surgically removed or excised and examined microscopically. Additional staining and processing generally may not be needed as the fixative applied to the skin can preserve tumor and cell histology. Anesthetic may not be needed during excision as the fixed tissue is dead and pain may not be felt. Depending of the result of microscopic examination of the excised sample, additional fixative can be applied to any remaining areas of tumor involvement for about an additional 6 to 24 hours and this process can be repeated until the tissue samples examined are histologically free of tumor. Preparation of fixed sections can take at least 1 to 2 days. Such time delays can result in an inability to sample large amounts of tissue and detect residual tumor margins in real-time. In some cases, tumor removal is incomplete and patients may undergo additional surgery, radiotherapy, chemotherapy, and combinations thereof.

Figure 7B:
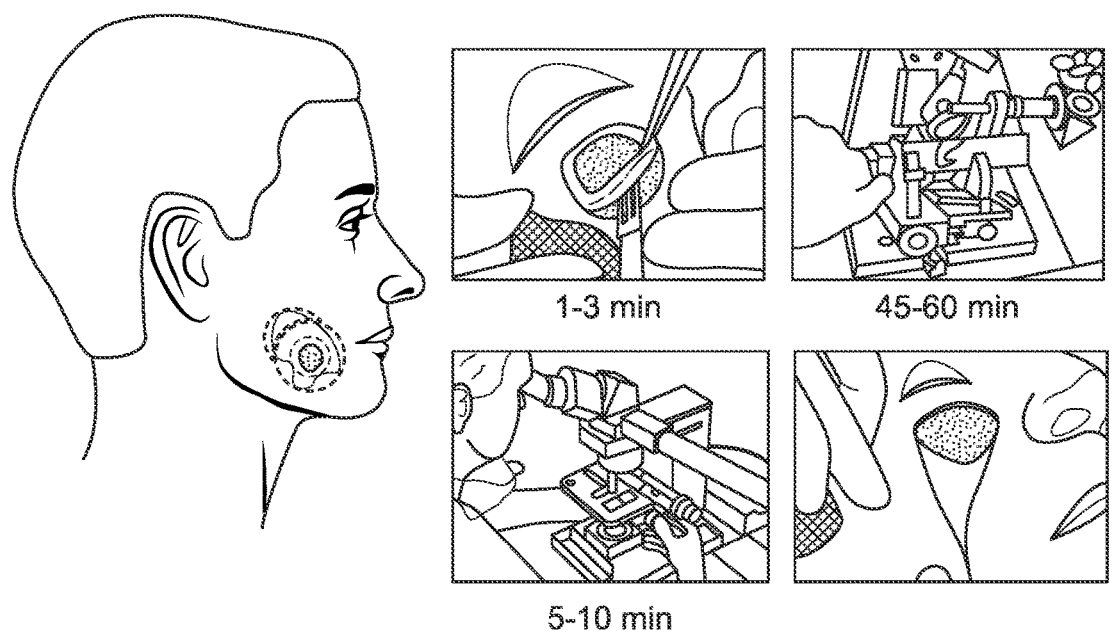
FIG. 7B shows several phases of a Mohs micrographic surgery and associated processing times for each phase.

A Mohs procedure may require between one to several excisions, depending on the size, shape and complexity of the lesion. The length of time for the entire process can be variable, depending on whether fresh tissue samples or fixed tissue samples are used. FIG. 7B shows several phases of a Mohs micrographic surgery using fresh tissue samples and associated processing times for each phase. The combined time of one round of tissue excision and sample analysis can take from about 0.1 hours to 4 hours, or 0.5 hours to 2 hours, depending on various factors including, but not limited to, the size of the tissue sample and the technique of the surgeons and/or technicians. The combined time may be less than or equal to 4 hours, 3 hours, 2 hours, 1 hour, 30 min, 10 min, 5 min, or 1 min.

A surgeon may determine if a sample appears healthy or cancerous. If the sample appears cancerous, an additional round of surgical excision and tissue examination may be performed. The sample may appear healthy, in some cases, and additional round of surgical excision may not be needed. In alternate scenarios, a surgeon may not be able to definitively determine if a sample is healthy or cancerous.

Mohs surgery can last for several hours, and the subject may be waiting with an open wound under local anesthesia for a majority of this procedure. This can be a slow and time-inefficient process that is uncomfortable for a patient.

Imaging System Set-Up

Figure 8:
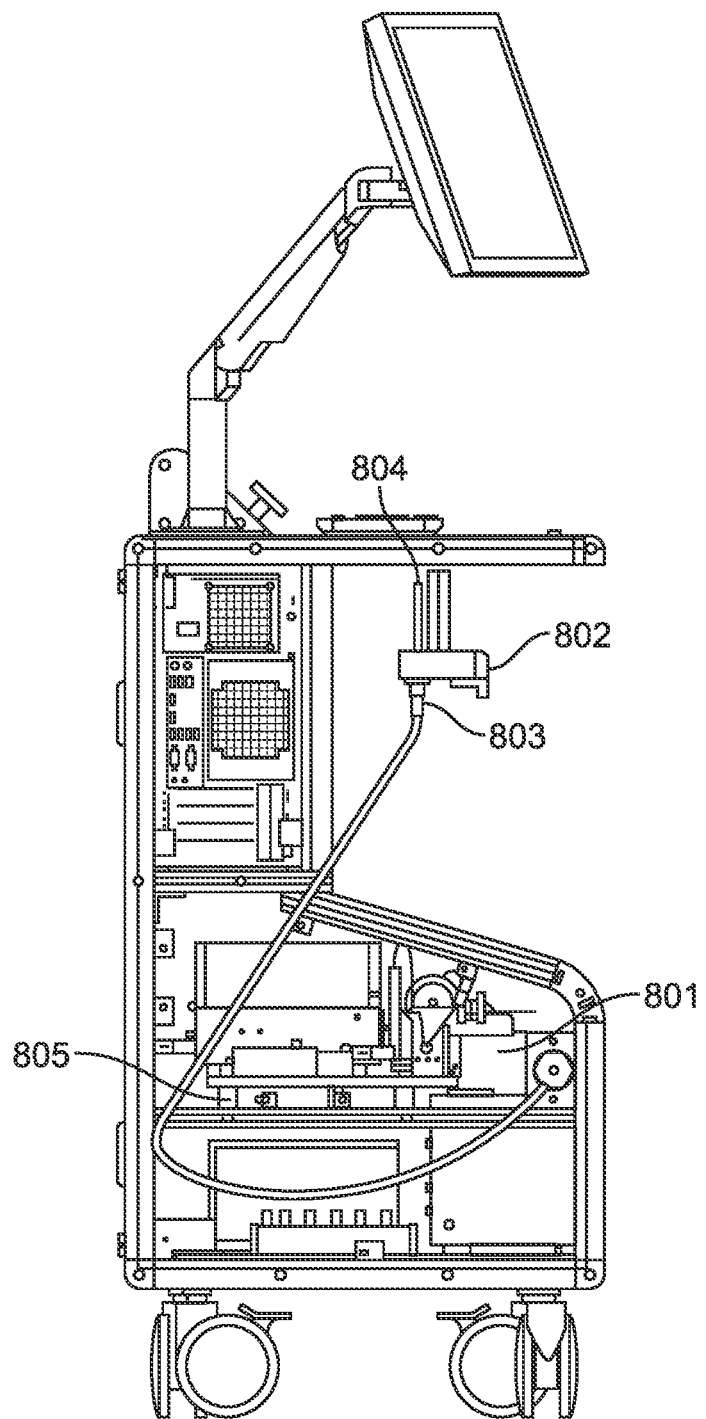
FIG. 8 shows an imaging system set-up for identifying a disease in an epithelial tissue.
Figure 9:
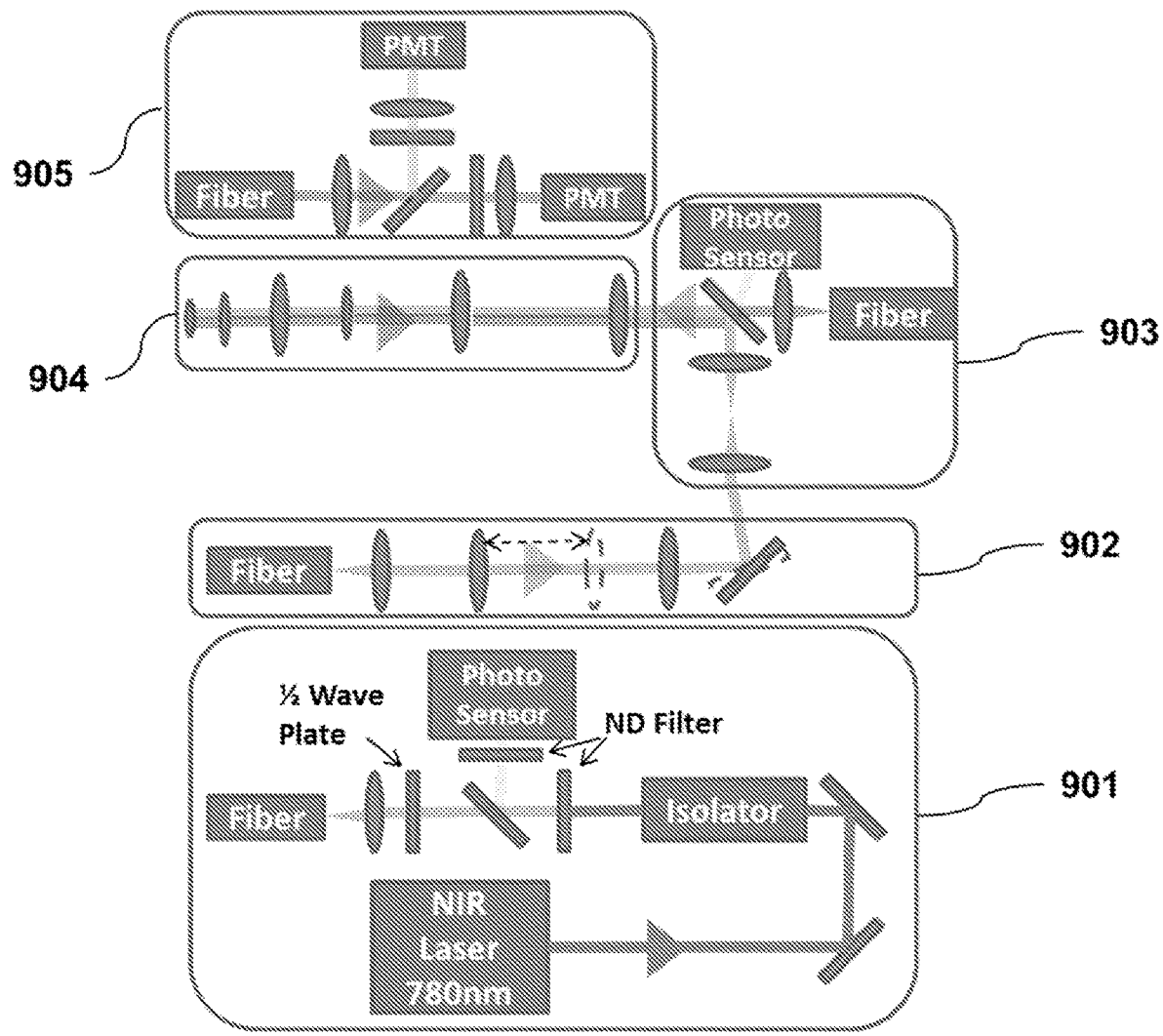
FIG. 9 shows schematically optical system modules of an imaging system.

With reference to FIG. 8, an imaging system set-up useful for performing the methods described herein may comprise a fiber launch module 801, a scanner module 802, a first collection module 803, an optical probe module 804, and a second collection module 805. A fiber launch module 801 may be used for light generation. A fiber launch module 801 may comprise a light source, such as an ultrafast pulse laser. Pulses of light from an ultrafast pulse laser can be delivered to a fiber optic, such as a single mode fiber having an air core, through a series of optical elements. The fiber optic can then deliver the pulses of light to the scanner module 802 which can create a scanning pattern. The light can then pass from the scanner module 802 to the first collection module 803 where it is further directed to the optical probe module 804, for example by a dichroic mirror. The optical probe module 804 may transmit the pulses of the single beam of light towards a surface of an epithelial tissue, such as a skin tissue. Upon contacting the epithelial tissue, signals related to intrinsic properties of the epithelial tissue, such as autofluorescence signals and second harmonic generation signals, may be generated. These signals can be collected and transmitted by the optical probe module 804 to the first collection module 803 and further to the second collection module 805. The second collection module may comprise one or more photomultiplier tubes for processing the signals related to intrinsic properties of the epithelial tissue. FIG. 9 schematically illustrates optical system modules such as a fiber launch module 901, a scanner module 902, a first collection module 903, an optical probe module 904, and a second collection module 905.

Figure 10A:
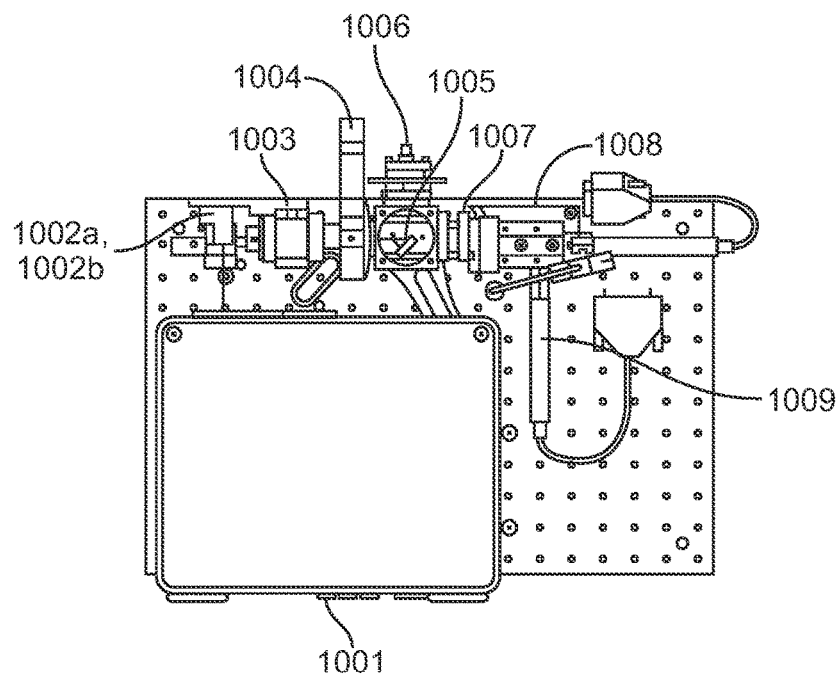
FIGS. 10A and 10B show the elements of an exemplary fiber launch module.
Figure 10B:
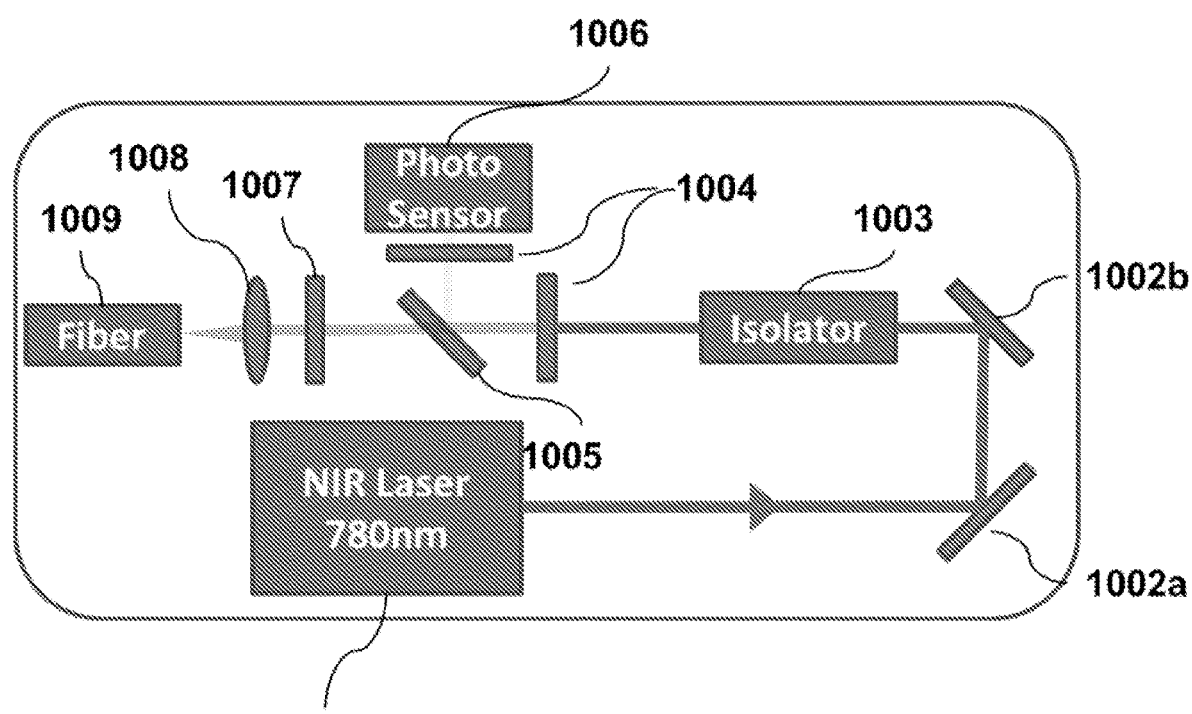

FIGS. 10A and 10B schematically illustrate the elements of an exemplary fiber launch module. A fiber launch module may comprise a light source such as a laser 1001; one or more steering mirrors 1002a and 1002b; an isolator 1003; one or more optical filters 1004; a beam sampler 1005; a photosensor 1006; a wave plate 1007; one or more lenses 1008; and fiber optic 1009. A laser 1001, such as a Toptica FemtoFiber Pro NIR 780 nm laser, may serve as the light generating source of the ultrafast pulses of light. One or more steering mirrors 1002a and 1002b may be used to direct the light pulses, for example, towards other elements of the fiber launch module. An isolator 1003, such as an EOT 33 dB Optical Isolator, may be included to rotate the pulses of light, for example, rotating pulses of polarized light. One or more optical filters 1004, such as continually variable reflective neutral density (ND) filters, can be used to reduce or modify the intensity of the light from the light source. A beam sampler 1005 may divert a portion of the light towards a photosensor 1006, such as an indium gallium arsenide (InGaAs) photodiode. By diverting a portion of the light towards a photosensor 1006, the light pulses can be monitored for optical degradation or instability, such as fluctuations in power. A wave plate 1007, such as a multi-order half wave plate, may further be provided to change the polarization state of light. One or more lenses 1008 may be used direct the light to a fiber optic 1009, such as a single mode fiber having an air core, which can transmit the pulses of light to a scanner module.

Figure 11A:
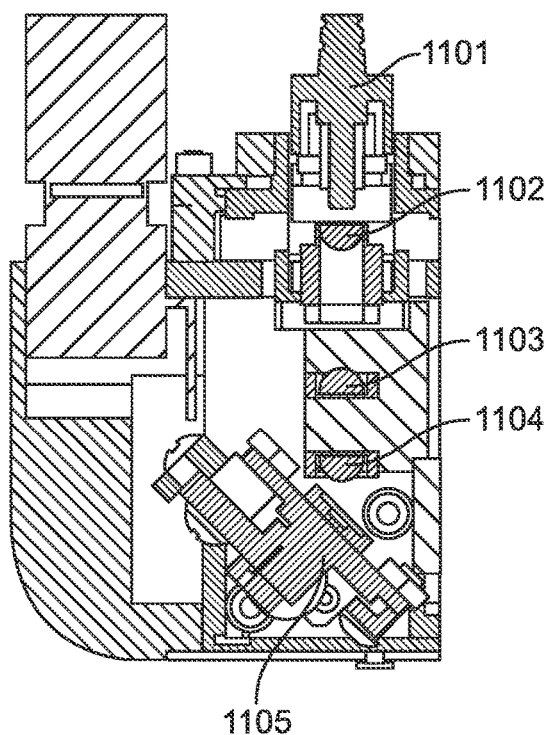
FIGS. 11A and 11B show the elements of an exemplary scanner module.
Figure 11B:
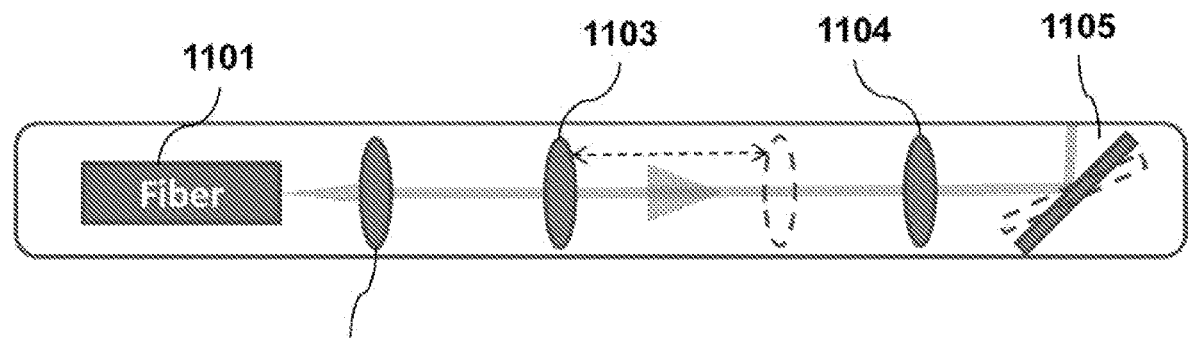

FIGS. 11A and 11B schematically illustrate an exemplary scanner module. A scanner module may comprise a fiber optic 1101; one or more lenses 1102, 1003, and 1104; and one or more mirrors 1105. The fiber optic of the fiber launch module and the fiber optic of the scanner module may be the same fiber optic, and the fiber optic may transmit light from the fiber launch module to the scanner module. The light may be collimated by a lens 1102, such as a collimating lens. The focal plane of the light may be changed using a pair of lenses, such as a focusing lens which is mobile 1103 and a focusing lens which is stationary 1104. The focused light may then be directed to a microelectromechanical systems (MEMS) mirror 1105 which directs the light towards a first collection module.

Figure 12A:
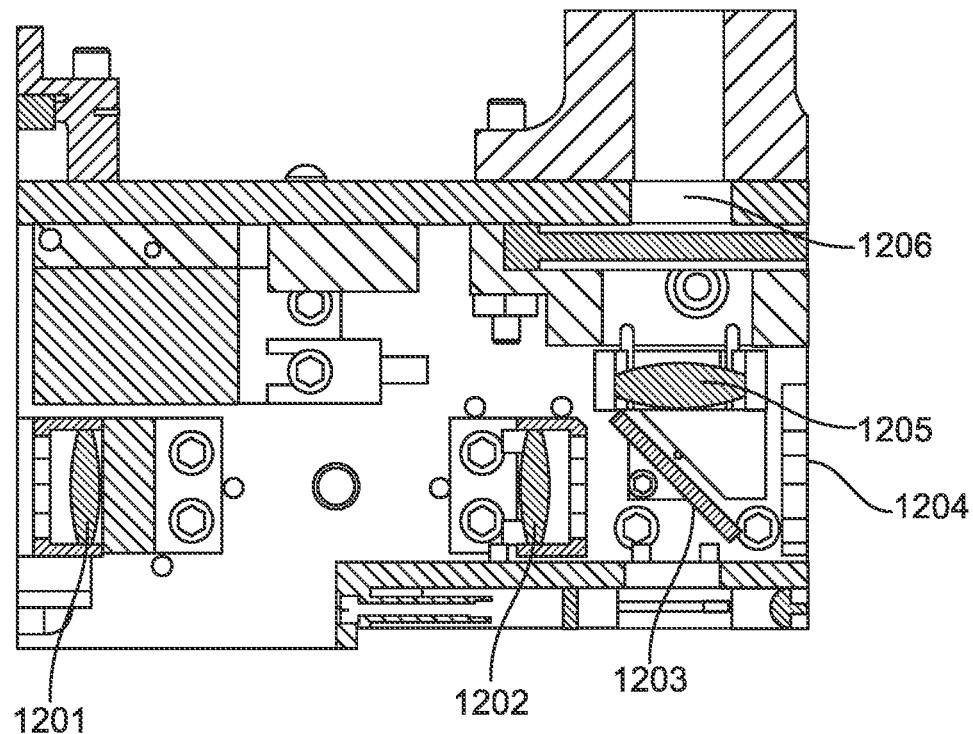
FIGS. 12A and 12B show the elements of an exemplary first collection module.
Figure 12B:
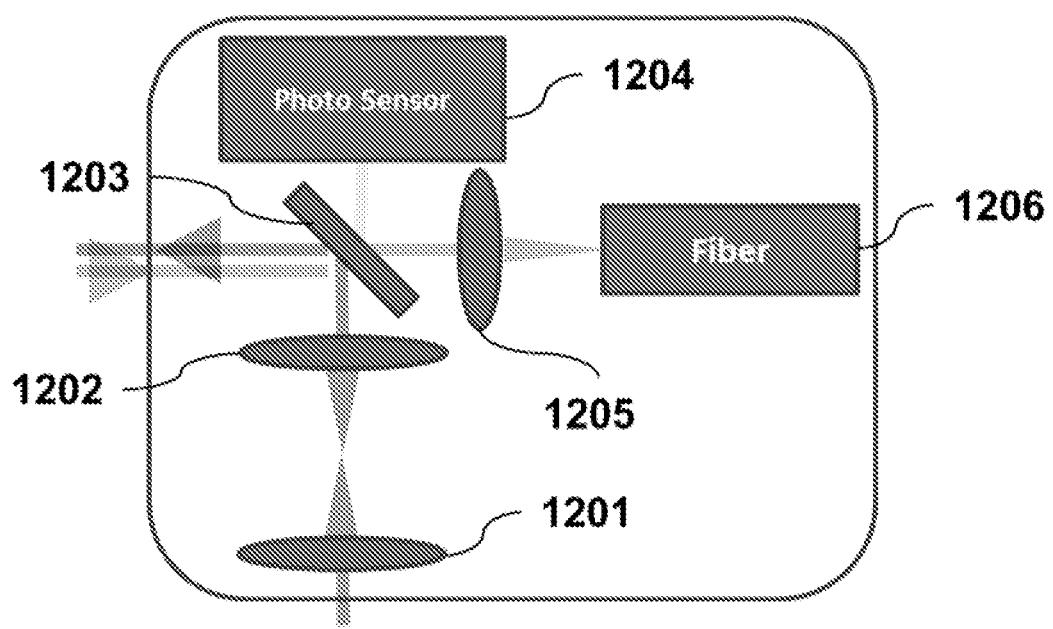

FIGS. 12A and 12B schematically illustrate an exemplary first collection module. A first collection module may comprise one or more relay lens 1201 and 1202; a dichroic mirror 1203; a photosensor 1204; a lens 1205; and a fiber optic 1206. Pulses of light received from a scanner module may be transmitted by relay lens 1201 and 1202 to a dichroic mirror 1203. The dichroic mirror 1203 may transmit some of the light to a photosensor 1204. The light transmitted to the photodetector can be used to monitor properties of the transmitted light. The light that is not transmitted to the photodetector 1204 can be diverted by the dichroic mirror to an optical probe module, which can direct the light towards a surface of the epithelial tissue. In addition to diverting light to the optical probe module, the dichroic mirror may also serve to transmit collected signals from the optical probe module towards a second collection module. The collected signals may be transmitted by the lens 1205 to a fiber optic 1206, such as a liquid light guide, which transmits the light to a second collection module. A light guide may be made of any optical grade material such as acrylic resin, polycarbonate, epoxies, liquids, and glass.

Figure 13A:
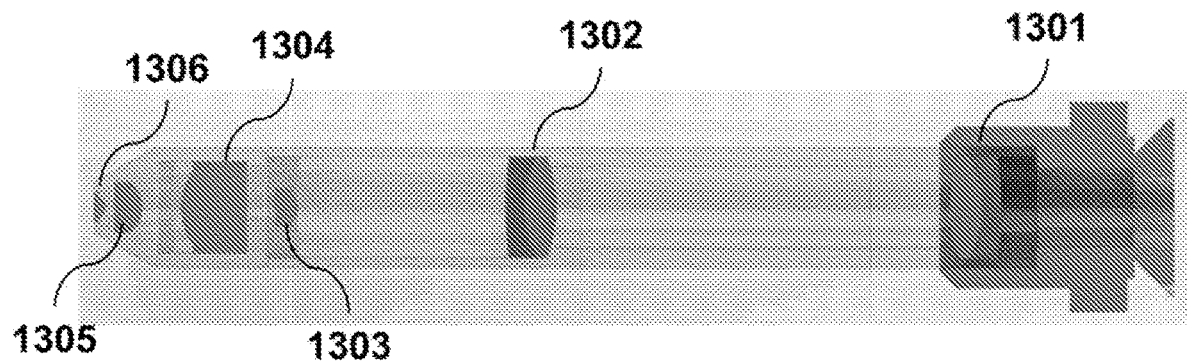
FIGS. 13A and 13B show the elements of an exemplary optical probe module.
Figure 13B:
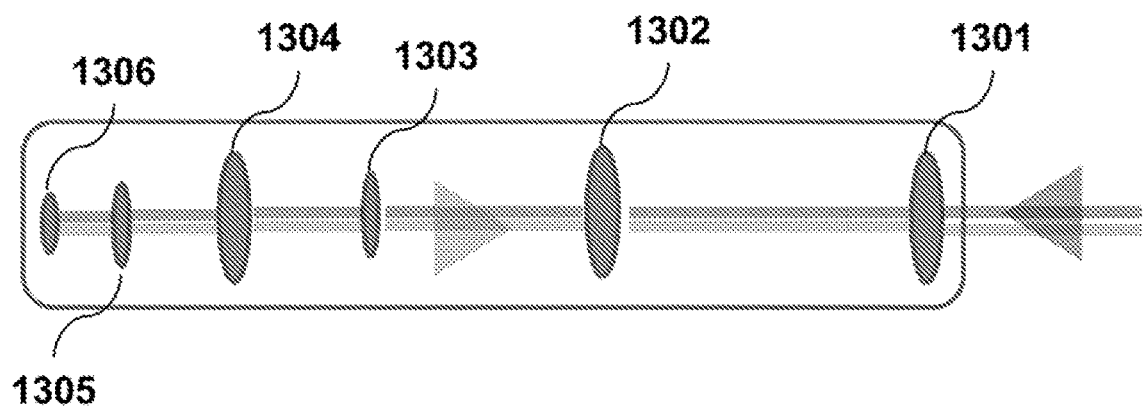

FIGS. 13A and 13B schematically illustrate an exemplary optical probe module. An optical probe module may comprise one or more relay lenses 1301 and 1302; a collimating lens 1303; a field lens 1304; and one or more objectives 1305 and 1306. The lenses and objectives of an optical probe module can both transmit light towards the epithelial tissue (top beam) and transmit the signals generated (lower beam) that relate to an intrinsic property of the epithelial tissue to a second collection module for signal processing and analysis.

Figure 14A:
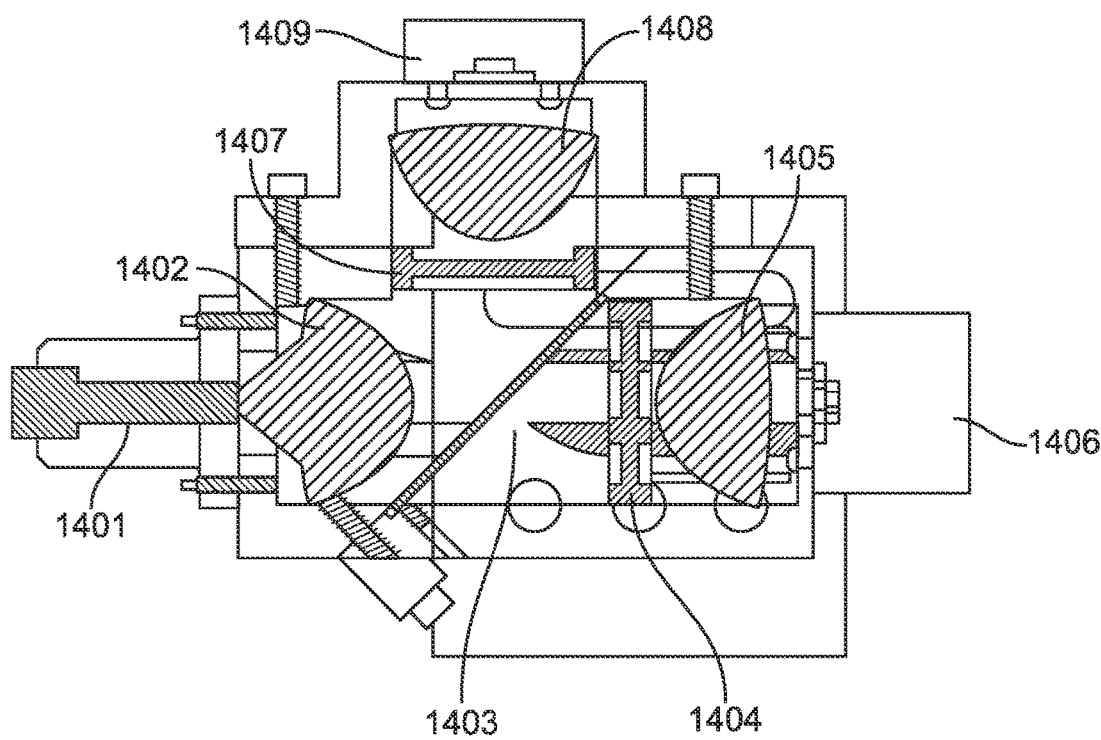
FIGS. 14A and 14B show the elements of an exemplary second collection module.
Figure 14B:
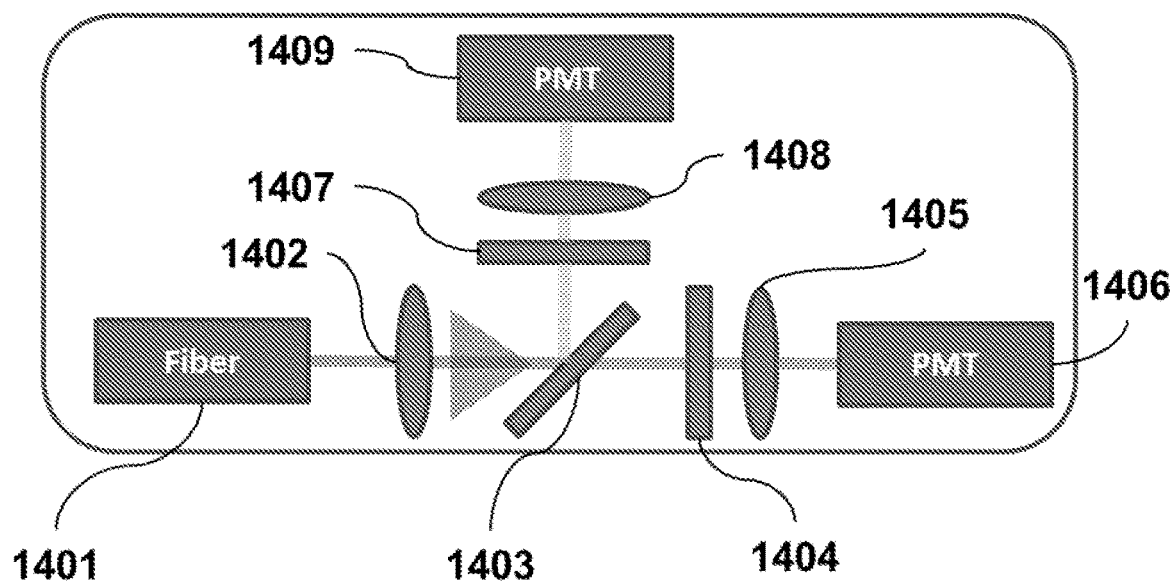

FIGS. 14A and 14B schematically illustrate an exemplary second collection module. A second collection module, such as a two color collection module, may comprise a fiber optic 1401; condenser lens 1402, 1405 and 1408; a dichroic 1403; optical filters 1404 and 1407; and photodetectors 1406 and 1409. A fiber optic 1401, such as a liquid light guide, may be used to transmit light from the first collection module to the second collection module. A condenser lens 1402, such as an aspheric condenser lens, may direct the collected light to a dichroic 1403, such as a longpass dichroic having cutoff of about 425 nm. The dichroic may transmit light with wavelengths shorter than the cutoff to a detector 1406 and divert light with wavelengths longer than the cutoff to an additional detector 1409. The transmitted light, for example, light with wavelengths shorter than about 425 nm, may be directed to an optical filter 1404, such as a SHG filter transmitting SHG signals, and a condenser lens 1405, such as an aspheric condenser lens, to a photodetector 1406, such as a photomultiplier tube (e.g., Hamamatsu PMT), where SHG signals are detected. The diverted light, for example light with wavelengths longer than about 425 nm, may be directed to an optical filter 1407, such as an autofluorescence filter transmitting autofluorescence signals, and a condenser lens 1408, such as an aspheric condenser lens, to another photodetector 1409, such as a photomultiplier tube (e.g., Hamamatsu PMT), where autofluorescence signals are detected. The collected SHG signals and autofluorescence signals may be processed, for example, using a programmed computer processor, to generate a profile (e.g., a depth profile) of the epithelial tissue which is usable to identify a disease in the epithelial tissue. The disease may be, for example, a skin cancer.

Figure 15A:
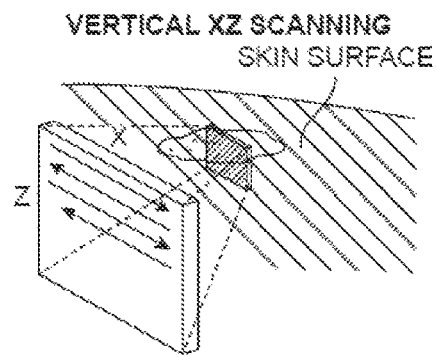
FIG. 15A shows vertical plane, or depth profile, scanning of epithelial tissue.
Figure 15B:
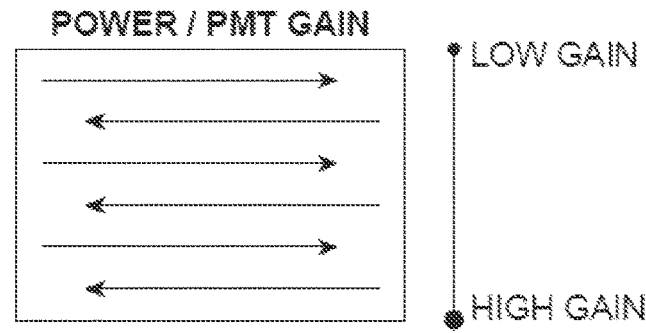
FIG. 15B shows power and PMT gain modulation during vertical plane, or depth profile, scanning for maximum image quality.
Figure 15C:
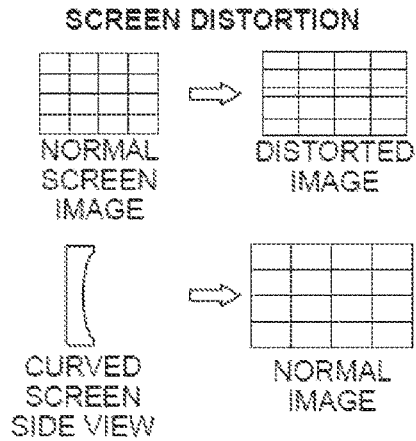
FIG. 15C shows the use of a curved display screen to remove image distortions from sinusoidal scanning.

FIG. 15A schematically illustrates vertical plane, or depth profile, scanning of a tissue. Imaging of the horizontal plane may be controlled by tilting a MEMS mirror in the x-direction and y-direction. Controlling the imaging depth may be achieved by altering the distance between a pair of lenses in an afocal arrangement. The depth profile may be produced by scanning the MEMS mirror along a single axis while repeatedly altering the distance between the pair of lenses to scan in the vertical direction. FIG. 15B shows schematically that the quality of the depth profile image may be altered by modulating the power and PMT gain during the scanning process. The signal strength through the tissue may decrease exponentially with depth. This decrease in signal strength may be counteracted by modulating both the power and PMT gain in real-time using a feedback signal algorithm to obtain images of uniform brightness and contrast across the full cross-sectional image. FIG. 15C illustrates image distortion that may occur due to sinusoidal scanning. Signal processing to build images may be done using raster scanning using the assumption that the microscope scans in a linear triangle wave. It may be difficult to move the MEMS mirror in a linear pattern and, therefore, the microscope may approximate the triangle wave scan using a sinusoidal scan. The sinusoidal scan may cause image distortion with expansion in the x-direction. This distortion may be counteracted by the use of display screen that is curved in the x-direction.

Figure 15D:
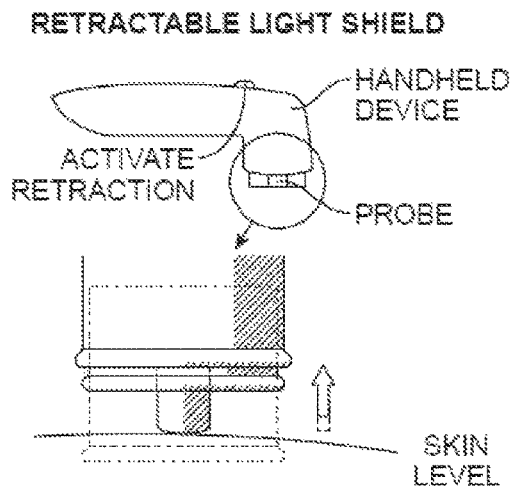
FIG. 15D show a retractable light shield on a handheld device.
Figure 15E:
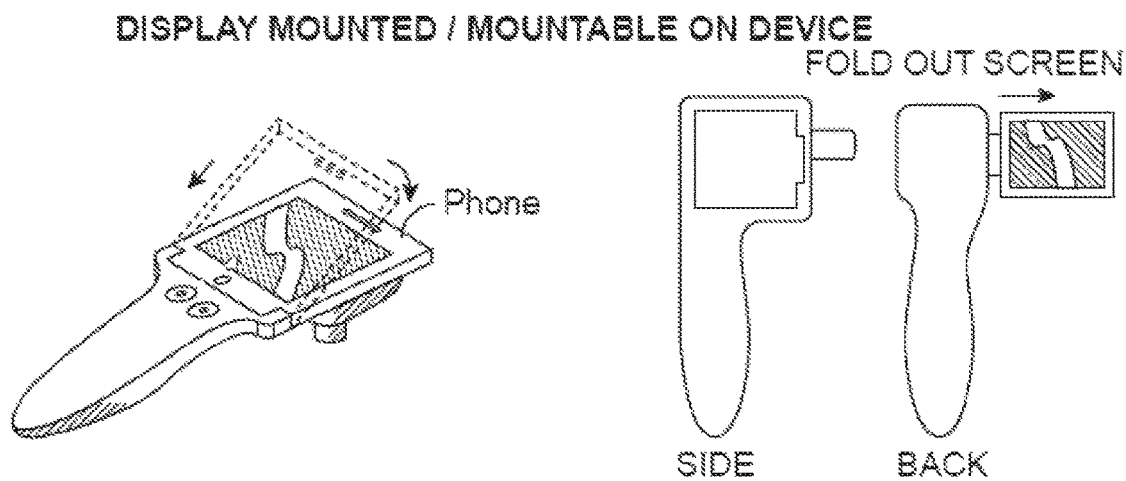
FIG. 15E shows a handheld device with a mounted and mountable display screen.

The handheld device may comprise many features to improve function and ease of use. FIG. 15D illustrates a handheld device with a retractable light shield. Higher resolution imaging may be achieved when ambient light pollution is minimized. In many situations, it may not be feasible to image in a dark room. Limiting light pollution may be achieved through the inclusion of a retractable light shield. The retractable light shield may be actuated using a button on the handheld device. The light shield may surround the probe and block light during scanning. The shield may be stored in a position that does not obscure the probe. The shield may comprise several layers of flexible opaque bristles capable of molding to all parts of the body. The handheld device may further comprise a display, as shown in FIG. 15E. The display may be permanently installed or the display may be removable. The display may also be stationary or mounted on hinge that allows for the display to fold and rotate.

Figure 16A:
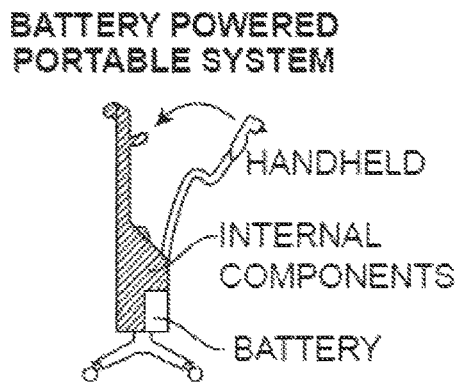
FIG. 16A shows a battery operated portable system.
Figure 16B:
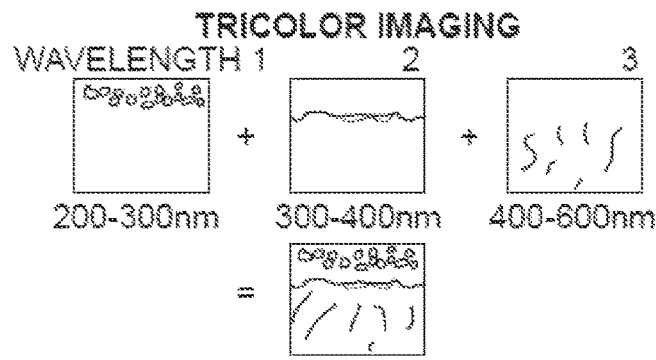
FIG. 16B shows tricolor imaging of epithelial tissue features with different spectral responses.

FIG. 16A shows an illustration of a portable, battery powered imaging system. The system may comprise wheels for easy movement, a stand to hold the handheld device while not in use, internal components including a computer processor, light generating source, and a battery. FIG. 16B shows tricolored images that may be generated by the system. The tricolor image may highlight features of the tissue characterized by different spectral responses. For example, the light collected by the handheld device may be filtered and sorted into collection channels by wavelength. Signal light may be filtered and sorted into a small number of collection channels comprising broad wavelength ranges or a large number of collection channels comprising narrow wavelength ranges. For example, signal light may be filtered and sorted into THG signals, SHG signals, and autofluorescence signals. THG signals may include a narrow band of collected light that is approximately one third of the wavelength of pulsed light. The wavelength range for collected THG signals may be centered at about 125 nm, 150 nm, 175 nm, 200 nm, 225 nm, 250 nm, 275 nm, 300 nm, 325 nm or longer. SHG signals may include a narrow band of collected light that is approximately one half of the wavelength of pulsed light (e.g., 390 nm). The wavelength range for collected SHG signals may be centered at about 200 nm, 225 nm, 275 nm, 300 nm, 325 nm, 350 nm, 375 nm, 400 nm, 425 nm, 450 nm, 475 nm or longer. Autofluorescence signals may include a narrow band of collected light or a broad band of collected light. The wavelength range for collected autofluorescence signals may range from 400 nm to 450 nm, 400 nm to 500 nm, 400 nm to 550 nm, 400 nm to 600 nm, 400 nm to 650 nm, 450 nm to 500 nm, 450 nm to 550 nm, 450 nm to 600 nm, 450 nm to 650 nm, 500 nm to 550 nm, 500 nm to 600 nm, 500 nm to 650 nm, 550 nm to 600 nm, 550 nm to 650 nm, or 600 nm to 650 nm.

Wavelength ranges may be assigned a color by the computer processor to generate multi-color images. For example, filtered and sorted SHG signals may represent dermis connective tissue and may be assigned to the color green. Filtered autofluorescence signals may be sorted into a single collection channel or divided by wavelength and sorted into multiple collection channels. For example, filtered autofluorescence signals may be sorted into two ranges, short and long. Signals within the short wavelength range may represent keratinocytes and may be assigned to the color blue. Signals within the long wavelength range may represent melanocytes and may be assigned the color red. The colorized signal information may be compiled into a single image.

Figure 16C:
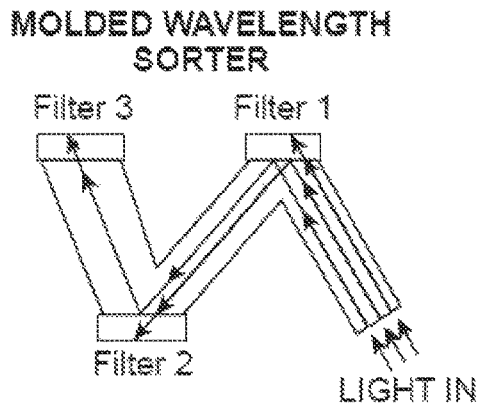
FIG. 16C shows a molded light sorter.

Filtering of the light may be achieved using a molded light sorter. FIG. 16C is an illustration of a molded light sorter, which may utilize total internal reflection to sort light while minimizing power loss. The molded light sorter may allow for a small form factor and simplification of the optics. The molded light sorter may comprise a glass or polymer molded into a three arm geometry. The three arm geometry may have filters glued to each end and also glued onto the glass face of the PMT. A liquid light guide may be glued directly onto the face of the mold. Direct gluing may minimize Fresnel reflections.

Figure 16D:
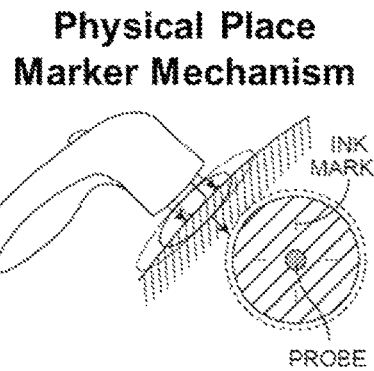
FIG. 16D shows a handheld device with a physical place-marking mechanism.
Figure 16E:
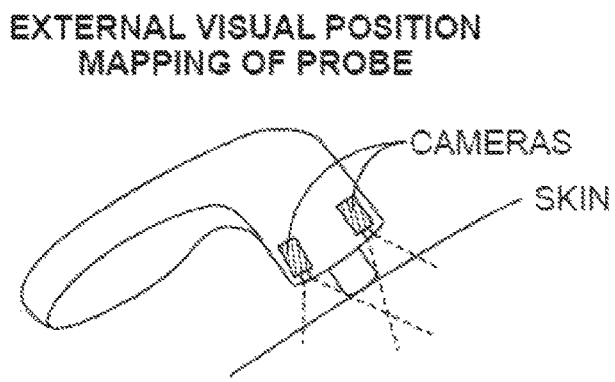
FIG. 16E shows a handheld device with external visual position mapping of the probe.
Figure 16F:
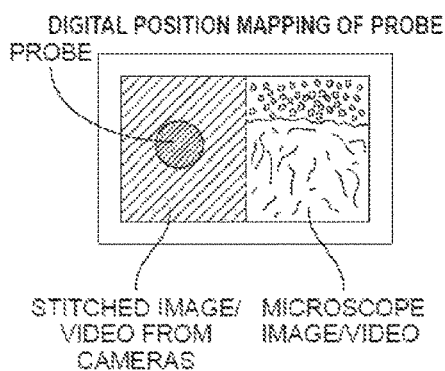
FIG. 16F shows digital position mapping of the probe.

The handheld device may further comprise features for positioning the probe and marking tissue. FIG. 16D shows a handheld device with a physical place-marking mechanism. The physical place-marking mechanism may allow users to place physical markings on the area of the tissue being viewed by the handheld device. For example, the physical place-marking mechanism may be used to mark the edges of a cancerous growth that cannot be seen by the naked eye. The marking material may include ink and the marker may be deployed by the press of a button. The handheld device may also comprise an external visual positioning mechanism. FIG. 16E shows a handheld device with dual cameras positioned on either side of the probe. The display may be modified to include a split screen that shows both the physical location of the probe and the microscope image. Additionally, the cameras may be used to create digital position mapping. FIG. 16F shows a split screen with a macroscopic image and a microscopic image. The macroscopic image may be generated by one or multiple cameras on the probe. Communication between the microscope and the cameras may enable digital markers from the microscopic image to be projected on the macroscopic image. Projecting features, or digital markers, from the microscopic image to the macroscopic image may enable boundaries of microscopic cancerous tissue to be shown as margin lines on the macroscopic image.

Figure 17A:
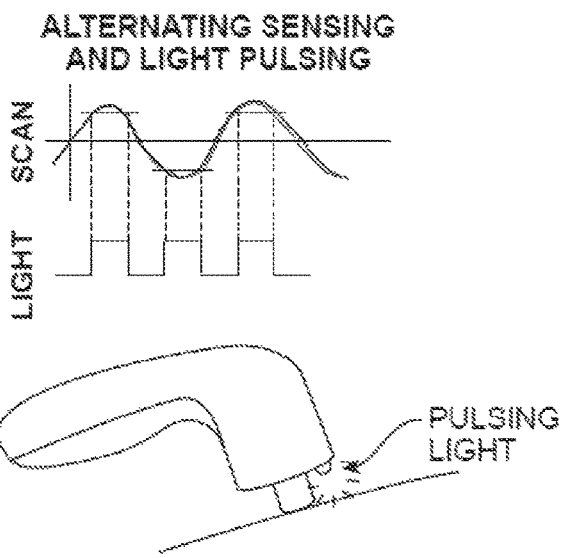
FIG. 17A shows a handheld device synchronizing sensing and pulsing of navigational light.

FIG. 17A shows a handheld device alternating light sensing and navigational light pulsing. When using sinusoidal scanning, only the approximate linear portion of the scan may be usable. As such, approximately 20% of the scan may be wasted. This wasted portion of the scan may be reduced by alternating light sensing with navigational light pulsing. For example, when the scan is in the linear portion of the sinusoidal scan the handheld device may be in the sensing mode and the navigational light pulsing may be off. When the scan is in the non-linear portion of the sinusoidal scan the handheld device may be in light pulsing mode and PMT sensor may be off. The light may be shut off by physically gating the light with a shutter. The light pulse may be at a high frequency to appear continuous to the human eye. Alternating light sensing and navigational light pulsing may be used in combination with a light shield, which may allow for the inside of the light shield to be illuminated. Illumination of the inside of the light shield may facilitate use of a positioning camera on the handheld device.

Figure 17B:
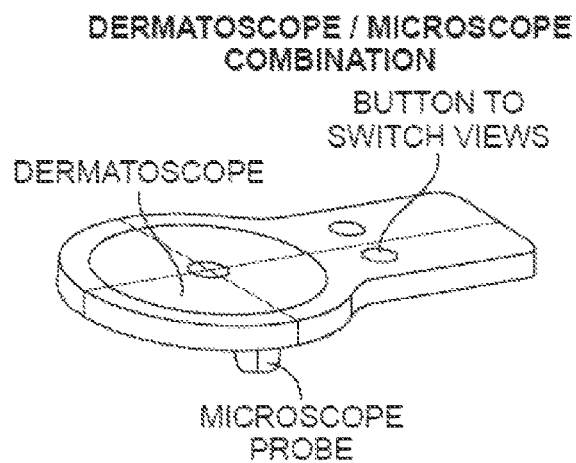
FIG. 17B shows an exemplary dermatoscope and microscope combination.

FIG. 17B shows an exemplary dermatoscope and microscope combination. Dermatoscopes may be used to enhance the view of skin lesions. The handheld device may be combined with a dermatoscope to maximize the functionality of the device. The dermatoscope may be an external magnifying glass or a camera near the end of the probe. The handheld device may have the ability to switch between dermatoscope and microscope functions.

Figure 17C:
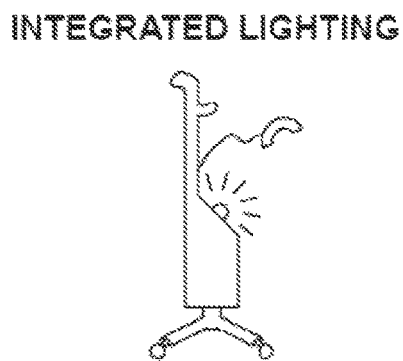
FIG. 17C shows a system with integrated lighting with spectral filtering.
Figure 17D:
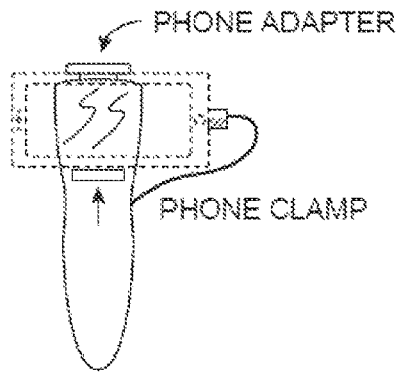
FIG. 17D shows a handheld device with a cellular phone adapter.
Figure 17E:
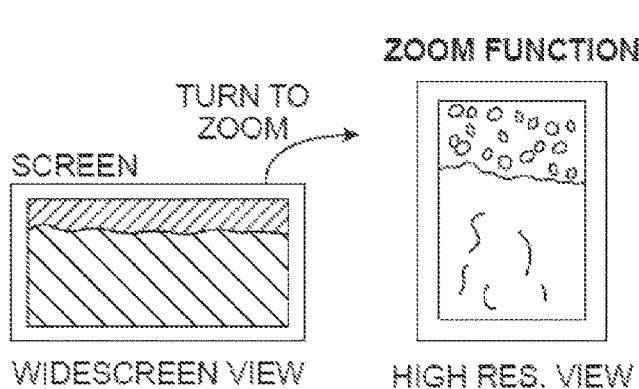
FIG. 17E shows a display with a zoom function capable of toggling between a high resolution and a wide field view.
Figure 17F:
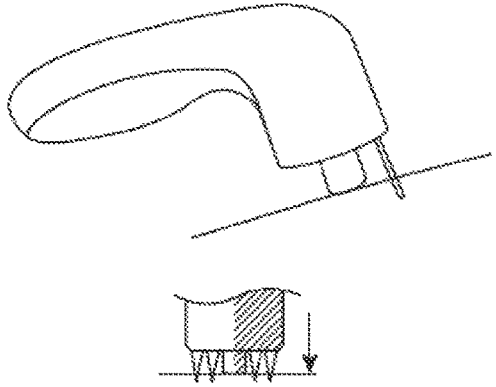
FIG. 17F shows a probe with a single deep margin light pipe needle and a probe with a ring of deep margin light pipe needles.

The imaging system may further comprise integrated lighting with a spectral filter to reduce light pollution. FIG. 17C shows an example imaging system comprising an integrated light source that emits filtered light. The filtered light may be undetectable to the handheld device. The light source may emit light with a wavelength from about 600 nm to 650 nm, 600 nm to 700 nm, 600 nm to 750 nm, 600 nm to 800 nm, 650 nm to 700 nm, 650 nm to 750 nm, 650 nm to 800 nm, 700 nm to 750 nm, 700 nm to 800 nm, or 750 nm to 800 nm. The imaging system may be further adapted to connect to a smartphone. FIG. 17D shows the handheld device with a clamp and cable to attach a smart phone. Compatible smart phones may include Apple® iPhone, Android-enabled device, and Blackberry® devices. The handheld device may further incorporate a zoom function. FIG. 17E shows a handheld device with a zoom function and a display capable of toggling between a wide screen view and a high resolution view. The zoom function may incorporate a lens or group of lenses into the light path of the handheld device to increase the field of view and create a wider image. The lens or group of lenses may be inserted after the MEMS mirror. The lens may act to modify the beam waist and cause the rays to emerge as a thinner beam at a wider angle while maintaining the focal distance. The wider angle may create a wider image. Creation of a wider image may reduce image resolution. To view the wider image, the handheld device display may be configured to toggle to a horizontal, widescreen orientation. Toggling between modes may be controlled by altering the orientation of the display or by pressing a button. To view the high resolution image, the handheld device may be configured to toggle to a vertical orientation and the lens between the MEMS mirror and next mirror may be removed from the light path.

FIG. 17E shows a handheld device with a probe comprising a single deep margin light pipe needle and a probe with a ring of deep margin light pipe needles. A large amount of light emitted from the handheld device may be lost to the surrounding tissue. To reduce the amount of light lost to the surrounding tissue and increase the maximum resolution depth of the depth profile below what may be detectable without puncturing the tissue, a light pipe needle may be inserted through the center of the tumor to absorb escaping light. The handheld device probe may comprise a single light pipe needle or multiple light pipe needles. Multiple light pipe needles may be used in a variety of configurations including in a ring configuration. The use of light pipe needles may provide higher quality images.

Figure 18:
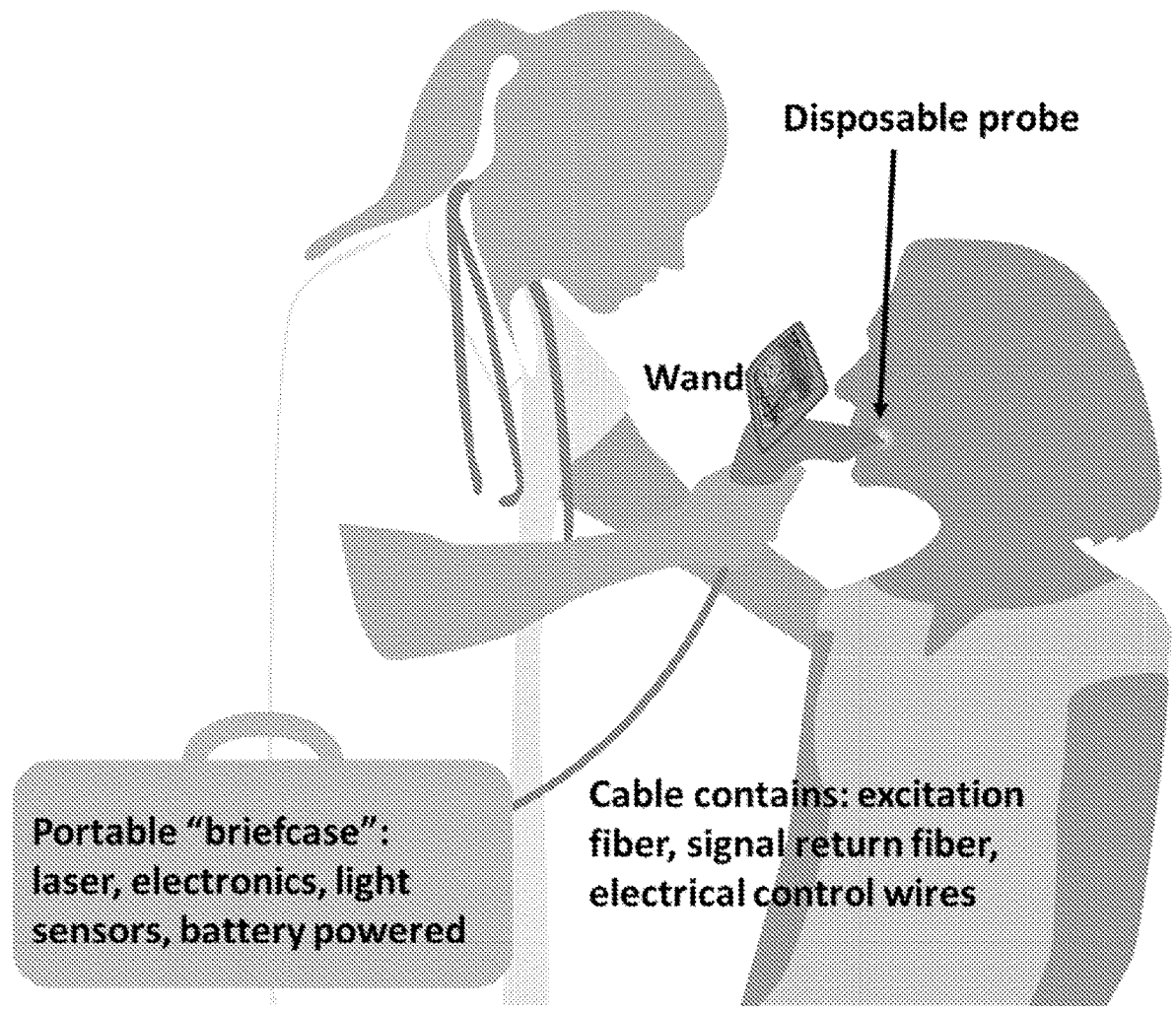
FIG. 18 shows the use of a handheld device with a disposable optical probe imaging tissue on the face of a patient.
Figure 26:
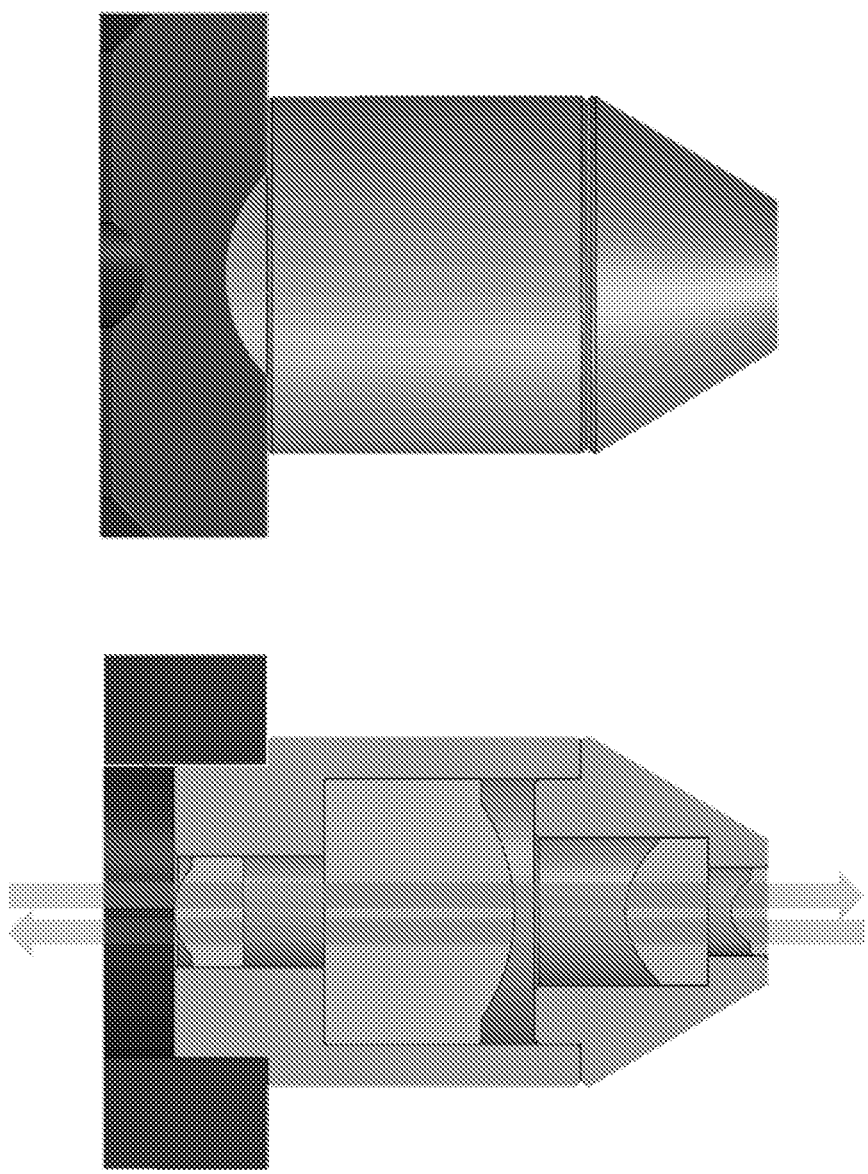
FIG. 26 shows an illustration of a disposable, non-invasive probe.

FIG. 18 illustrates a handheld device with a disposable probe tip. FIG. 26 shows an enlarged illustration of the disposable probe tip. The probe may have a tip diameter that is less than about 10 mm, 8 mm, 6 mm, 4 mm, or 2 mm. The handheld device may have a mechanism to allow for the disposable probe to be easily connected and disconnected. The mechanism may have an aligning function to enable precise optical alignment between the probe and the handheld device. The handheld device may be shaped like an otoscope or a dermatoscope with a gun-like form factor. The handheld device may have a weight of at most about 0.25 pounds (lbs), 0.5 lbs, 1 lb, 2 lbs, 4 lbs, or 8 lbs. A screen may be incorporated into the handheld device to give point-of-care viewing. The screen may be detachable and able to change orientation. The handheld device may be attached to a portable system which may include a rolling cart or a briefcase-type configuration. The portable system may include the laser, electronics, light sensors, and power system. The laser may provide light at an optimal frequency for delivery. The handheld device may include a second harmonic frequency doubler to convert the light from a frequency useful for delivery (e.g., 1560 nm) to one useful for imaging tissue (e.g., 780 nm). For example, the delivery frequency may be at least about 800 nm, 900 nm, 1000 nm, 1100 nm, 1200 nm, 1300 nm, 1400 nm, 1500 nm, 1600 nm, 1700 nm, 1800 nm, 1900 nm, or more and the imaging frequency may be at least about 400 nm, 450 nm, 500 nm, 550 nm, 600 nm, 650 nm, 700 nm, 750 nm, 800 nm, 850 nm, 900 nm, 950 nm or more. The laser may be of low enough power to run the system on battery power. The system may further comprise a charging dock or mini-stand to hold the portable unit during operation. There may be many mini-stands in a single medical office and a singly portable system capable of being transported between rooms.

Figure 19:
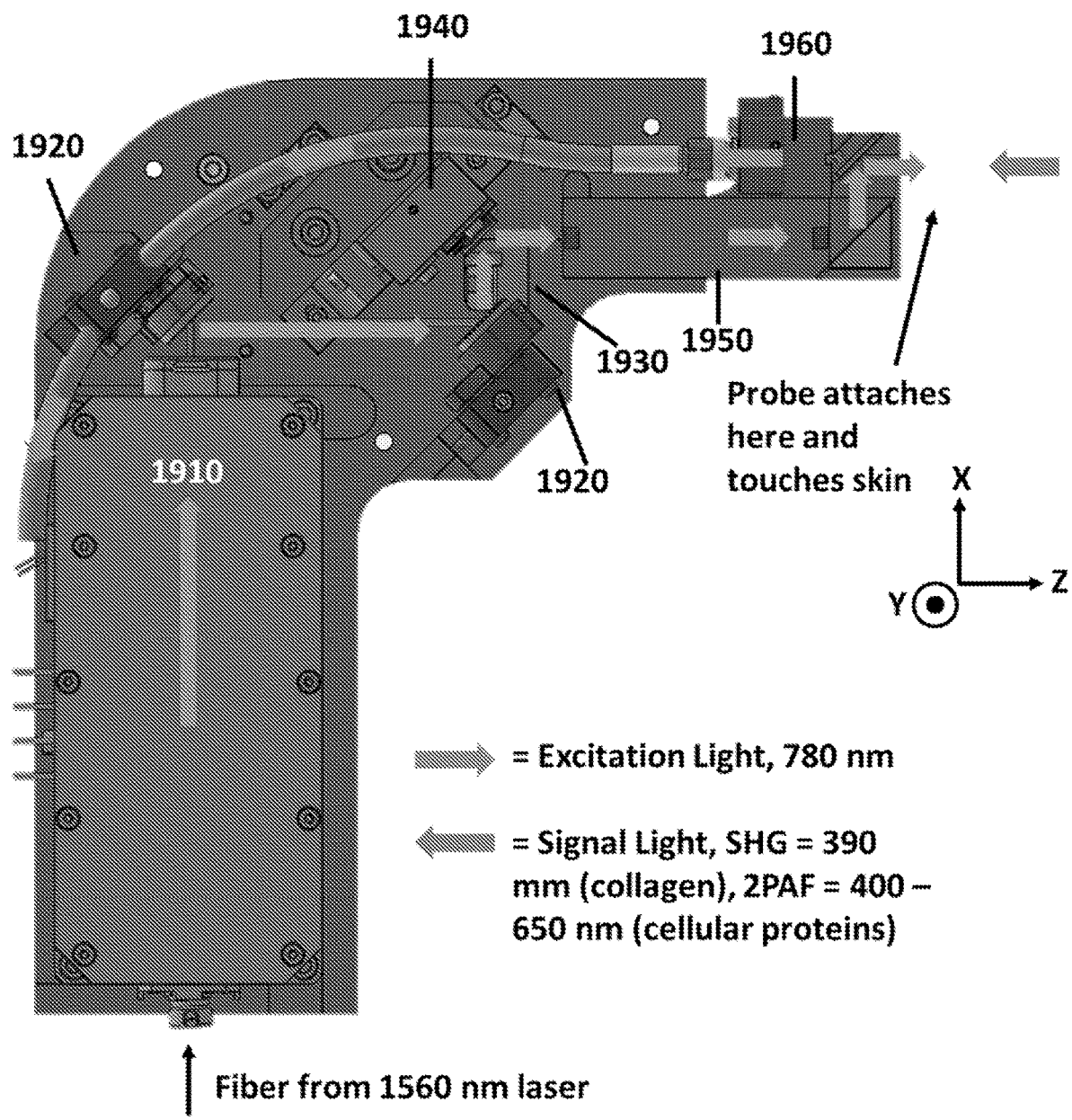
FIG. 19 shows an illustration of the internal features of a handheld device.

FIG. 19 shows an illustration of the internal components of the handheld device.

Figure 27A:
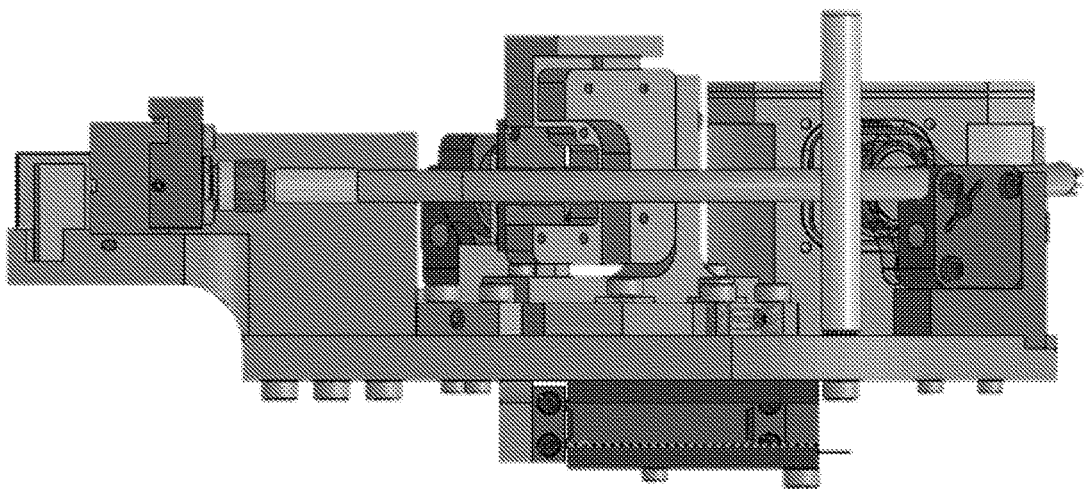
FIGS. 27A, 27B, and 27C show multiple orientations of the internal features of an example handheld device.
Figure 27B:
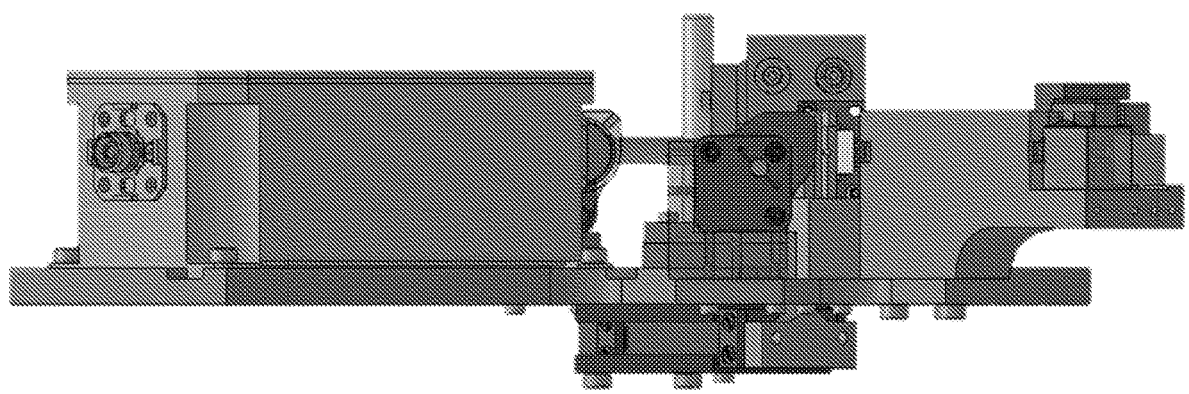
Figure 27C:
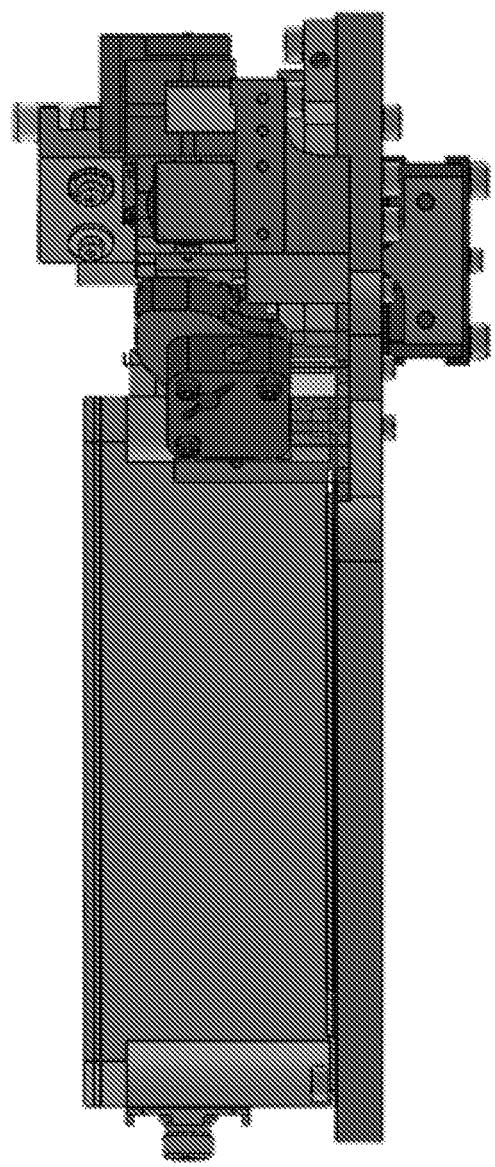

Additional orientations of the handheld device are shown in FIGS. 27A-27C. A laser may provide low frequency ultrafast pulsed light through a fiber optic cable to the handheld device. The beam of light may pass through a second harmonic frequency doubler 1910 where it may be collimated and converted to a higher frequency light. After passing through the frequency doubler 1910 the beam of light may contact one or more beam steering mirrors 1920. The beam steering mirrors 1920 may allow for optimized beam alignment. Once the beam alignment has been optimized by the beam steering mirrors 1920 it may contact an afocal z-plane scanner 1930. The afocal z-plane scanner may alter the focal point in the axial direction while scanning and enable depth profile imaging. Prior to entering the probe tip, the MEMS mirror 1940 may scan the beam in the x- and y-directions. The tip of the handheld device may comprise relay lenses 1950 that direct the beam of light to the back aperture of the probe to enter the tissue. The tip of the handheld device may further comprise collection optics 1960 that may reflect the lower frequency light used for imaging and collect the higher frequency signal light. FIG. 21B shows the excitation pathway from the afocal z-plane scanner through the probe objective.

Figure 20:
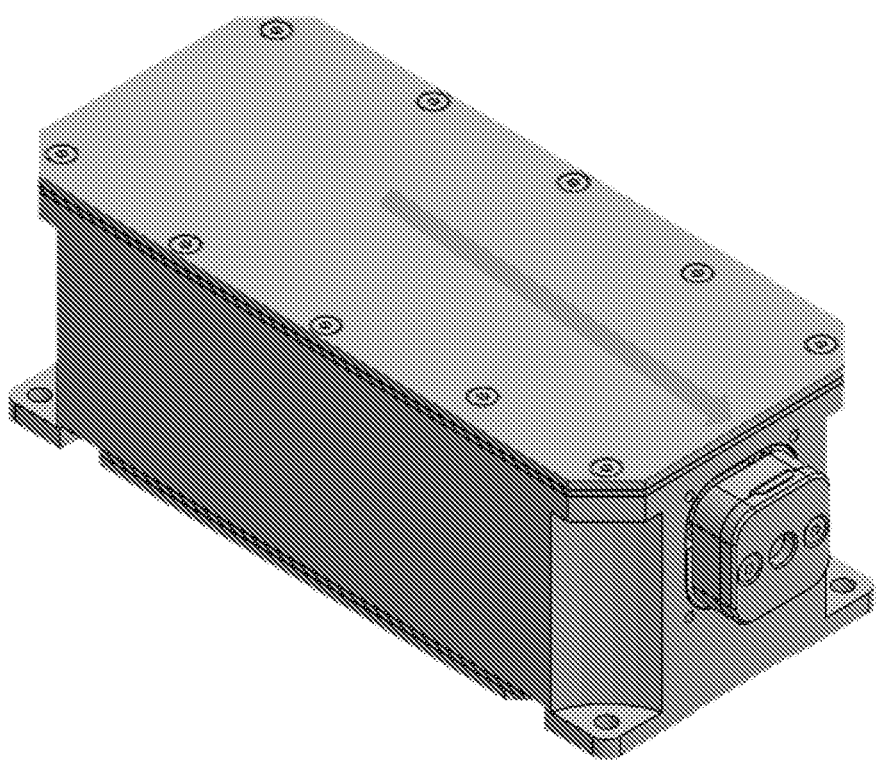
FIG. 20 shows an illustration of a second harmonic frequency doubler.

FIG. 20 is an enlarged illustration of the second harmonic frequency doubler 1910. The frequency doubler 1910 may comprise a non-linear crystal, such as a periodically poled lithium niobate crystal. The efficiency of the frequency doubler 1910 may vary as a function of temperature. To obtain optimal performance of the frequency doubler 1910 a temperature control and feedback sensor may be used to adjust the temperature of the unit based on the amount of light that is produced.

Figure 21A:
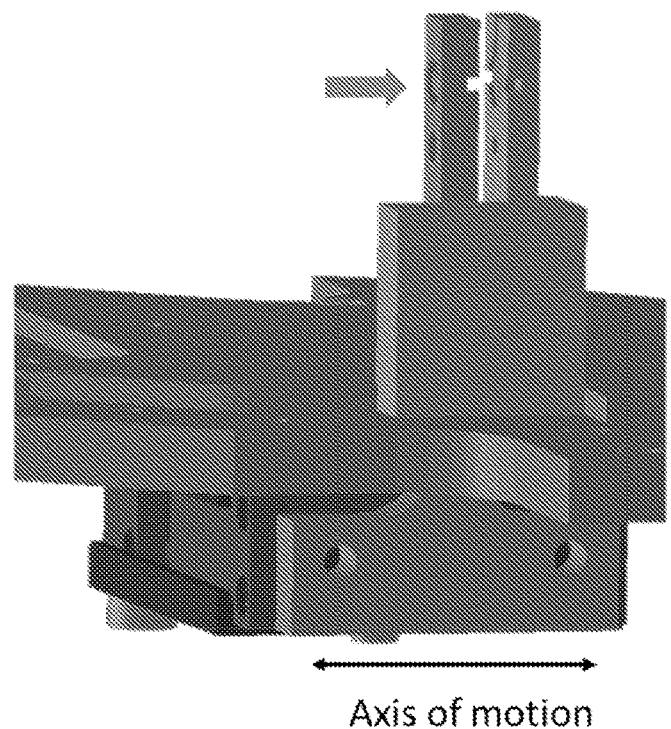
FIG. 21A shows an example device for scanning epithelial tissue in the z-plane.
Figure 21B:
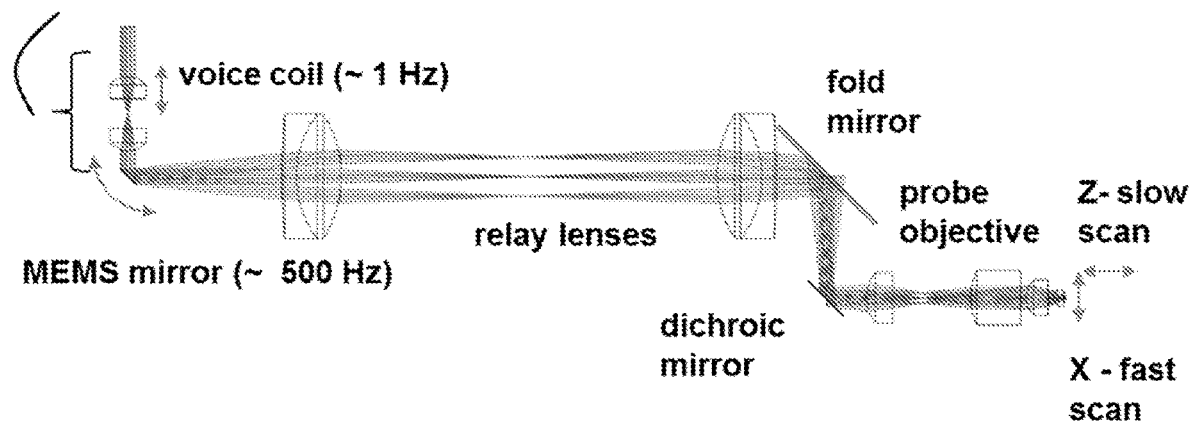
FIG. 21B shows an exemplary design of the excitation pathway for a device for scanning tissue in the z-plane.

FIG. 21A is an enlarged illustration of the afocal z-plane scanner 1930. The afocal z-plane scanner 1930 may converge or diverge the collimated beam of light, moving the focal point in the axial direction while imaging. Moving the focal point in the axial direction may allow for scanning the z-plane and enable imaging a depth profile. The mass of one of the lens may be small which may allow for the lens to scan at several Hz using a voice coil actuator. The afocal z-plane scanner may scan the line from the MEMS mirror 1940 in the z-direction and may act as a slow axis scan.

Figure 22:
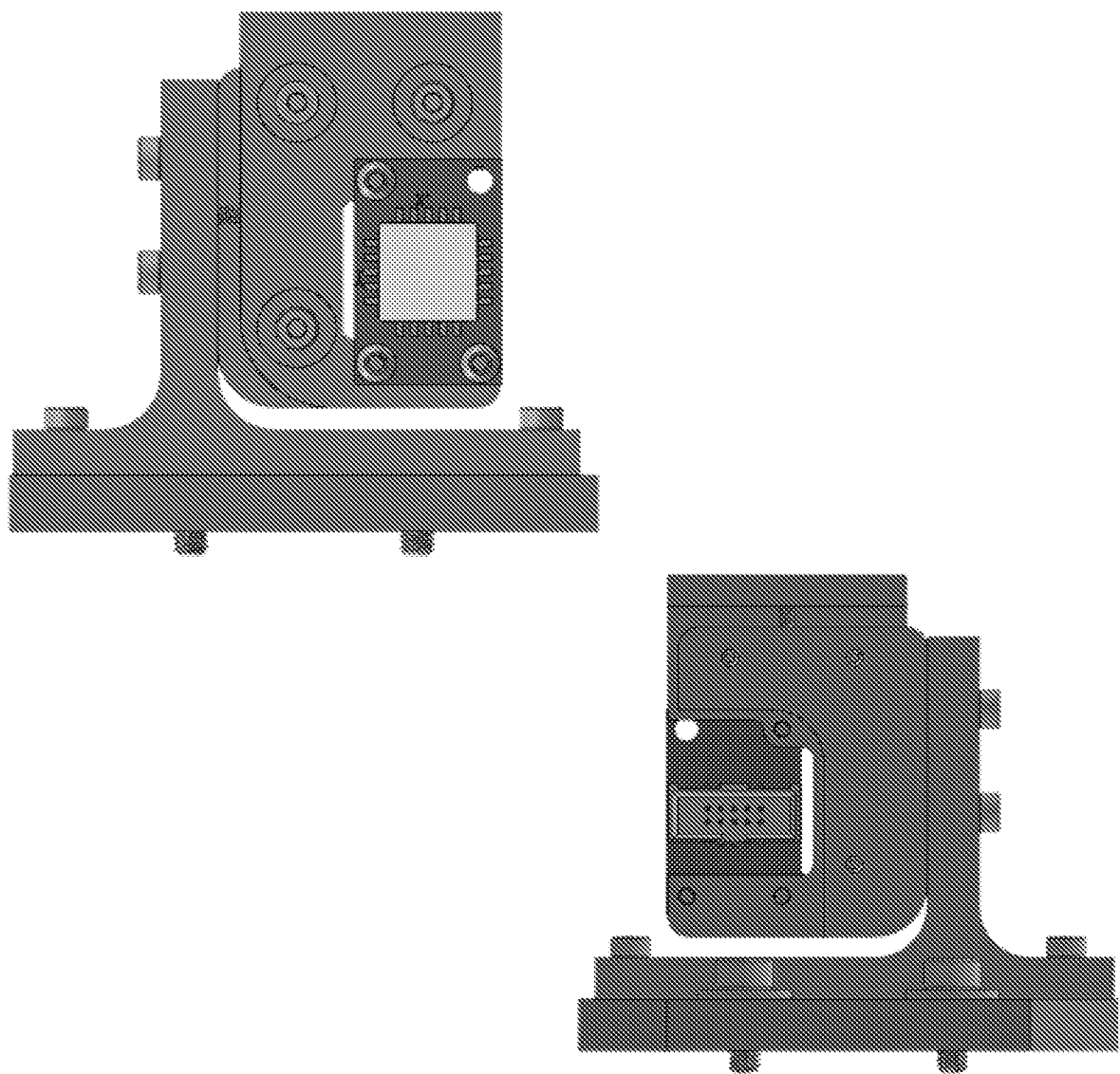
FIG. 22 shows an example device for scanning epithelial tissue in the horizontal plane.

FIG. 22 is an enlarged illustration of the MEMS mirror assembly 1940. For depth profile scanning, the MEMS mirror 1940 may quickly scan a line in the x-direction while the z-plane, or depth profile, scanner 1930 slowly shifts the line in the z-direction. For horizontal imaging, the MEMS mirror 1940 may scan quickly in the x-direction and slowly in the y-direction while the z-plane scanner may be used for quasi-static focusing.

Figure 23:
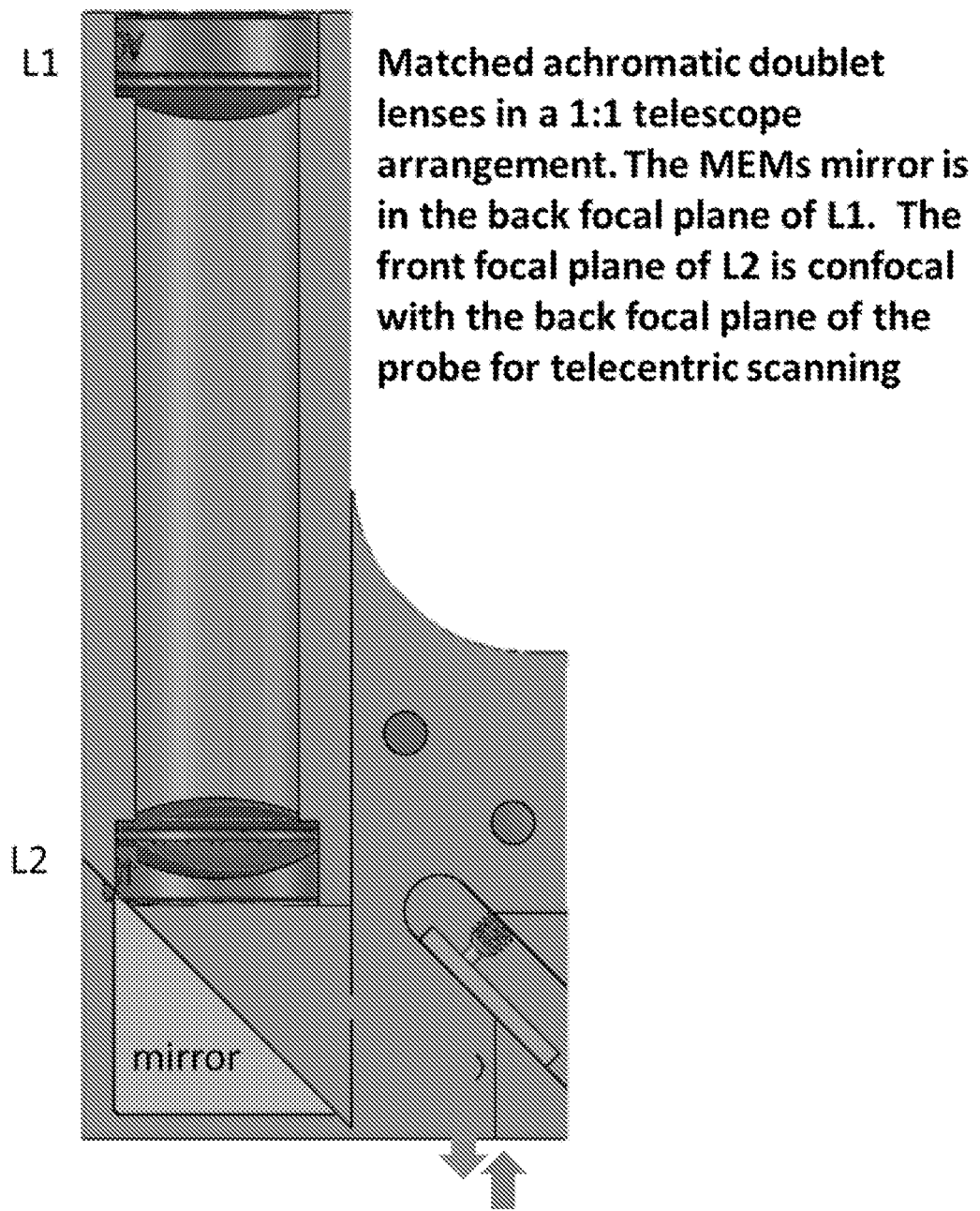
FIG. 23 shows example relay lenses that may be used during depth profile scanning.

FIG. 23 is an enlarged illustration of the relay lens assembly 1950 that directs the beam to the back aperture of the probe. The relay lenses 1950 may condition the light to enter the probe. The relay lenses 1950 may image the scan from the MEMS mirror 1940 and afocal z-plane scanner 1930 to the back focal plane of the objective which may make the scanning of the objective telecentric. To achieve a depth profile image that does not have a difference in magnification as a function of depth, it may be necessary to use a telecentric objective. The telecentric objective may also maintain a constant numerical aperture (NA), thus enabling constant resolution through the scanned region as well. A dichroic mirror in the excitation path may reflect the light used for imaging to the probe, but may allow signal light to pass through to the collection fiber.

Figure 24:
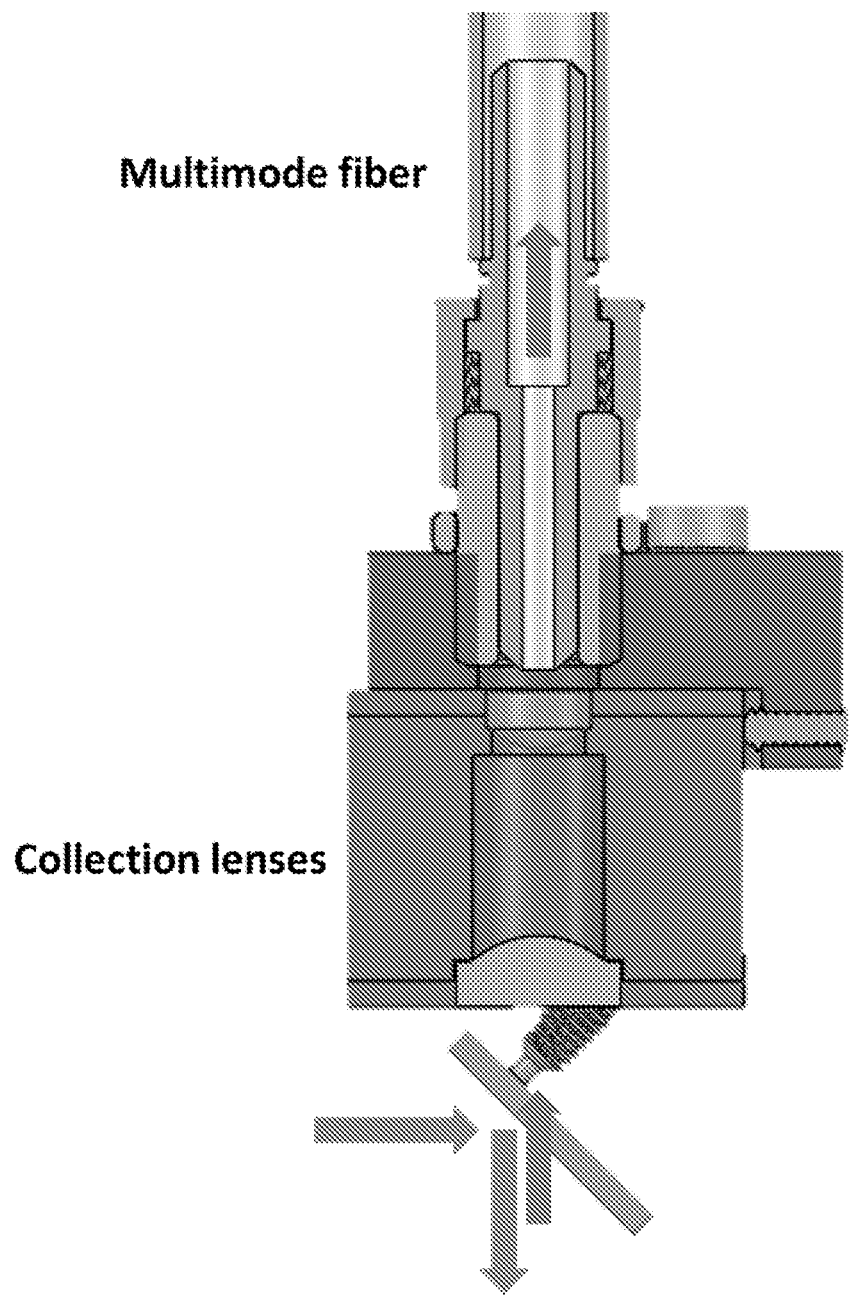
FIG. 24 shows an example configuration of collection optics that may be used for scanning tissue.

FIG. 24 is an enlarged illustration of the collection optics 1960. The collection optics 1960 may comprise dichroic mirrors that reflect low frequency light, such as the light used for imaging, to the tissue while delivering higher frequency light to a multi-mode fiber for delivery to the PMT sensors in the portable imaging system. The collection optics 1960 may comprise multiple lenses to direct the light to the multi-mode fiber or liquid light guide. Connective tissue may yield SHG of the excitation light and produce a narrow, high frequency signal (e.g., 390 nm). Certain proteins in the cells (e.g., NADH, melanin, FAD, keratin, elastin, etc.) may experience autofluorescence and may generate signals spanning a broad range of wavelengths. The multi-mode fiber or liquid light guide may deliver the signals to the portable imaging system in the collection unit which may separate the signals by wavelength.

Figure 25:
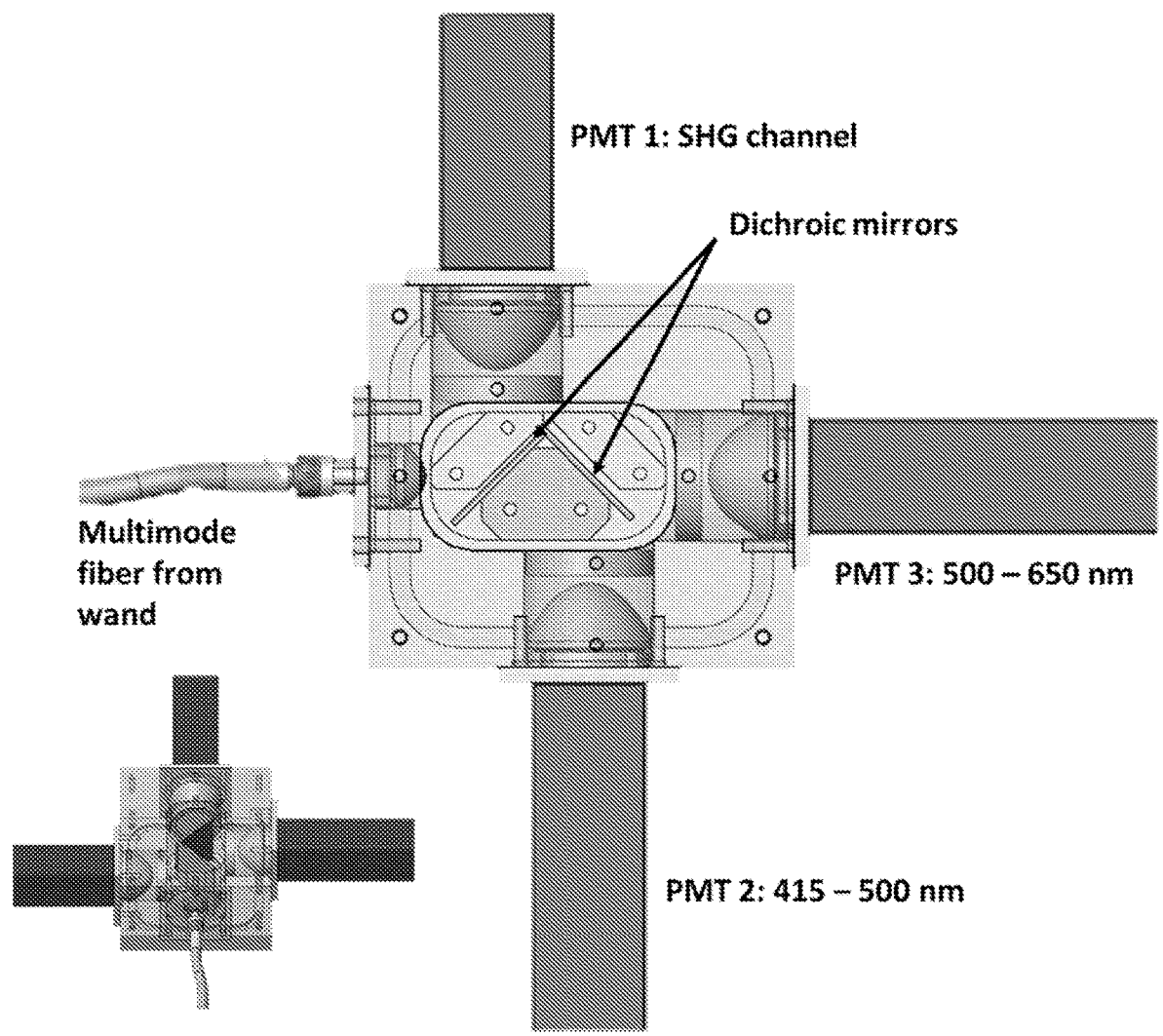
FIG. 25 shows an illustration of a collection unit that splits a combined signal from the handheld device into individual signals.

FIG. 25 is an illustration of the collection unit. The portable imaging system may comprise multiple PMT sensors. Light from the multi-mode or liquid light guide cable may be split into three components using multiple dichroic mirrors. The SHG portion of the signal may go to the first PMT sensor (PMT 1). The autofluorescence portion of the signal may split into two channels with one channel going to the second PMT sensor (PMT 2) and the second channel going to the third PMT sensor (PMT 3). Light entering each PMT may pass through an optical filter to remove background noise, back reflected light from the illuminating laser pulses, and mixing of light between PMT channels. Each PMT may provide a digital image of the intensity of its respective signal component. The computer processor may then be programmed to build a pixel by pixel image from each channel as the excitation is scanned. The images may then be compiled into a single image where each of original images is represented by a unique color, which may provide color contrast between the different tissue structures.

The imaging system may be completely mobile and can be moved by the clinician to the room where the patient is waiting. The machine can be powered on, and the physician can affix a removable probe to the handheld device. To optimize imaging, the clinician may use the machine under ambient light conditions, with the lights off, or with custom illumination that does not interfere with the microscope optics. The use of sensors with faster dynamics, such as hybrid photo multiplier tubes and avalanche photo diodes, may also enable optimized imaging with fewer ambient background signals. These types of hybrid sensors may have fast settling times, on the order of hundreds of picoseconds (ps). Increased dynamics may allow for the system to only sense signals during the pulse generation of the excitation laser and may eliminate recording of background light during intervals when the laser is not on. An alternative approach to minimizing background signals may be to include an additional fiber near the probe tip to measure the amount of ambient light entering the tissue along with an additional PMT sensor and electronics for this sampling probe. The signals from the sampling probe may then be removed from the signals detected from the pulsed light which may correct for the background signal. The probes can use water, alcohol, glycerin, petroleum jelly, or oil on the tip to improve optical coupling of light into the tissue. With the machine ready and the probe attached, the clinician can manipulate the microscope and probe to contact various regions of interest on the tissue while recording and displaying the resulting images in real time.

Computer Systems

Figure 28:
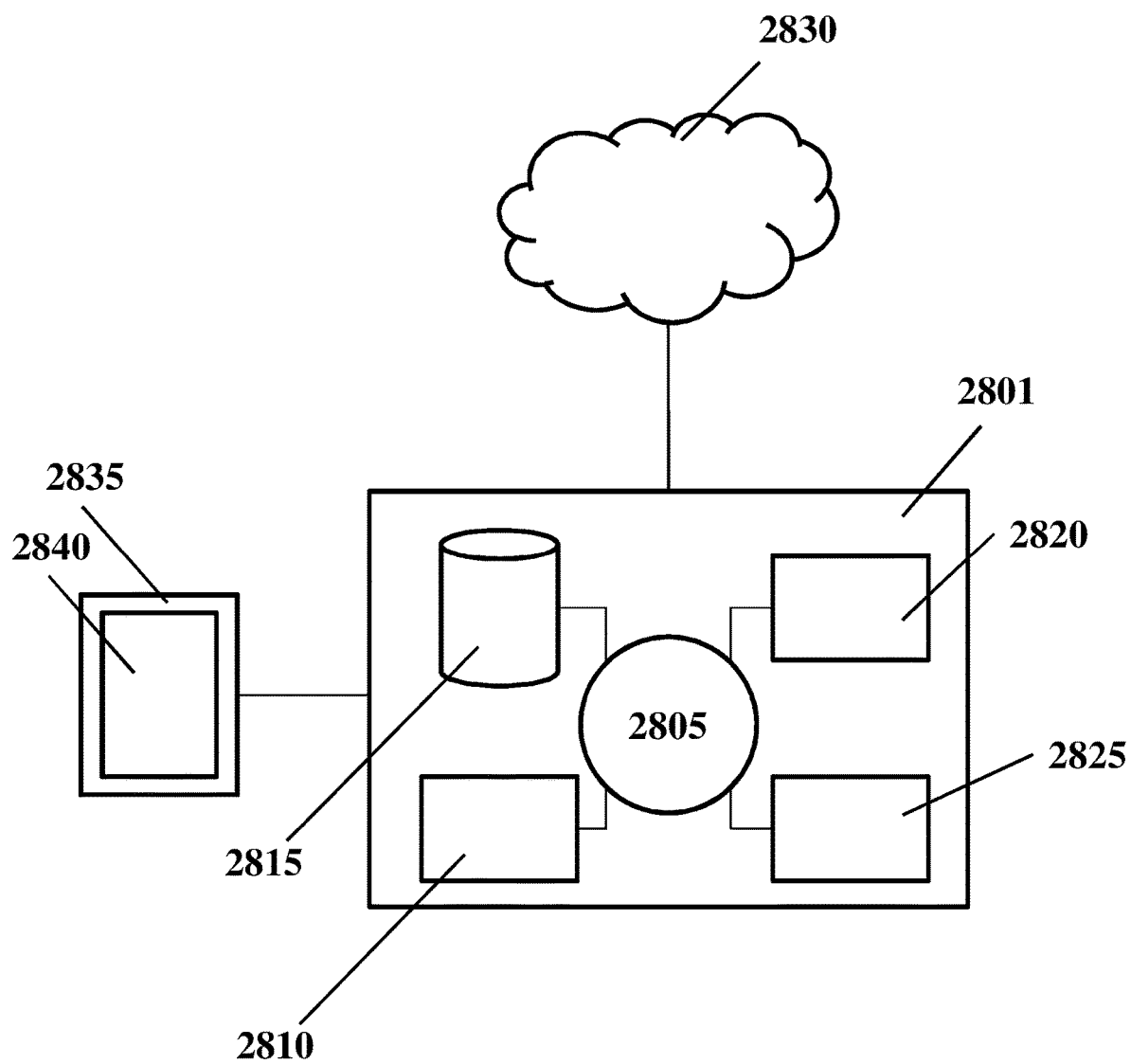
FIG. 28 shows an exemplary schematic of a computer control system that is programmed or otherwise configured to implement methods provided herein.

The present disclosure provides computer control systems that are programmed to implement methods of the disclosure. FIG. 28 shows a computer system 2801 that can be programmed or otherwise configured to implement the methods provided herein. The computer system 2801 can regulate various aspects of identifying a disease in an epithelial tissue of a subject, such as, for example, collecting at least a subset of the signals generated at a plurality of different focal planes and using the signals to generate a depth profile of the epithelial tissue. The computer system 2801 can be an electronic device of a user or a computer system that can be remotely located with respect to the electronic device. The electronic device can be a mobile electronic device.

The computer system 2801 includes a central processing unit (CPU, also "processor" and "computer processor" herein) 2805, which can be a single core or multi core processor, or a plurality of processors for parallel processing. The computer system 2801 also includes memory or memory location 2810 (e.g., random-access memory, read-only memory, flash memory), electronic storage unit 2815 (e.g., hard disk), communication interface 2820 (e.g., network adapter) for communicating with one or more other systems, and peripheral devices 2825, such as cache, other memory, data storage and/or electronic display adapters. The memory 2810, storage unit 2815, interface 2820 and peripheral devices 2825 are in communication with the CPU 2805 through a communication bus (solid lines), such as a motherboard. The storage unit 2815 can be a data storage unit (or data repository) for storing data. The computer system 2801 can be operatively coupled to a computer network ("network") 2830 with the aid of the communication interface 2820. The network 2830 can be the Internet, an internet and/or extranet, or an intranet and/or extranet that can be in communication with the Internet. The network 2830 in some cases can be a telecommunication and/or data network. The network 2830 can include one or more computer servers, which can enable distributed computing, such as cloud computing. The network 2830, in some cases with the aid of the computer system 2801, can implement a peer-to-peer network, which may enable devices coupled to the computer system 2801 to behave as a client or a server.

The CPU 2805 can execute a sequence of machine-readable instructions, which can be embodied in a program or software. The instructions may be stored in a memory location, such as the memory 2810. The instructions can be directed to the CPU 2805, which can subsequently program or otherwise configure the CPU 2805 to implement methods of the present disclosure. Examples of operations performed by the CPU 2805 can include fetch, decode, execute, and writeback.

The CPU 2805 can be part of a circuit, such as an integrated circuit. One or more other components of the system 2801 can be included in the circuit. In some cases, the circuit is an application specific integrated circuit (ASIC).

The storage unit 2815 can store files, such as drivers, libraries and saved programs. The storage unit 2815 can store user data, e.g., user preferences and user programs. The computer system 2801 in some cases can include one or more additional data storage units that are external to the computer system 2801, such as located on a remote server that is in communication with the computer system 2801 through an intranet or the Internet.

The computer system 2801 can communicate with one or more remote computer systems through the network 2830. For instance, the computer system 2801 can communicate with a remote computer system of a user (e.g., service provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2801 via the network 2830.

Methods as described herein can be implemented by way of machine (e.g., computer processor) executable code stored on an electronic storage location of the computer system 2801, such as, for example, on the memory 2810 or electronic storage unit 2815. The machine executable or machine readable code can be provided in the form of software. During use, the code can be executed by the processor 2805. In some cases, the code can be retrieved from the storage unit 2815 and stored on the memory 2810 for ready access by the processor 2805. In some situations, the electronic storage unit 2815 can be precluded, and machine-executable instructions are stored on memory 2810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2801 can include or be in communication with an electronic display 2835 that comprises a user interface (UI) 2840 for providing, for example, depth profile of an epithelial tissue. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2805. The algorithm can, for example, generate a depth profile using the subset of signals collected at a plurality of different focal planes. In some cases, the algorithm can generate a depth profile in real-time.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method for identifying a disease in an epithelial tissue of a subject, comprising:
 (a) using an optical probe to transmit pulses of a single beam of light from a light source towards a surface of the epithelial tissue, which pulses of the single beam of light, upon contacting the epithelial tissue, generate signals indicative of an intrinsic property of the epithelial tissue;

(b) collecting at least a subset of the signals at a plurality of different focal planes of the pulses of the single beam of light, wherein the optical probe comprises an objective that maintains a constant numerical aperture, and wherein the objective is stationary during collecting; and (c) using a programmed computer processor to process the subset of the signals to generate a depth profile of the epithelial tissue, which depth profile is usable to identify the disease in the epithelial tissue of the subject.

2. The method of claim 1, wherein (a)-(c) are performed in an absence of administering a contrast enhancing agent to the subject.

3. The method of claim 1, wherein the pulses of the single beam of light comprise unpolarized light.

4. The method of claim 1, wherein the pulses of the single beam of light comprise polarized light.

5. The method of claim 4, wherein the polarized light is rotated.

6. The method of claim 1, wherein the depth profile extends at least below a basal layer of the epithelial tissue.

7. The method of claim 1, further comprising changing a relative position of a mobile lens with respect to the epithelial tissue, which mobile lens is in optical communication with the optical probe, to yield the plurality of different focal planes.

8. The method of claim 7, wherein changing the relative position of the mobile lens with respect to the epithelial tissue comprises translating the mobile lens at a cyclic rate of at least 0.5 Hertz (Hz).

9. The method of claim 1, further comprising modulating a curvature of an electrically or electro-mechanically tunable lens, which electrically or electro-mechanically tunable lens is in electrical or electro-mechanical communication with the optical probe, to yield the plurality of different focal planes.

10. The method of claim 1, further comprising outlining a boundary that is indicative of a location of the disease in the epithelial tissue of the subject.

11. The method of claim 1, wherein the pulses of the single beam of light are synchronized with sensing by a photomultiplier tube (PMT) sensor.

12. The method of claim 1, wherein (a) is performed without penetrating the epithelial tissue of the subject or in an absence of removing the epithelial tissue from the subject.

13. The method of claim 1, wherein (a) further comprises directing the pulses of light from the light source through a frequency doubler to convert the pulses of light from a first frequency to a second frequency.

14. A method for identifying a disease in an epithelial tissue of a subject, comprising:

(a) without penetrating the epithelial tissue of the subject, using an optical probe to transmit pulses of light from a light source towards a surface of the epithelial tissue, wherein the pulses of light, upon contacting the epithelial tissue, generate signals indicative of an intrinsic property of the epithelial tissue, and wherein the pulses of light are directed to the epithelial tissue using a mobile lens at a plurality of different relative positions with respect to the epithelial tissue;

(b) collecting at least a subset of the signals generated from the pulses of light, wherein the optical probe comprises an objective that maintains a constant numerical aperture, and wherein the objective is stationary during collecting; and (c) using a programmed computer processor to process the subset of the signals to generate a profile of the epithelial tissue, which profile is usable to identify the disease in the epithelial tissue of the subject.

15. The method of claim 14, wherein the pulses of light are pulses of a single beam of light.

16. The method of claim 14, wherein the profile is a depth profile.

17. The method of claim 14, wherein the optical probe is in contact with the surface of the epithelial tissue.

18. The method of claim 17, wherein the contact is monitored.

19. The method of claim 14, wherein the optical probe is translatable across the surface of the epithelial tissue.

20. The method of claim 14, wherein the collecting is performed in a presence of ambient light, wherein the optical probe comprises an additional sensor that detects the amount of ambient light present during collection of the signals generated from the pulses of light, and wherein the programmed computer processor is programmed to remove the amount of ambient light from the signals generated from the pulses of light.

21. The method of claim 14, wherein the profile is presented on a customizable display.

22. The method of claim 14, wherein (a) further comprises directing the pulses of light from the light source through a frequency doubler to convert the pulses of light from a first frequency to a second frequency.

* * * * *